United States Patent
Van Almsick et al.

(10) Patent No.: US 6,376,429 B1
(45) Date of Patent: Apr. 23, 2002

(54) BENZOYLCYCLOHEXANEDIONES, PROCESS FOR THEIR PREPARATION AND THEIR USE AS HERBICIDES AND PLANT GROWTH REGULATORS

(75) Inventors: Andreas Van Almsick, Oberursel; Lothar Willms, Hofheim; Thomas Auler, Kelsterbach; Hermann Bieringer, Eppstein; Christopher Rosinger, Hofheim, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/414,455

(22) Filed: Oct. 7, 1999

(30) Foreign Application Priority Data

Oct. 10, 1998 (DE) .......................... 198 46 792

(51) Int. Cl.⁷ ...................... C07C 317/24; A01N 35/06; A01N 41/10
(52) U.S. Cl. .................. 504/271; 504/292; 504/294; 504/333; 504/348; 548/240; 549/427; 549/498; 564/99; 568/329
(58) Field of Search ................. 504/271, 292, 504/294, 333, 348; 548/240; 549/427, 498; 564/99; 568/329

(56) References Cited

U.S. PATENT DOCUMENTS

| | | | | |
|---|---|---|---|---|
| 4,954,165 A | 9/1990 | Baba et al. | ..................... | 71/103 |
| 4,957,538 A | 9/1990 | Michaely | ........................ | 71/98 |

FOREIGN PATENT DOCUMENTS

| | | |
|---|---|---|
| DE | 42 41 999 | 6/1994 |
| GB | 2 327 418 A | 1/1999 |
| JP | 2-222 | 1/1990 |
| JP | 8-20544 | 1/1996 |
| JP | 11-21274 * | 1/1999 |
| WO | WO 99/03845 | 1/1999 |
| WO | WO 99/07688 | 2/1999 |
| WO | WO 99/10327 | 3/1999 |

OTHER PUBLICATIONS

Japanese Abstract No. 08020554, Jan., 1996.
Patent Abstracts of Japan 07206808, Aug., 1995.

\* cited by examiner

*Primary Examiner*—Richard L. Raymond
*Assistant Examiner*—Deepak R. Rao
(74) *Attorney, Agent, or Firm*—Frommer Lawrence & Haug LLP

(57) ABSTRACT

Benzoylcyclohexanediones of the formula (I), process for their preparation and their use as herbicides and plant growth regulators are described.

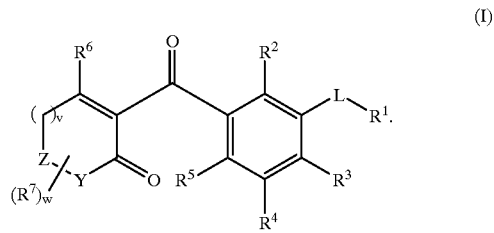

In this formula (I), $R^1{}_1$, $R^2$, $R^3$, $R^4$, $R^5$, $R^6$ and $R^7$ are various radicals, L is an alkylene chain, and Y and Z are a monoatomic bridge element.

12 Claims, No Drawings

BENZOYLCYCLOHEXANEDIONES, PROCESS FOR THEIR PREPARATION AND THEIR USE AS HERBICIDES AND PLANT GROWTH REGULATORS

The invention relates to the technical field of the herbicides and plant growth regulators, in particular that of the herbicides for the selective control of weeds and weed grasses in useful plant crops.

It is already disclosed in various patents that certain benzoylcyclohexanediones, inter alia also those which carry, for example, a radical linked via a bridge in the 3-position of the phenyl ring, have herbicidal properties. Thus in JP-A 08 020554 those benzoylcyclohexanediones are described which carry a substituted phenoxymethyl radical in the position mentioned. JP-A 02 00222 describes benzoylcyclohexanediones which likewise carry a radical linked via a bridge in the 3-position mentioned, this bridge containing at least one atom from the group consisting of oxygen, sulfur and nitrogen. WO 99/10327, WO 99/07688 and WO 99/03845 describe benzoylcyclohexanediones which in the 3-position carry a heterocyclic radical linked via a carbon chain, which in the case of WO 99/07688 is also interrupted by heteroatoms.

The use of the benzoylcyclohexanediones known from these patents is, however, frequently associated with disadvantages in practice. Thus the herbicidal or plant growth-regulating activity of the known compounds is not always adequate, or if the herbicidal activity is adequate undesired damage to the useful plants is observed.

The object of the present invention is the provision of compounds which have a herbicidal and plant growth-regulating action and which overcome the disadvantages known from the prior art.

The object is achieved by benzoylcyclohexanediones, specifically substituted in the 3-position of the phenyl ring, of the formula (I)

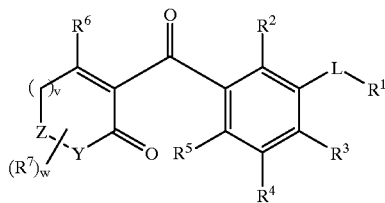

(I)

in which the substituents and symbols have the following meaning:

$R^1$ is an optionally substituted hydrocarbon radical, which optionally additionally contains one or more, identical or different heteroatoms from the group consisting of phosphorus, oxygen, sulfur, nitrogen, fluorine, chlorine, bromine and iodine;

$R^2$, $R^3$, $R^4$ and $R^5$ independently of one another are hydrogen, hydroxyl, thio, amino, cyano, nitro, halogen or an optionally substituted hydrocarbon radical, which optionally additionally contains one or more, identical or different heteroatoms from the group consisting of phosphorus, oxygen, sulfur, nitrogen, fluorine, chlorine, bromine and iodine;

$R^6$ is $OR^{12}$, alkylthio, haloalkylthio, alkenylthio, haloalkenylthio, alkynylthio, haloalkynylthio, alkylsulfinyl, haloalkylsulfinyl, alkenylsulfinyl, haloalkenylsulfinyl, alkynylsulfinyl, haloalkynylsulfinyl, alkylsulfonyl, haloalkylsulfonyl, alkenylsulfonyl, haloalkenylsulfonyl, alkynylsulfonyl, haloalkynylsulfonyl, cyano, cyanato, thiocyanato or halogen;

$R^7$ is hydrogen, tetrahydropyran-3-yl, tetrahydropyran-4-yl, tetrahydrothiopyran-3-yl, alkyl, cycloalkyl, alkoxy, alkoxyalkyl, alkylcarbonyl, alkoxycarbonyl, alkylthio, phenyl, where the eight last-mentioned groups are optionally substituted by one or more, identical or different radicals from the group consisting of halogen, alkylthio and alkyloxy, or two radicals $R^7$ bonded to a common carbon atom form a chain from the group consisting of $OCH_2CH_2O$, $OCH_2CH_2CH_2O$, $SCH_2CH_2S$ and $SCH_2CH_2CH_2S$, this optionally being substituted by one to four methyl groups, or two radicals $R^7$ bonded to directly adjacent carbon atoms form a bond or, with the carbon atoms carrying them, form a 3- to 6-membered ring optionally substituted by one or more, identical or different radicals from the group consisting of halogen, alkyl, alkylthio and alkoxy;

$R^{12}$ is hydrogen, alkyl, haloalkyl, alkoxyalkyl, formyl, alkylcarbonyl, alkoxycarbonyl, alkylaminocarbonyl, dialkylaminocarbonyl, alkylsulfonyl, haloalkylsulfonyl, benzoyl or phenylsulfonyl, the two last-mentioned groups optionally being substituted by one or more, identical or different radicals from the group consisting of alkyl, haloalkyl, alkoxy, haloalkoxy, halogen, cyano and nitro;

L is a $C_1$–$C_6$-alkylene chain which is optionally substituted by one or more, identical or different radicals $R^2$;

Y is a divalent unit from the group consisting of O, S, N—H, N-alkyl, $CHR^7$ and $C(R^7)_2$;

Z is a direct bond, a divalent unit from the group consisting of O, S, SO, $SO_2$, N—H, N-alkyl, $CHR^7$ and $C(R^7)_2$;

v is 1 or 2;

w is 0, 1, 2, 3 or 4, with the proviso that —L—$R^1$ should not be optionally substituted $CH_2$—O-phenyl when $R^2$ and $R^3$ are each chlorine and $R^4$ and $R^5$ are each hydrogen.

Numerous compounds of the formula (I) according to the invention can occur in different tautomeric structures, depending on external conditions, such as solvent and pH.

In the case in which $R^6$ is hydroxyl, the following tautomeric structures are possible:

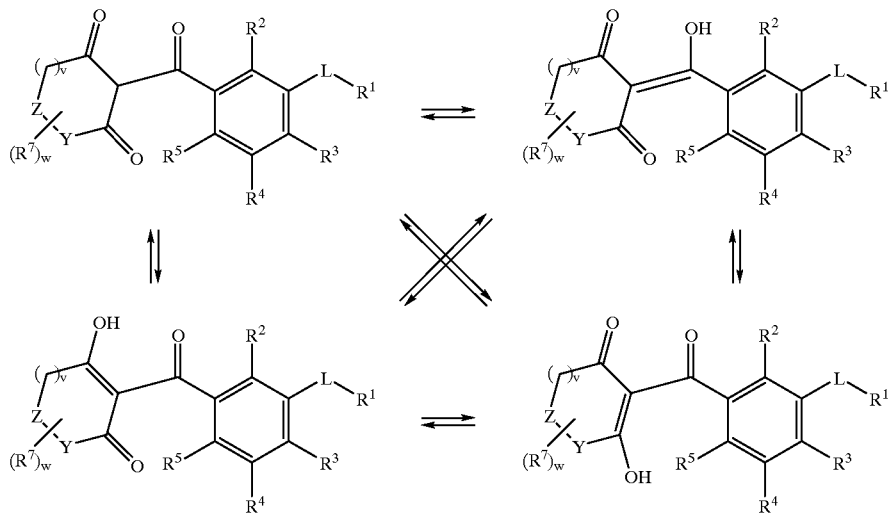

Depending on the type of substituents, the compounds of the formula (I) contain an acidic proton which can be removed by reaction with a base. Suitable bases are, for example, alkali metals, such as lithium, sodium and potassium, alkaline earth metals, such as calcium and magnesium, ammonia and organic amines. Such salts are likewise a subject of the invention.

A hydrocarbon radical is a straight-chain, branched or cyclic, saturated, partly saturated, unsaturated or aromatic radical, e.g. alkyl, alkenyl, alkynyl, cycloalkyl, cycloalkenyl, cycloalkynyl or aryl. Combined terms, such as cycloalkylalkenyl, cycloalkynylalkyl and arylalkynyl, are also intended to be included by this definition. If this hydrocarbon radical also additionally contains heteroatoms, these can in principle, i.e. if the chemical structure permits it, be located in any desired position of the hydrocarbon radical. According to the definition, a heteroatom can also function as a connecting atom to the remainder of the molecule. A heteroatom can be present in single- or double-bonded form.

In formula (I) and all subsequent formulae, chain-like carbon-containing radicals such as alkyl, alkoxy, haloalkyl, haloalkoxy, alkylamino and alkylthio and the corresponding unsaturated and/or substituted radicals in the carbon structure such as alkenyl and alkynyl can in each case be straight-chain or branched. If not specifically indicated, in these radicals the lower carbon structures, e.g. having 1 to 6 carbon atoms or, in the case of unsaturated groups, having 2 to 4 carbon atoms, are preferred. Alkyl radicals, even in the combined meanings such as alkoxy, haloalkyl etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the possible unsaturated radicals corresponding to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl. The multiple bond can be located in any desired position of the unsaturated radical.

Cycloalkyl is a carbocyclic, saturated ring system having three to eight carbon atoms, e.g. cyclopropyl, cyclopentyl or cyclohexyl. Analogously, cycloalkenyl is a monocyclic alkenyl group having three to eight carbon ring members, e.g. cyclopropenyl, cyclobutenyl, cyclopentenyl and cyclohexenyl, it being possible for the double bond to be located in any desired position. In the case of combined radicals, such as cycloalkylalkenyl, the first-mentioned radical can be located in any desired position of the second-mentioned radical.

In the case of a disubstituted amino group, such as dialkylamino, these two substituents can be identical or different.

Halogen is fluorine, chlorine, bromine or iodine. Haloalkyl, -alkenyl and -alkynyl are alkyl, alkenyl or alkynyl, each of which is partly or completely substituted by halogen, preferably by fluorine, chlorine and/or bromine, in particular by fluorine or chlorine, e.g. $CF_3$, $CHF_2$, $CH_2F$, $CF_3CF_2$, $CH_2FCHCl$, $CCl_3$, $CHCl_2$, $CH_2CH_2Cl$; haloalkoxy is for example, $OCF_3$, $OCHF_2$, $OCH_2F$, $CF_3CF_2O$, $OCH_2CF_3$ and $OCH_2CH_2Cl$; the same applies to haloalkenyl and other radicals substituted by halogen.

The term heterocyclyl is understood as meaning three- to six-membered, saturated or partially unsaturated mono- or polycyclic heterocycles, which contain one to three heteroatoms selected from a group consisting of oxygen, nitrogen and sulfur. Linkage can take place, if chemically possible, at any desired position of the heterocycle. Examples thereof are 2-tetrahydrofuranyl, oxiranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxoazolidinyl, 3-isothioazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3- dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 1-morpholinyl, 2-morpholinyl, 3-morpholinyl, 1-piperidinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzo-thiazin-2-yl, 1,3-dithian-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl.

Aryl is an aromatic mono- or polycyclic hydrocarbon radical, e.g. phenyl, naphthyl, biphenyl or phenanthryl.

Heteroaryl is an aromatic radical which contains one to five heteroatoms from the group consisting of nitrogen, oxygen and sulfur in addition to carbon ring members. Examples of 5-membered heteroaryl are 2-pyrrolyl, 3-pyrrolyl, 3-pyrazolyl, 4-pyrazolyl, 5-pyrazolyl, 2-imidazolyl, 4-imidazolyl, 1,2,4-triazolyl-3-yl, 1,3,4-triazol-2-yl, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl. Examples of 6-membered heteroaryl are 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl. Examples of fused 5-membered heteroaryl are benzothiazol-2-yl and benzoxazol-2-yl. Examples of benzo-fused 6-membered heteroaryl are quinoline, isoquinoline, quinazoline and quinoxaline.

The statement "partially or completely halogenated" is intended to express that in the groups characterized in this way the hydrogen atoms can be partly or completely replaced by identical or different halogen atoms as mentioned above.

If a group is polysubstituted, this is to be understood as meaning that in the combination of the various substituents the general principles of the construction of chemical compounds are to be followed, i.e. that compounds are not formed which the person skilled in the art knows to be chemically unstable or not possible.

Depending on the nature and linkage of the substituents, the compounds of the formula I can be present as stereoisomers. If, for example, one or more alkenyl groups are present, diastereomers can occur. If, for example, one or more asymmetric carbon atoms are present, enantiomers and diastereomers can occur. Stereoisomers can be obtained from the mixtures produced during preparation by customary separation methods, for example by chromatographic separation procedures. Likewise, stereoisomers can be selectively prepared by the use of stereoselective reactions using optically active starting substances and/or auxiliaries. The invention also relates to all stereoisomers and mixtures thereof which are included by the formula I, but which are not specifically defined.

For the selection of the meanings of "Y" and "Z", it is intended to apply that "Y" and "Z" in each case are not simultaneously a heteroatomic divalent unit.

If a radical is described as optionally substituted without further details with respect to the nature of the substituents, this is intended to mean that this radical can be substituted by one or more, identical or different radicals $R^2$.

Of further interest are compounds of the formula (I), in which $R^1$ is cycloalkyl, cycloalkenyl, aryl, cycloalkoxy, cycloalkylalkoxy, cycloalkylalkenyloxy, cycloalkylalkynyloxy, cycloalkenyloxy, cycloalkenylalkoxy, cycloalkenylalkenyloxy, cycloalkenylalkynyloxy, aryloxy, arylalkoxy, arylalkenyloxy, arylalkynyloxy, cycloalkylthio, cycloalkylalkylthio, cycloalkylalkenylthio, cycloalkylalkynylthio, cycloalkenylthio, cycloalkenylalkylthio, cycloalkenylalkenylthio, cycloalkenylalkynylthio, arylthio, arylalkylthio, arylalkenylthio, arylalkynylthio, optionally substituted mono- or diarylamino, optionally substituted mono- or diheteroarylamino, optionally substituted N-alkyl-N-arylamino, optionally substituted N-alkyl-N-heteroarylamino, cycloalkylamino, cycloalkenylamino, heterocyclylalkylamino, heterocyclylalkenylamino, cycloalkylsulfonyl, cycloalkylalkylsulfonyl, cycloalkylalkenylsulfonyl, cycloalkylalkynylsulfonyl, cycloalkenylsulfonyl, cycloalkenyl-alkylsulfonyl, cycloalkenylalkenylsulfonyl, cycloalkenylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, cycloalkylsulfinyl, cycloalkylalkylsulfinyl, cycloalkylalkenylsulfinyl, cycloalkylalkynylsulfinyl, cycloalkenylsulfinyl, cycloalkenylalkylsulfinyl, cycloalkenylalkenylsulfinyl, cycloalkenylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, heterocyclylalkylsulfinyl, heterocyclylalkenylsulfinyl, heterocyclylalkynylsulfinyl, aminosulfonyl, optionally substituted mono- or dialkylaminosulfonyl, optionally substituted mono- or diarylaminosulfonyl, optionally substituted mono- or diheteroarylaminosulfonyl, optionally substituted N-alkyl-N-arylaminosulfonyl, optionally substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, cycloalkenylsulfonyloxy, cycloalkenylalkylsulfonyloxy, cycloalkenylalkenylsulfonyloxy, cycloalkenylalkynylsulfonyloxy, arylsulfonyloxy, arylalkylsulfonyloxy, arylaikenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfonylamino, cycloalkylalkenylsulfonylamino, cycloalkylalkynylsulfonylamino, cycloalkenylsulfonylamino, cycloalkenylalkylsulfonylamino, cycloalkenylalkenylsulfonylamino, cycloalkenylalkynylsulfonylamino, arylsulfonylamino, arylalkylsulfonylamino, arylalkenylsulfonylamino, arylalkynylsulfonylamino, heteroarylsulfonylamino, heteroarylalkylsulfonylamino, heteroarylalkenylsulfonylamino, heteroarylalkynylsulfonylamino, alkylsulfonyl-N-alkylamino, alkenylsulfonyl-N-alkylamino, alkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, cycloalkenylsulfonyl-N-alkylamino, cycloalkenylalkylsulfonyl-N-alkylamino, cycloalkenylalkenylsulfonyl-N-alkylamino, cycloalkenylalkynylsulfonyl-N-alkylamino, arylsulfonyl-N-alkylamino, heteroarylsulfonyl-N-alkylamino, arylalkylsulfonylamino, heteroarylalkylsulfonyl-N-alkylamino, arylalkenylsulfonyl-N-alkylamino, heteroarylalkenylsulfonyl-N-alkylamino, arylalkynylsulfonyl-N-alkylamino, heteroarylalkynylsulfonyl-N-alkylamino, heterocyclylsulfonyl-N-alkylamino, heterocyclylalkylsulfonyl-N-alkylamino, heterocyclylalkenylsulfonyl-N-alkylamino, heterocyclylalkynylsulfonyl-N-alkylamino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, cycloalkenylcarbonyl, cycloalkenylalkylcarbonyl, cycloalkenylalkenylcarbonyl, cycloalkenylalkynylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, heterocyclylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, cycloalkenyloxycarbonyl, cycloalkenylalkoxycarbonyl, cycloalkenylalkenyloxycarbonyl, cycloalkenylalkynyloxycarbonyl, aryloxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, aminocarbonyl, optionally substituted mono- or dialkylaminocarbonyl, optionally substituted mono- or diarylaminocarbonyl, optionally substituted mono- or diheteroarylaminocarbonyl, optionally substituted N-alkyl-N-arylaminocarbonyl, optionally substituted N-alkyl-N-heteroarylaminocarbonyl, optionally substituted mono- or diheteroarylaminocarbonyloxy, optionally substituted N-alkyl-N-arylaminocarbonyloxy, optionally substituted N-alkyl-N-heteroarylaminocarbonyloxy, aminocarbonylamino, optionally substituted mono- or dialkylaminocarbonylamino, optionally substituted mono- or diarylaminocarbonylamino, optionally substituted mono- or diheteroarylaminocarbonylamino, optionally substituted N-alkyl-N-arylaminocarbonylamino, optionally substituted N-alkyl-N-heteroarylaminocarbonylamino, cycloalkylcarbonyloxy, cycloalkylalkylcarbonyloxy, cycloalkylalkenylcarbonyloxy, cycloalkylalkynylcarbonyloxy, cycloalkenylcarbonyloxy, cycloalkenylalkylcarbonyloxy, cycloalkenylalkenylcarbonyloxy, cycloalkenylalkynylcarbonyloxy, arylcarbonyloxy, arylalkylcarbonyloxy, arylalkenylcarbonyloxy, arylalkynylcarbonyloxy, heteroarylcarbonyloxy, heteroarylalkylcarbonyloxy, heteroarylalkenylcarbonyloxy, heteroarylalkynylcarbonyloxy, heterocyclylcarbonyloxy, heterocyclylalkylcarbonyloxy, heterocyclylalkenylcarbonyloxy, heterocyclylalkynylcarbonyloxy, optionally substituted mono- or dialkylcarbonylamino, optionally substituted mono- or diarylcarbonylamino, optionally substituted mono- or diheteroarylcarbonylamino, optionally substituted alkylcarbonyl-N-arylamino, optionally substituted arylcarbonyl-N-alkylamino, optionally substituted alkylcarbonyl-N-heteroarylamino, optionally substituted heteroarylcarbonyl-N-alkylamino, alkoxycarbonylamino, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, cycloalkenyloxycarbonylamino, cycloalkenylalkoxycarbonylamino, cycloalkenylalkenyloxycarbonylamino, cycloalkenylalkynyloxycarbonylamino, aryloxycarbonylamino, arylalkoxycarbonylamino, arylalkenyloxycarbonylamino, arylalkynyloxycarbonylamino, heteroaryloxycarbonylamino, heteroarylalkoxycarbonylamino,
heteroarylalkenyloxycarbonylamino,
heteroarylalkynyloxycarbonylamino,
heterocyclyloxycarbonylamino,
heterocyclylalkoxycarbonylamino,
heterocyclylalkenyloxycarbonylamino,
heterocyclylalkynyloxycarbonylamino,
alkoxycarbonyloxy, alkenyloxycarbonyloxy,
alkynyloxycarbonyloxy, cycloalkoxycarbonyloxy,
cycloalkylalkoxycarbonyloxy,
cycloalkylalkenyloxycarbonyloxy,
cycloalkylalkynyloxycarbonyloxy,
cycloalkenyloxycarbonyloxy,
cycloalkenylalkoxycarbonyloxy,
cycloalkenylalkenyloxycarbonyloxy,
cycloalkenylalkynyloxycarbonyloxy,
aryloxycarbonyloxy, arylalkoxycarbonyloxy,
arylalkenyloxycarbonyloxy,
arylalkynyloxycarbonyloxy,
heteroaryloxycarbonyloxy,
heteroarylalkoxycarbonyloxy,
heteroarylalkenyloxycarbonyloxy,
heteroarylalkynyloxycarbonyloxy,
heterocyclyloxycarbonyloxy,
heterocyclylalkoxycarbonyloxy,
heterocyclylalkenyloxycarbonyloxy,
heterocyclylalkynyloxycarbonyloxy,
alkoxycarbonylamino, alkenyloxycarbonylamino,
alkynyloxycarbonyl-N-alkylamino,
cycloalkoxycarbonyl-N-alkylamino,
cycloalkylalkoxycarbonyl-N-alkylamino,
cycloalkylalkenyloxycarbonyl-N-alkylamino,
cycloalkylalkynyloxycarbonyl-N-alkylamino,
cycloalkenyloxycarbonyl-N-alkylamino,
cycloalkenylalkoxycarbonyl-N-alkylamino,
cycloalkenylalkenyloxycarbonyl-N-alkyl-amino,
cycloalkenylalkynyloxycarbonyl-N-alkylamino,
aryloxycarbonyl-N-alkylamino, arylalkoxycarbonyl-
N-alkylamino, arylalkenyloxycarbonyl-N-alkylamino,
aryl-alkynyoxycarbonyl-N-alkylamino,
heteroarylalkoxycarbonyl-N-alkylamino,
heteroarylalkenyloxycarbonyl-N-alkylamino,
N-alkylheteroarylalkynyloxycarbonyl-N-alkylamino,
N-alkylheterocyclylalkoxycarbonyl-N-alkylamino,
heterocyclylalkenyloxycarbonylamino,
heterocyclylalkynyloxycarbonyl-N-alkylamino,
formyl, haloalkoxy, haloalkenyloxy, haloalkynyloxy,
haloalkylthio, haloalkenylthio, haloalkynylthio,
haloalkylamino, haloalkenylamino, haloalkynylamino,
haloalkylsulfonyl, haloalkenylsulfonyl,
haloalkynylsulfonyl, haloalkylsulfinyl,
haloalkenylsulfinyl, haloalkynylsulfinyl,
haloalkylcarbonyl, haloalkenylcarbonyl,
haloalkynylcarbonyl, haloalkoxycarbonyl,
haloalkenyloxycarbonyl, haloalkynyloxycarbonyl,
haloalkylaminocarbonyl, haloalkenylaminocarbonyl,
haloalkynylaminocarbonyl, haloalkylcarbonylamino,
haloalkenylcarbonylamino,
haloalkynylcarbonylamino, haloalkoxycarbonylamino,
haloalkenyloxycarbonylamino,
haloalkynyloxycarbonylamino, haloalkylcarbonyloxy,
haloalkenylcarbonyloxy, haloalkynylcarbonyloxy,
haloalkoxycarbonyloxy, haloalkenyloxycarbonyloxy,
haloalkynyloxycarbonyloxy,
haloalkylaminocarbonylamino,
haloalkenylaminocarbonylamino,
haloalkynylaminocarbonylamino, cyano, nitro,
$—P(=O)R^8R^9$, $—P(=O)OR^{10}R^8$, $—P(=O)OR^{10}OR^{11}$, 2-tetrahydrofuranyloxymethyl,
3-tetrahydrofuranyloxymethyl,
2-tetrahydrothienyloxymethyl, 3-tetrahydrothienyl-
oxymethyl, 2-tetrahydropyranyloxymethyl, it being
possible for the radicals cycloalkyl, cycloalkenyl, aryl,
tetrahydrofuranyl, tetrahydrothienyl,
tetrahydropyranyloxymethyl, heteroaryl and heterocy-
clyl to be optionally mono- or polysubstituted, identi-
cally or differently, by $R^2$, or one of the groups —O—
$(CH_2)_m$—O—$(CH_2)_n$—$R^{2a}$, —O—$CH_2$—S—$(O)_p$—
$R^{13}$, —CONHN H—$(CH_2)_n$-alkyl and —CONHNH—
$(CH_2)_n$-aryl;

$R^{2a}$ is cycloalkyl, cycloalkenyl, cycloalkylalkyl,
cycloalkylalkenyl, cycloalkylalkynyl,
cycloalkenylalkyl, cycloalkenylalkyl, aryl, arylalkyl,
arylalkenyl, arylalkynyl, heteroaryl, heteroarylalkyl,
heteroarylalkenyl, heteroarylalkynyl, heterocyclyl,
heterocyclylalkyl, heterocyclylalkenyl,
heterocyclylalkynyl, hydroxyl, alkoxy, alkenyloxy,
alkynyloxy, cycloalkoxy, cycloalkakoxy,
cycloalkylaikenyloxy, cycloalkylalkynyloxy,
cycloalkenyloxy, cycloalkenylalkoxy,
cycloalkenylalkenyloxy, cycloalkenylalkynyloxy,
aryloxy, arylalkoxy, arylalkenyloxy, arylalkynylaoxy,
heteroaryloxy, heteroarylalkoxy, heteroarylalkenyloxy,
heteroarylalkynyloxy, heterocyclyloxy,
heterocyclylalkoxy, heterocyclylalkenyloxy,
heterocyclylalkynyloxy, thio, alkylthio, alkenylthio,
alkynylthio, cycloalkylthio, cycloalkylalkylthio,
cycloalkylalkenylthio, cycloalkylalkynylthio,
cycloalkenylthio, cycloalkenylalkylthio,
cycloalkenylalkenylthio, cycloalkenylalkynylthio,
arylthio, arylalkylthio, arylalkenylthio, arylalkynylthio,
heteroarylthio, heteroarylalkylthio,
heteroarylalkenylthio, heteroarylalkynylthio,
heterocyclylthio, heterocyclylalkylthio,
heterocyclylalkenylthio, heterocyclylalkynylthio,
amino, optionally substituted mono- or dialkylamino,
optionally substituted mono- or diarylamino, optionally
substituted mono- or diheteroarylamino, optionally
substituted N-alkyl-N-arylamino, optionally substi-
tuted N-alkyl-N-heteroarylamino, alkenylamino,
alkynylamino, cycloalkylamino, cycloalkenylamino,
heterocyclylalkylamino, heterocyclylalkenylamino,
alkylsulfonyl, alkenylsulfonyl, alkynylsulfonyl,
cycloalkylsulfonyl, cycloalkylalkylsulfonyl,
cycloalkylalkenylsulfonyl, cycloalkylalkynylsulfonyl,
cycloalkenylsulfonyl, cycloalkenylalkylsulfonyl,
cycloalkenylalkenylsulfonyl,
cycloalkenylalkynylsulfonyl, arylsulfonyl,
arylalkylsulfonyl, arylalkenylsulfonyl,
arylalkynylsulfonyl, heteroarylsulfonyl,
heteroarylalkylsulfonyl, heteroarylalkenylsulfonyl,
heteroarylalkynylsulfonyl, heterocyclylsulfonyl,
heterocyclylalkylsulfonyl,
heterocyclylalkenylsulfonyl,
heterocyclylalkynylsulfonyl, alkylsulfinyl,
alkenylsulfinyl, alkynylsulfinyl, cycloalkylsulfinyl,
cycloalkylalkylsulfinyl, cycloalkylalkenylsulfinyl,
cycloalkylalkynylsulfinyl, cycloalkenylsulfinyl,
cycloalkenylalkylsulfinyl, cycloalkenylalkenylsulfinyl,
cycloalkenylalkynylsulfinyl, arylsulfinyl,
arylalkylsulfinyl, arylalkenylsulfinyl,
arylalkynylsulfinyl, heteroarylsulfinyl,
heteroarylalkylsulfinyl, heteroarylalkenylsulfinyl,
heteroarylalkynylsulfinyl, heterocyclylsulfinyl, heterocyclylalkylsulfinyl, heterocyclylalkenylsulfinyl, heterocyclylalkynylsulfinyl, aminosulfonyl, optionally substituted mono- or dialkylaminosulfonyl, optionally substituted mono- or diarylaminosulfonyl, optionally substituted mono- or diheteroarylaminosulfonyl, optionally substituted N-alkyl-N-arylaminosulfonyl, optionally substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, cycloalkenylsulfonyloxy, cycloalkenylalkylsulfonyloxy, cycloalkenylalkenylsulfonyloxy, cycloalkenylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfonylamino, cycloalkylalkenylsulfonylamino, cycloalkylalkynylsulfonylamino, cycloalkenylalkylsulfonylamino, cycloalkenyialkenylsulfonylamino, cycloalkenylalkynylsulfonylamino, arylsulfonylamino, arylalkylsulfonylamino, arylalkenylsulfonylamino, arylalkynylsulfonylamino, heteroarylsulfonylamino, heteroarylalkylsulfonylamino, heteroarylalkenylsulfonylamino, heteroarylalkynylsulfonylamino, dialkylsulfonyl-N-alkylamino, alkenylsulfonyl-N-alkylamino, alkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, cycloalkenylsulfonyl-N-alkylamino, cycloalkenylalkylsulfonyl-N-alkylamino, cycloalkenylalkenylsulfonyl-N-alkylamino, cycloalkenylalkynylsulfonyl-N-alkylamino, arylsulfonyl-N-alkylamino, heteroarylsulfonyl-N-alkylamino, arylalkylsulfonyl-N-alkylamino, heteroarylalkylsulfonyl-N-alkylamino, arylalkenylsulfonyl-N-alkylamino, heteroarylalkenylsulfonyl-N-alkylamino, arylalkynylsulfonyl-N-alkylamino, heteroarylalkynylsulfonyl-N-alkylamino, heterocyclylsulfonyl-N-alkylamino, heterocyclylalkylsulfonyl-N-alkylamino, heterocyclylalkenylsulfonyl-N-alkylamino, heterocyclylalkynylsulfonyl-N-alkylamino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, cycloalkenylcarbonyl, cycloalkenylalkylcarbonyl, cycloalkenylalkenylcarbonyl, cycloalkenylalkynylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, heterocyclylcarbonyl, heterocyclylalkyl, heterocyclylalkenyl, heterocyclylalkynyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, cycoalkenyloxycarbonyl, cycloalkenylalkoxycarbonyl, cycloalkenylalkenyloxycarbonyl, cycloalkenylalkynyloxy carbonyl, aryloxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, alkylcarbonyloxy, alkenylcarbonyloxy, alkynylcarbonyloxy, cycloalkylcarbonyloxy, cycloalkylalkylcarbonyloxy, cycloalkylalkenylcarbonyloxy, cycloalkylalkynylcarbonyloxy, cycloalkenylcarbonyloxy, cycloalkenylalkylcarbonyloxy, cycloalkenylalkenylcarbonyloxy, cycloalkenylalkynylcarbonyloxy, arylcarbonyloxy, arylalkylcarbonyloxy, arylalkenylcarbonyloxy, arylalkynylcarbonyloxy, heteroarylcarbonyloxy, heteroarylalkylcarbonyloxy, heteroarylalkenylcarbonyloxy, heteroarylalkynylcarbonyloxy, heterocyclylcarbonyloxy, heterocyclylalkylcarbonyloxy, heterocyclylalkenylcarbonyloxy, heterocyclylalkynylcarbonyloxy, aminocarbonyl, optionally substituted mono- or dialkylaminocarbonyl, optionally substituted mono- or diarylaminocarbonyl, optionally substituted mono- or diheteroarylaminocarbonyl, optionally substituted N-alkyl-N-arylaminocarbonyl, optionally substituted N-alkyl-N-heteroarylaminocarbonyl, optionally substituted mono- or diheteroarylaminocarbonyloxy, optionally substituted N-alkyl-N-arylaminocarbonyloxy, optionally substituted N-alkyl-N-heteroarylaminocarbonyloxy, aminocarbonylamino, optionally substituted mono- or dialkylaminocarbonylamino, optionally substituted mono- or diarylaminocarbonylamino, optionally substituted mono- or diheteroarylaminocarbonylamino, optionally substituted N-alkyl-N-arylaminocarbonylamino, optionally substituted N-alkyl-N-heteroarylaminocarbonylamino, optionally substituted mono- or dialkylcarbonylamino, optionally substituted mono- or diarylcarbonylamino, optionally substituted mono- or diheteroarylcarbonylamino, optionally substituted alkylcarbonyl-N-arylamino, optionally substituted arylcarbonyl-N-alkylamino, optionally substituted alkylcarbonyl-N-heteroarylamino, optionally substituted heteroarylcarbonyl-N-alkylamino, alkoxycarbonyloxy, alkenyloxycarbonyloxy, alkynyloxycarbonyloxy, cycloalkoxycarbonyloxy, cycloalkylalkoxycarbonyloxy, cycloalkylalkenyloxycarbonyloxy, cycloalkylalkynyloxycarbonyloxy, cycloalkenyloxycarbonyloxy, cycloalkenylalkoxycarbonyloxy, cycloalkenylalkenyloxycarbonyloxy, cycloalkenylalkynyloxycarbonyloxy, aryloxycarbonyloxy, arylalkoxycarbonyloxy, arylalkenyloxyalycarbonyloxy, arylalkynyloxycarbonyloxy, heteroaryloxycarbonyloxy, heteroarylalkoxycarbonyloxy, heteroarylalkenyloxycarbonyloxy, heteroarylalkynyloxycarbonyloxy, heterocyclyloxycarbonyloxy, heterocyclylalkoxycarbonyloxy, heterocyclylalkenyloxycarbonyloxy, heterocyclylalkynyloxycarbonyloxy, alkoxycarbonylamino, alkenyloxycarbonylamino, alkynyloxycarbonylamino, cycloalkoxycarbonyloamino, cycloalkylalkoxycarbonyloamino, cycloalkylalkenyloxycarbonylamino, cycloalkylalkynyloxycarbonylamino, cycloalkenyloxycarbonylamino, cycloalkenylalkoxycarbonylamino, cycloalkenylalkenyloxycarbonylamino, cycloalkenylalkynyloxycarbonylamino, aryloxycarbonylamino, arylalkoxycarbonylamino, arylalkenyloxycarbonylamino, arylalkynyloxycarbonylamino, heteroaryloxycarbonylamino, heteroarylalkoxycarbonylamino, heteroarylalkenyloxycarbonylamino, heteroarylalkynyloxycarbonylamino, heterocyclyloxycarbonylamino, heterocyclylalkoxycarbonylamino, heterocyclylalkenyloxycarbonylamino, heterocyclylalkynyloxycarbonylamino, alkoxycarbonylamino, alkenyloxycarbonylamino, alkynyloxycarbonylamino, cycloalkoxycarbonylamino, cycloalkylalkoxycarbonylamino, N-alkylcycloalkylalkenyloxycarbonylamino, cycloalkylalkynyloxycarbonylamino, cycloalkenyloxycarbonylamino, cycloalkenylalkoxycarbonylamino, cycloalkenylalkenyloxycarbonylamino, cycloalkenylalkynyloxycarbonylamino, aryloxycarbonylamino, arylalkoxycarbonylamino, arylalkenyloxycarbonylamino, arylalkynyloxycarbonylamino, heteroarylalkoxycarbonylamino, heteroarylalkenyloxycarbonylamino, heteroarylalkynyloxycarbonylamino, heterocyclylalkoxycarbonylamino, heterocyclylalkenyloxycarbonylamino, heterocyclylalkynyloxycarbonylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino, haloalkylaminocarbonylamino, haloalkenylaminocarbonylamino, haloalkynylaminocarbonylamino, cyano, nitro or one of the groups —P(=O)$R^8R^9$, —P(=O)$OR^{10}R^8$, —P(=O)$OR^{10}OR^{11}$, —CH=N—NH—$(CH_2)_n$-alkyl, —CH=N—NH—$(CH_2)_n$-aryl, —CH=N—O—$(CH_2)_n$-alkyl, —CH=N—O—$(CH_2)_n$-aryl, —O—$(CH_2)_m$—O—$(CH_2)_n$-alkyl, —CONHNH—$(CH_2)_n$-alkyl and —CONHNH—$(CH_2)_n$-aryl;

$R^2$, $R^3$, $R^4$ and $R^5$ independently of one another are $R^{2a}$, hydrogen, alkyl, alkenyl or alkynyl;

$R^8$ and $R^9$ independently of one another are alkyl, alkenyl, alkynyl, haloalkyl, haloalkenyl, haloalkynyl, optionally substituted aryl or optionally substituted arylalkyl;

$R^{10}$ und $R^{11}$ independently of one another are hydrogen or $R^8$, or $R^{10}$ and $R^{11}$, together form a $C_2$–$C_5$-alkylene chain;

$R^{13}$ is alkyl, alkenyl, alkynyl, haloalkyl, haloalkenyl, haloalkynyl, or phenyl optionally substituted by one or more, identical or different radicals from the group consisting of halogen, alkyl, haloalkyl and nitro;

m is 1, 2 or 3;

n is 0, 1, 2 or 3 and p is 0, 1 or 2.

Preferred compounds of the formula (I) are those in which $R^1$ is cycloalkyl, cycloalkenyl, aryl, cycloalkoxy, cycloalkylalkoxy, cycloalkylalkenyloxy, cycloalkylalkynyloxy, cycloalkenyloxy, cycloalkenylalkoxy, cycloalkenylalkenyloxy, cycloalkenylalkynyloxy, aryloxy, arylalkoxy, arylalkenyloxy, arylalkynyloxy, cycloalkylthio, cycloalkylalkylthio, cycloalkylalkenylthio, cycloalkylalkynylthio, cycloalkenylthio, cycloalkenylalkylthio, cycloalkenylalkenylthio, cycloalkenylalkynylthio, arylthio, arylalkylthio, arylalkenylthio, arylalkynylthio, cycloalkylsulfonyl, cycloalkylalkylsulfonyl, cycloalkylalkenylsulfonyl, cycloalkylalkynylsulfonyl, cycloalkenylsulfonyl, cycloalkenylalkylsulfonyl, cycloalkenylalkenylsulfonyl, cycloalkenylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, cycloalkylsulfinyl, cycloalkylalkylsulfinyl, cycloalkylalkenylsulfinyl, cycloalkylalkynylsulfinyl, cycloalkenylsulfinyl, cycloalkenylalkylsulfinyl, cycloalkenylalkenylsulfinyl, cycloalkenylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, heterocyclylalkylsulfinyl, heterocyclylalkenylsulfinyl, heterocyclylalkynylsulfinyl, aminosulfonyl, optionally substituted mono- or dialkylaminosulfonyl, optionally substituted mono- or diarylaminosulfonyl, optionally substituted mono- or diheteroarylaminosulfonyl, optionally substituted N-alkyl-N-arylaminosulfonyl, optionally substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, cycloalkenylsulfonyloxy, cycloalkenylalkylsulfonyloxy, cycloalkenylalkenylsulfonyloxy, cycloalkenylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfonylamino, cycloalkylalkenylsulfonylamino, cycloalkylalkynylsulfonylamino, cycloalkenylsulfonylamino, cycloalkenylalkylsulfonylamino, cycloalkenylalkenylsulfonylamino, cycloalkenylalkynylsulfonylamino, arylsulfonylamino, arylalkylsulfonylamino, arylalkenylsulfonylamino, arylalkynylsulfonylamino, heteroarylsulfonylamino, heteroarylalkylsulfonylamino, heteroarylalkenylsulfonylamino, heteroarylalkynylsulfonylamino, alkylsulfonyl-N-alkylamino, alkenylsulfonyl-N-alkylamino, alkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, cycloalkenylsulfonyl-N-alkylamino, cycloalkenylalkylsulfonyl-N-alkylamino, cycloalkenylalkenylsulfonyl-N-alkylamino, cycloalkenylalkynylsulfonyl-N-alkylamino, arylsulfonyl-N-alkylamino, heteroarylsulfonyl-N-alkylamino, arylalkylsulfonyl-N-alkylamino, heteroarylalkylsulfonyl-N-alkylamino, arylalkenylsulfonyl-N-alkylamino, heteroarylalkenylsulfonyl-N-alkylamino, arylalkynylsulfonyl-N-alkylamino, heteroarylalkynylsulfonyl-N-alkylamino, heterocyclylsulfonyl-N-alkylamino, heterocyclylalkylsulfonyl-N-alkylamino, heterocyclylalkenylsulfonyl-N-alkylamino, heterocyclylalkynylsulfonyl-N-alkylamino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, cycloalkenylcarbonyl, cycloalkenylalkylcarbonyl, cycloalkenylalkenylcarbonyl, cycloalkenylalkynylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, heterocyclylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, cycloalkenyloxycarbonyl, cycloalkenylalkoxycarbonyl, cycloalkenylalkenyloxycarbonyl, cycloalkenylalkynyloxycarbonyl, aryloxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, aminocarbonyl, optionally substituted mono- or dialkylaminocarbonyl, optionally substituted mono- or diarylaminocarbonyl, optionally substituted mono- or diheteroarylaminocarbonyl, optionally substituted N-alkyl-N-arylaminocarbonyl, optionally substituted N-alkyl-N-heteroarylaminocarbonyl, optionally substituted mono- or dialkylcarbonylamino, optionally substituted mono- or diarylcarbonylamino, optionally substituted mono- or diheteroarylcarbonylamino, optionally substituted alkylcarbonyl-N-arylamino, optionally substituted arylcarbonyl-N-alkylamino, optionally substituted alkylcarbonyl-N-heteroarylamino, optionally substituted heteroarylcarbonyl-N-alkylamino, formyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkylcarbonylamino, haloalkenylcarbonylamino, haloalkynylcarbonylamino, haloalkoxycarbonylamino, haloalkenyloxycarbonylamino, haloalkynyloxycarbonylamino, haloalkylcarbonyloxy, haloalkenylcarbonyloxy, haloalkynylcarbonyloxy, haloalkoxycarbonyloxy, haloalkenyloxycarbonyloxy, haloalkynyloxycarbonyloxy, haloalkylaminocarbonylamino, haloalkenylaminocarbonylamino, haloalkynylaminocarbonylamino, cyano, nitro, —P(=O)R$^8$R$^9$, —P(=O)OR$^{10}$R$^8$, —P(=O)OR$^{10}$OR$^{11}$, 2-tetrahydrofuranyloxymethyl, 3-tetrahydrofuranyloxymethyl, 2-tetrahydrothienyloxymethyl, 3-tetrahydrothienyloxymethyl, 2-tetrahydropyranyloxymethyl, it being possible for the radicals cycloalkyl, cycloalkenyl, aryl, tetrahydrofuranyl, tetrahydrothienyl, tetrahydropyranyl, heteroaryl and heterocyclyl to be optionally mono- or polysubstituted, identically or differently, by R$^2$, or one of the groups —O—(CH$_2$)$_m$—O—(CH$_2$)$_n$—R$^{2a}$, —O—CH$_2$—S—(O)$_p$—R$^{13}$, —CONHNH—(CH$_2$)$_n$-alkyl and —CONHNH—(CH$_2$)$_n$-aryl, and R$^{2a}$ is (C$_1$–C$_6$)-alkoxy, (C$_2$–C$_6$)-alkenyloxy, (C$_3$–C$_6$)-alkynyloxy, halo-(C$_1$–C$_6$)-alkoxy, halo-(C$_2$–C$_6$)-alkenyloxy, halo-(C$_3$–C$_6$)-alkynyloxy or phenyl which is optionally mono- or polysubstituted by halogen, cyano, nitro, (C$_1$–C$_6$)-alkyl, (C$_1$–C$_6$)-alkoxy, halo-(C$_1$–C$_6$)-alkyl or halo-(C$_1$–C$_6$)-alkoxy.

Preferred compounds of the formula (I) are likewise those in which

R$^2$, R$^3$, R$^4$ and R$^5$ independently of one another are hydrogen, alkyl, alkenyl, alkynyl, cycloalkyl, cycloalkenyl, cycloalkylalkyl, aryl, arylalkyl, heteroaryl, heteroarylalkyl, heterocyclyl, heterocyclylalkyl, hydroxyl, alkoxy, cycloalkoxy, aryloxy, heteroaryloxy, heterocyclyloxy, alkylthio, arylthio, heteroarylthio, heterocyclylthio, heterocyclylalkylthio, amino, mono- or dialkylamino, mono- or diarylamino, N-alkyl-N-arylamino, cycloalkylamino, alkylsulfonyl, arylsulfonyl, alkylsulfinyl, aminosulfonyl, mono- or dialkylaminosulfonyl, mono- or diarylaminosulfonyl, N-alkyl-N-arylaminosulfonyl, N-alkyl-N-heteroarylaminosulfonyl, alkylsulfonylamino, cycloalkylsulfonylamino, arylsulfonylamino, heteroarylsulfonylamino, cycloalkylsulfonyl-N-alkylamino, arylsulfonyl-N-alkylamino, heteroarylsulfonyl-N-alkylamino, heterocyclylsulfonyl-N-alkylamino, alkylcarbonyl, cycloalkylcarbonyl, arylcarbonyl, arylalkylcarbonyl, heteroarylcarbonyl, heterocyclylcarbonyl, carboxyl, alkoxycarbonyl, aryloxycarbonyl, arylalkoxycarbonyl, alkylcarbonyloxy, arylcarbonyloxy, arylalkylcarbonyloxy, aminocarbonyl, mono- or dialkylaminocarbonyl, N-alkyl-N-arylaminocarbonyl, N-alkyl-N-heteroarylaminocarbonyl, N-alkyl-N-arylaminocarbonyloxy, aminocarbonylamino, mono- or dialkylaminocarbonylamino, mono- or diarylaminocarbonylamino, mono- or diheteroarylaminocarbonylamino, N-alkyl-N-arylaminocarbonylamino, mono- or dialkylcarbonylamino, mono- or diarylcarbonylamino, alkylcarbonyl-N-arylamino, arylcarbonyl-N-alkylamino, alkoxycarbonyloxy, cycloalkoxycarbonyloxy, aryloxycarbonyloxy, arylalkoxycarbonyloxy, alkoxycarbonylamino, cycloalkoxycarbonylamino, aryloxycarbonylamino, alkoxycarbonyl-N-alkylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkylaminocarbonylamino, cyano, nitro, arylalkoxyalkoxy or alkoxyalkoxyalkoxy;

$R^6$ is $OR^{12}$, alkylthio, alkylsulfonyl, cyano, cyanato, thiocyanato or halogen;

$R^7$ is hydrogen, alkyl, cycloalkyl, alkoxy, alkoxyalkyl, alkylcarbonyl, alkoxycarbonyl, alkylthio or phenyl, or two radicals $R^7$ bonded to a common carbon atom form a chain from the group consisting of $OCH_2CH_2O$ and $OCH_2CH_2CH_2O$, this optionally being substituted by one to four methyl groups, or two radicals $R^7$ bonded to directly adjacent carbon atoms form a bond or, with the carbon atoms carrying them, form a 3- to 6-membered ring optionally substituted by one or more, identical or different radicals from the group consisting of halogen, alkyl, alkylthio and alkoxy;

$R^8$ and $R^9$ independently of one another are alkyl, alkenyl, alkynyl, haloalkyl, optionally substituted aryl or optionally substituted arylalkyl;

$R^{12}$ is hydrogen, haloalkyl, alkoxyalkyl, formyl, alkylcarbonyl, alkoxycarbonyl, alkylsulfonyl, haloalkylsulfonyl, benzoyl or phenylsulfonyl, the two last-mentioned groups optionally being substituted by one or more, identical or different radicals from the group consisting of alkyl, haloalkyl, alkoxy, haloalkoxy, halogen, cyano and nitro;

L is a $C_1$–$C_6$-alkylene chain which is optionally substituted by one to four identical or different radicals $R^2$;

Y is a divalent unit from the group consisting of O, N—H, N-alkyl, $CHR^7$ and $C(R^7)_2$;

Z is a direct bond, a divalent unit from the group consisting of O, S, $SO_2$, N-alkyl, $CHR^7$ or $C(R^7)_2$ and w is 0, 1, 2 or 3.

Particularly preferred compounds of the formula (I) are those in which $R^1$ is halo-$(C_1$–$C_6)$-alkoxy, halo-$(C_2$–$C_6)$-alkenyloxy, halo-$(C_3$–$C_6)$-alkynyloxy, halo-$(C_1$–$C_6)$-alkylthio, halo-$(C_2$–$C_6)$-alkenylthio, halo-$(C_3$–$C_6)$-alkynylthio, halo-$(C_1$–$C_6)$-alkylamino, halo-$(C_2$–$C_6)$-alkenylamino, halo-$(C_3$–$C_6)$-alkynylamino, halo-$(C_1$–$C_6)$-alkylsulfonyl, halo-$(C_2$–$C_6)$-alkenylsulfonyl, halo-$(C_3$–$C_6)$-alkynylsulfonyl, halo-$(C_1$–$C_6)$-alkylsulfinyl, halo-$(C_2$–$C_6)$-alkenylsulfinyl, halo-$(C_3$–$C_6)$-alkynylsulfinyl, halo-$(C_1$–$C_6)$-alkylcarbonyl, halo-$(C_2$–$C_6)$-alkenylcarbonyl, halo-$(C_3$–$C_6)$-alkynylcarbonyl, halo-$(C_1$–$C_6)$-alkoxycarbonyl, halo-$(C_2$–$C_6)$-alkenyloxycarbonyl, halo-$(C_3$–$C_6)$-alkynyloxycarbonyl, halo-$(C_1$–$C_6)$-alkylaminocarbonyl, halo-$(C_2$–$C_6)$-alkenylaminocarbonyl, halo-$(C_3$–$C_6)$-alkynylaminocarbonyl, halo-$(C_1$–$C_6)$-alkylcarbonylamino, halo-$(C_2$–$C_6)$-alkenylcarbonylamino, halo-$(C_3$–$C_6)$-alkynylcarbonylamino, halo-$(C_1$–$C_6)$-alkoxycarbonylamino, halo-$(C_2$–$C_6)$-alkenyloxycarbonylamino, halo-$(C_3$–$C_6)$-alkynyloxycarbonylamino, halo-$(C_1$–$C_6)$-alkylcarbonyloxy, halo-$(C_2$–$C_6)$-alkenylcarbonyloxy, halo-$(C_3$–$C_6)$-alkynylcarbonyloxy, halo-$(C_1$–$C_6)$-alkoxycarbonyloxy, halo-$(C_2$–$C_6)$-alkenyloxycarbonyloxy, halo-$(C_3$–$C_6)$-alkynyloxycarbonyloxy, halo-$(C_1$–$C_6)$-alkylaminocarbonylamino, halo-$(C_2$–$C_6)$-alkenylaminocarbonylamino, halo-$(C_3$–$C_6)$-alkynylaminocarbonylamino, —O—$(CH_2)_m$—O—$(CH_2)_n$—$R^{2a}$, —P(=O)$R^8R^9$, —P(=O)$OR^{10}R^8$, —P(=O)$OR^{10}OR^{11}$, 2-tetrahydrofuranyloxymethyl, 3-tetrahydrofuranyloxymethyl, 2-tetrahydrothienyloxymethyl, 3-tetrahydrothienyloxymethyl, 2-tetrahydropyranoxymethyl, $C_3$–$C_6$-cyclo-$(C_1$–$C_6)$-alkyl, $C_3$–$C_6$-cyclo-$(C_2$–$C_6)$-alkenyl, $C_3$–$C_6$-cyclo-$(C_1$–$C_6)$-alkoxy, $C_3$–$C_6$-cyclo-$(C_1$–$C_6)$-alkyl-$(C_1$–$C_6)$-alkoxy, $C_3$–$C_6$-cyclo-$(C_1$–$C_6)$-alkyl-$(C_2$–$C_6)$-alkenyloxy, $C_3$–$C_6$-cyclo-$(C_1$–$C_6)$-alkyl-$(C_2$–$C_6)$-alkynyloxy, $C_3$–$C_6$-cycloalkenyloxy, $C_3$–$C_6$-cycloalkenyl-$(C_1$–$C_6)$-alkoxy, $C_3$–$C_6$-cycloalkenyl-$(C_2$–$C_6)$-alkenyloxy, $C_3$–$C_6$-cycloalkenyl-$(C_2$–$C_6)$-alkynyloxy, the last-mentioned 15 radicals optionally being substituted by one or more, identical or different radicals from the group consisting of hydrogen, $C_1$–$C_6$-alkyl, halo-$(C_1$–$C_6)$-alkyl, $C_1$–$C_6$-alkoxy, halo-$(C_1$–$C_6)$-alkoxy, $C_1$–$C_6$-alkylthio, halo-$(C_1$–$C_6)$-alkylthio, $C_1$–$C_6$-alkylsulfinyl, halo-$(C_1$–$C_6)$-alkylsulfinyl, $C_1$–$C_6$-alkylsulfonyl, halo-$(C_1$–$C_6)$- alkylsulfonyl, $C_1$–$C_6$-alkylcarbonylamino, $C_1$–$C_6$-alkylsulfonylamino, halogen, nitro and cyano.

Particularly preferred compounds of the formula (I) are likewise those in which $R^2$, $R^3$ and $R^4$ independently of one another are hydrogen, alkyl, alkenyl, alkynyl, cycloalkyl, cycloalkenyl, cycloalkylalkyl, hydroxyl, alkoxy, cycloalkoxy, alkylthio, amino, mono- or dialkylamino, cycloalkylamino, alkylsulfonyl, alkylsulfinyl, aminosulfonyl, mono- or dialkylaminosulfonyl, alkylsulfonylamino, cycloalkylsulfonylamino, alkylcarbonyl, cycloalkylcarbonyl, alkoxycarbonyl, alkylcarbonyloxy, aminocarbonyl, mono- or dialkylaminocarbonyl, alkoxycarbonyloxy, cycloalkoxycarbonyloxy, alkoxycarbonylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkoxycarbonyl, haloalkenyloxycarbonyl, haloalkynyloxycarbonyl, haloalkylaminocarbonyl, cyano, nitro, $R^5$ is hydrogen $R^6$ is $OR^{12}$ or $C_1$–$C_6$-alkylthio;

$R^7$ is hydrogen, $C_1$–$C_6$-alkyl, $C_3$–$C_6$-cycloalkyl, $C_1$–$C_6$-alkoxy, $C_1$–$C_6$-alkylthio or phenyl;

$R^8$ and $R^9$ independently of one another are $C_1$–$C_6$-alkyl, $C_2$–$C_6$-alkenyl, $C_2$–$C_6$-alkynyl, halo-$C_1$–$C_6$-alkyl, aryl or benzyl;

$R^{12}$ is hydrogen, halo-$C_1$–$C_6$-alkyl, $C_1$–$C_6$-alkylcarbonyl, $C_1$–$C_6$-alkoxycarbonyl, $C_1$–$C_6$-alkylsulfonyl, benzoyl or phenylsulfonyl, the two last-mentioned groups optionally being substituted by one or more, identical or different radicals from the group consisting of $C_1$–$C_6$-alkyl, halo-$C_1$–$C_6$-alkyl, $C_1$–$C_6$-alkoxy, halo-$C_1$–$C_6$-alkoxy, halogen, cyano and nitro;

L is a $C_1$–$C_3$-alkylene chain which is optionally substituted by one to 4 identical or different radicals $R^2$ and Y is a divalent unit from the group consisting of N-alkyl, $CHR^7$ and $C(R^7)_2$, and Z is a direct bond, a divalent unit from the group consisting of $CHR^7$ and $C(R^7)_2$.

Very particularly preferred compounds of the formula (I) are those in which $R^1$ is halo-($C_1$–$C_6$)-alkoxy, halo-($C_2$–$C_6$)-alkenyloxy, halo-($C_3$–$C_6$)-alkynyloxy, halo-($C_1$–$C_6$)-alkylthio, halo-($C_2$–$C_6$)-alkenylthio, halo-($C_3$–$C_6$)-alkynylthio, halo-($C_1$–$C_6$)-alkylamino, halo-($C_2$–$C_6$)-alkenylamino, halo-($C_3$–$C_6$)-alkynylamino, halo-($C_1$–$C_6$)-alkylsulfonyl, halo-($C_2$–$C_6$)-alkenylsulfonyl, halo-($C_3$–$C_6$)-alkynylsulfonyl, halo-($C_1$–$C_6$)-alkylsulfinyl, halo-($C_2$–$C_6$)-alkenylsulfinyl, halo-($C_3$–$C_6$)-alkynylsulfinyl, halo-($C_1$–$C_6$)-alkylcarbonyl, halo-($C_2$–$C_6$)-alkenylcarbonyl, halo-($C_3$–$C_6$)-alkynylcarbonyl, halo-($C_1$–$C_6$)-alkoxycarbonyl, halo-($C_2$–$C_6$)-alkenyloxycarbonyl, halo-($C_3$–$C_6$)-alkynyloxycarbonyl, halo-($C_1$–$C_6$)-alkylaminocarbonyl, halo-($C_2$–$C_6$)-alkenylaminocarbonyl, halo-($C_3$–$C_6$)-alkynylaminocarbonyl, halo-($C_1$–$C_6$)-alkylcarbonylamino, halo-($C_2$–$C_6$)-alkenylcarbonylamino, halo-($C_3$–$C_6$)-alkynylcarbonylamino, halo-($C_1$–$C_6$)-alkoxycarbonylamino, halo-($C_2$–$C_6$)-alkenyloxycarbonylamino, halo-($C_3$–$C_6$)-alkynyloxycarbonylamino, halo-($C_1$–$C_6$)-alkylcarbonyloxy, halo-($C_2$–$C_6$)-alkenylcarbonyloxy, halo-($C_3$–$C_6$)-alkynylcarbonyloxy, halo-($C_1$–$C_6$)-alkoxycarbonyloxy, halo-($C_2$–$C_6$)-alkenyloxycarbonyloxy, halo-($C_3$–$C_6$)-alkynyloxycarbonyloxy, halo-($C_1$–$C_6$)-alkylaminocarbonyloxy, halo-($C_2$–$C_6$)-alkenylaminocarbonyloxy, halo-($C_3$–$C_6$)-alkynylaminocarbonylamino, —O—$(CH_2)_m$—O—$(CH_2)_n$—$R^{2a}$;

$R^2$ and $R^3$ independently of one another are hydrogen, $C_1$–$C_6$-alkyl, halo-($C_1$–$C_6$)-alkyl, $C_1$–$C_6$-alkoxy, halo-($C_1$–$C_6$)-alkoxy, $C_1$–$C_6$-alkylthio, halo-($C_1$–$C_6$)-alkylthio, $C_1$–$C_6$-alkylsulfinyl, halo-($C_1$–$C_6$)-alkylsulfinyl, $C_1$–$C_6$-alkylsulfonyl, halo-($C_1$–$C_6$)-alkylsulfonyl, halogen, nitro and cyano;

$R^4$ is hydrogen;

$R^6$ is $OR^{12}$;

$R^7$ is hydrogen or $C_1$–$C_6$-alkyl;

$R^{12}$ is hydrogen, $C_1$–$C_6$-alkylsulfonyl, benzoyl, phenylsulfonyl, the two last-mentioned groups optionally being substituted by one or more, identical or different radicals from the group consisting of $C_1$–$C_6$-alkyl, halo-($C_1$–$C_6$)-alkyl, $C_1$–$C_6$-alkoxy, halo-($C_1$–$C_6$)-alkoxy, halogen, cyano and nitro;

L is $CH_2$ optionally substituted by one or two identical or different $C_1$–$C_6$-alkyl or $C_1$–$C_6$-alkoxy radicals;

Y and Z independently of one another are $CHR^7$ or $C(R^7)_2$;

v is 1 and w is 0, 1 or 2.

In all formulae mentioned below, the substituents and symbols, if not defined otherwise, have the same meaning as described under formula (I).

Depending on the meaning of the substituents, the compounds according to the invention can be prepared, for example, by one or more of the processes indicated in the following schemes.

Compounds of the formula (I) according to the invention are obtained by the reaction, indicated in scheme 1, of a compound of the formula (II) with a compound of the formula (III) in which R is hydroxyl, chlorine, bromine or cyano. For this, if R=hydroxyl, the compound of the formula (II) is reacted in the presence of dehydrating agents, such as DCC, or if R=chlorine or bromine, under base-catalyzed conditions and in the presence of a cyanide source, or if R=cyano, under base-catalyzed conditions directly with (III). These methods are described, for example, in EP-A 0 369 803 and EP-B 0 283 261.

Scheme 1

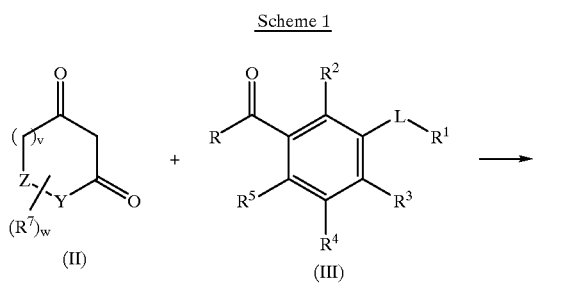

(II)  (III)

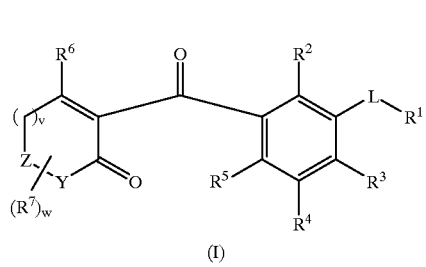

(I)

The dicarbonyl compounds of the formula (II) are either commercially obtainable or can be prepared according to known methods. Such methods are known, for example, from EP-A 0 283 261, *Tetrahedron Lett.* 32, 3063 (1991), *J. Org. Chem.* 42, 2718, (1977), *Helv. Chim. Acta.* 75, 2265 (1992), *Tetrahedron Lett.* 28, 551 (1987), *Tetrahedron Lett.* 32, 6011 (1991, *Chem. Lett.* 551, 1981, *Heterocycles* 26, 2611 (1987). Compounds of the abovementioned formula (III) can be prepared according to known methods from compounds of the formula (III) in which R is hydroxyl or alkoxy.

Compounds of the formula (III) in which $R^1$ is alkoxy can be prepared, for example, according to scheme 2 from compounds of the formula (IV) in which Hal is halogen.

Scheme 2

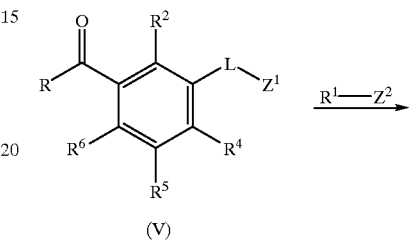

(IV)  (III)

2.1 Compounds of the formula (III) are obtainable by base-catalyzed reaction with compounds $R^1$—H, such as alcohols, thioalcohols, amides, amines, heteroaromatics, heterocycles. Such reactions are known, for example, from *J. C. Chem. Res., Synop.* 1994, 174, *Tetrahedron Lett.* 27, 279 (1986, *J. Org. Chem.* 55, 6037 (1990), *J. Org. Chem.* 54, 3757 (1989).

2.2 Compounds of the formula (III) are likewise obtainable by reaction with organolithium compounds of the formula $R^1$—Li. Such reactions are known, for example, from *Synth. Commun.* 18, 1035, (1988), *J. Org. Chem.* 46, 3132, (1981).

Compounds of the formula (III) are also obtainable according to scheme 3 by base-catalyzed reaction of a compound of the formula (V), in which $Z^1$ is OH, SH, NH-alkyl, NH-aryl or NH-heteroaryl, with compounds of the formula $R^1$—$Z^2$ which are commerically obtainable or can be prepared according to known methods, in which $Z^2$ is a leaving group, such as halogen, phenoxy or alkylsulfonyl. Such reactions are known, for example, from *Synthesis* 1980, 573, *Tetrahedron Lett.* 37, 4065 (1996).

Scheme 3

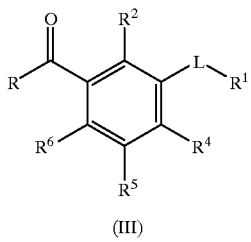

(V)

(III)

The reaction, indicated in scheme 4, of a compound of the formula (Ia) with a halogenating reagent, such as oxalyl chloride or oxalyl bromide, leads to compounds of the formula (Ib) according to the invention which, by reaction, if appropriate with base catalysis, with nucleophiles, such as alkali metal cyanides, alkali metal cyanates, alkali metal thiocyanates, alkylthioalcohols and thiophenols can be reacted to give further compounds of the formula (Ic) according to the invention, in which $R^6$ is alkylthio, haloalkylthio, alkenylthio, haloalkenylthio, alkynylthio, haloalkynylthio, cyano, cyanato, thiocyanato or $OR^{12}$. Such reactions are described, for example, in *Synthesis* 12, 1287 (1992). By reaction with an oxidizing reagent, such as peroxyacetic acid, hydrogen peroxide, m-chloroperoxybenzoic acid and potassium peroxymonosulfate, compounds of the formula (Ic) according to the invention are obtained in which $R^6$ is alkylsulfinyl, haloalkylsulfinyl, alkenylsulfinyl, haloalkenylsulfinyl, alkynylsulfinyl, haloalkynylsulfinyl, alkylsulfonyl, haloalkylsulfonyl, alkenylsulfonyl, haloalkenylsulfonyl, alkynylsulfonyl or haloalkynylsulfonyl. Such reactions are described, for example, in *J. Org. Chem.* 53, 532 (1988), *Tetrahedron Lett.* 21, 1287 (1981).

Scheme 4

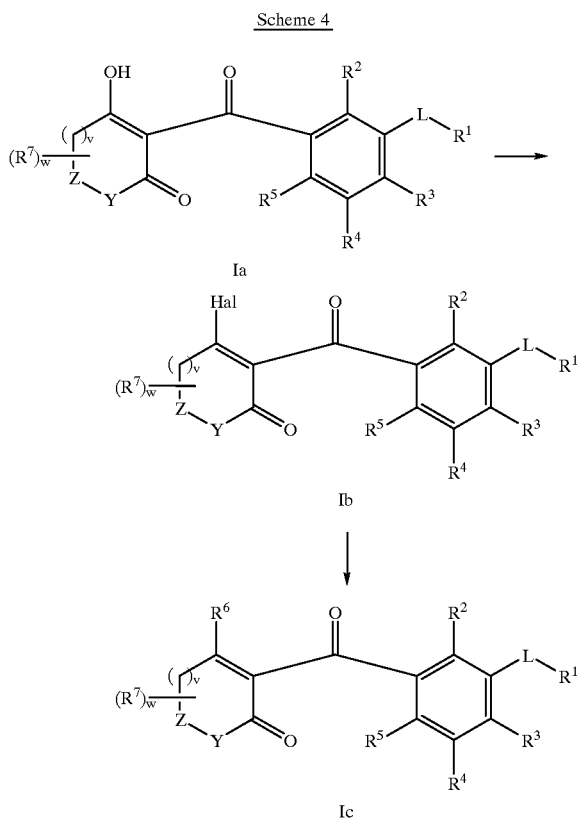

The compounds of the formula (I) according to the invention have an excellent herbicidal activity against a broad spectrum of economically important mono- and dicotyledonous harmful plants. The active substances also act efficiently on perennial weeds which produce shoots from rhizomes, root stocks or other perennial organs and are difficult to control. In this context, it is unimportant whether the substances are applied before sowing, preemergence or postemergence. Specifically, some representatives of the mono- and dicotyledonous weed flora which can be controlled by the compounds according to the invention may be mentioned by way of example, without a restriction to certain species being intended to take place as a result of the mention.

Amongst the monocotyledonous weed species, those on which the active substances act efficiently are, for example, Avena, Lolium, Alopecurus, Phalaris, Echinochloa, Digitaria, Setaria and Cyperus species from the annual group and, amongst the perennial species, Agropyron, Cynodon, Imperata and Sorghum and also perennial Cyperus species.

In the case of dicotyledonous weed species, the spectrum of action extends to species such as, for example, Galium, Viola, Veronica, Lamium, Stellaria, Amaranthus, Sinapis, Ipomoea, Matricaria, Abutilon and Sida amongst the annuals and Convolvulus, Cirsium, Rumex and Artemisia in the case of the perennial weeds. Harmful plants occurring under the specific cultivation conditions of rice, such as, for example, Echinochloa, Sagittaria, Alisma, Eleocharis, Scirpus and Cyperus, are also outstandingly well controlled by the active substances according to the invention. If the compounds according to the invention are applied to the soil surface before germination, then the weed seedlings are either prevented completely from emerging or the weeds grow until they have reached the cotyledon stage, but then their growth stops and they finally die completely after three to four weeks have elapsed. When the active substances are applied postemergence to the green parts of the plants, growth stops equally drastically a very short time after treatment and the weed plants remain at the stage of growth at the time of application, or they die completely after a certain time, so that in this manner competition by the weeds, which is harmful to the crop plants, is eliminated at a very early stage and in a sustained manner.

Although the compounds according to the invention have an excellent herbicidal activity against mono- and dicotyledonous weeds, crop plants of economically important crops such as, for example, wheat, barley, rye, rice, maize, sugar beet, cotton and soybeans, are damaged only to an insignificant extent or not at all. For these reasons, the present compounds are very highly suitable for the selective control of undesired vegetation in crops of agriculturally useful plants or in crops of ornamental plants.

On account of their herbicidal and plant growth-regulatory properties, the active substances can also be employed for the control of harmful plants in crops of known genetically modified plants or genetically modified plants yet to be developed. As a rule, the transgenic plants are distinguished by particularly advantageous properties, for example by resistances to certain pesticides, especially certain herbicides, resistances to plant diseases or pathogens of plant diseases such as certain insects or microorganisms such as fungi, bacteria or viruses. Other particular properties relate, for example, to the harvested material with respect to quantity, quality, storability, composition and specific constituents. Thus, transgenic plants having an increased starch content or where the quality of the starch is altered or those having a different fatty acid composition of the harvested material are known.

The compounds of the formula (I) according to the invention or their salts are preferably used in economically important transgenic crops of useful and ornamental plants, e.g. of cereals such as wheat, barley, rye, oats, millet, rice, cassava and corn or alternatively crops of sugar beet, cotton, soybeans, oilseed rape, potatoes, tomatoes, peas and other types of vegetables.

The compounds of the formula (I) can preferably be employed as herbicides in useful plant crops which are resistant or have been made genetically resistant to the phytotoxic effects of the herbicides.

Traditional ways of generating novel plants which have modified characteristics in comparison with existing plants consist, for example, in traditional breeding methods and the generation of mutants. Alternatively, novel plants with modified characteristics can be generated using genetic engineering procedures (see, for example, EP-A-0221044, EP-A-0131624). For example, a number of cases have been described of genetic engineering modifications of crop plants for the purpose of modifying the starch synthesized in the plants (e.g. WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylureas type (EP-A-0257993, U.S. Pat. No. 5,013,659), transgenic crop plants, for example cotton, with the capability of producing Bacillus thuringiensis toxins (Bt toxins) which make the plants resistant to certain pests (EP-A-0142924, EP-A-0193259), transgenic crop plants having a modified fatty acid composition Numerous molecular biology techniques using which novel transgenic plants having modified properties can be produced are known in principle; see, for example, Sambrook et al., 1989, Molecular Cloning, A Laboratory Manual, $2^{nd}$ Ed. Cold Spring Harbor Laboratory Press, Cold Spring Harbor, N.Y.; or Winnacker "Gene und Klone" [Genes and Clones], VCH Weinheim $2^{nd}$ Edition 1996 or Christou, "Trends in Plant Science" 1 (1996) 423–431).

For genetic engineering manipulations of this type, nucleic acid molecules can be introduced into plasmids which allow mutagenesis or a sequence modification by means of recombination of DNA sequences. With the aid of the abovementioned standard procedures, it is possible, for example, to perform base exchanges, to remove subsequences or to add natural or synthetic sequences. For the connection of the DNA fragments to one another, adaptors or linkers can be attached to the fragments.

For example, plant cells having a reduced activity of a gene product can be produced by the expression of at least one corresponding antisense RNA, a sense RNA to achieve a cosuppression effect or the expression of at least one appropriately constructed ribozyme which specifically cleaves transcripts of the abovementioned gene product.

For this, it is possible to use, on the one hand, DNA molecules which comprise the entire coding sequence of a gene product including flanking sequences which may be present, and also DNA molecules which only comprise parts of the coding sequence, where these parts must be long enough in order to bring about an antisense effect in the cells. The use of DNA sequences which have a high degree of homology to the coding sequences of a gene product, but are not completely identical, is also possible.

When nucleic acid molecules are expressed in plants, the synthesized protein can be localized in any desired compartment of the plant cell. However, in order to achieve localization in a certain compartment, it is possible, for example, to link the coding region with DNA sequences which guarantee localization in a certain compartment. Sequences of this type are known to the person skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated to give whole plants according to known techniques. In principle, the transgenic plants can be plants of any desired plant species, i.e. both monocotyledonous and dicotyledonous plants.

Transgenic plants are thus obtainable which have modified properties as a result of overexpression, suppression or inhibition of homologous (=natural) genes or gene sequences or expression of heterologous (=foreign) genes or gene sequences.

The compounds according to the invention can preferably be employed in transgenic crops which are resistant to herbicides from the group consisting of the sulfonylureas, glufosinate-ammonium or glyphosate-isopropylammonium and analogous active substances.

When the active substances according to the invention are used in transgenic crops, in addition to the effects against harmful plants to be observed in other crops, effects often occur which are specific for application in the particular transgenic crop, for example a modified or specifically widened spectrum of weeds which can be controlled, altered application rates which can be employed for application, preferably good combining ability with the herbicides to which the transgenic crop is resistant, and an effect on growth and yield of the transgenic crop plants.

The invention therefore also relates to the use of the compounds according to the invention as herbicides for controlling harmful plants in transgenic crop plants.

The substances according to the invention moreover have outstanding growth-regulatory properties in crop plants. They intervene in a regulatory manner in the plant's own metabolism and can thus be employed for specifically influencing plant constituents and for facilitating harvesting, such as, for example, by inducing desiccation and stunting of growth. In addition, they are also suitable for the general control and inhibition of undesired vegetative growth, without at the same time killing the plants. Inhibition of the vegetative growth plays a large role in the case of many mono- and dicotyledonous crops, since lodging can be reduced or completely prevented thereby.

The compounds according to the invention can be used in the customary preparations in the form of wettable powders, emulsifiable concentrates, sprayable solutions, dusting agents or granules. The invention therefore also relates to herbicidal and plant growth-regulating compositions which contain compounds of the formula (I).

The compounds of the formula (I) can be formulated in various ways, depending on what biological and/or chemicophysical parameters are prespecified. Examples of suitable formulation possibilities are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions on an oil or water basis, oil-miscible solutions, capsule suspensions (CS), dusting agents (DP), dressing agents, granules for broadcasting and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in: Winnacker-Küchler, "Chemische Technologie" [Chemical Technology], Volume 7, C. Hauser Verlag Munich, $4^{th}$ Edition 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries such as inert materials, surfactants, solvents and other additives are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1976; Winnacker-Küchler, "Chemische Technologie" [Chemical Technology], Volume 7, C. Hauser Verlag Munich, $4^{th}$ Edition 1986.

On the basis of these formulations, combinations with other pesticidally active substances such as, for example, insecticides, acaricides, herbicides, fungicides, and also with safeners, fertilizers and/or growth regulators can also be prepared, e.g. in the form of a finished formulation or as a tank mix.

Wettable powders are preparations which are uniformly dispersible in water and which, beside the active compound, also contain surfactants of ionic and/or nonionic type (wetting agents, dispersants), e.g. polyoxyethylated alkylphenols, polyoxethylated fatty alcohols, polyoxethylated fatty amines, fatty alcohol polyglycol ether sulfates, alkanesulfonates, alkylbenzenesulfonates, sodium lignosulfonates, sodium 2,2'-dinaphthylmethane-6,6'-disulfonates, sodium dibutyinaphthalenesulfonates or alternatively sodium oleoylmethyltaurates in addition to a diluent or inert substance. For preparation of the wettable powders, the herbicidal active substances are finely ground, for example, in customary equipment such as hammer mills, blowing mills and air-jet mills and simultaneously or subsequently mixed with the formulation auxiliaries.

Emulsifiable concentrates are prepared by dissolving the active substance in an organic solvent, e.g. butanol, cyclohexanone, dimethylformamide, xylene or alternatively relatively high-boiling aromatics or hydrocarbons or mixtures of the organic solvents with addition of one or more surfactants of ionic and/or nonionic type (emulsifiers). Examples of emulsifiers which can be used are: alkylarylsulfonic acid calcium salts such as Ca dodecylbenzenesulfonate or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters such as, for example, sorbitan fatty acid esters or polyoxyethylene sorbitan esters such as, for example, polyoxyethylene sorbitan fatty acid esters.

Dusting agents are obtained by grinding the active substance with finely divided solid substances, e.g. talc, natural clays, such as kaolin, bentonite and pyrophyllite, or diatomaceous earth.

Suspension concentrates can be water- or oil-based. They can be prepared, for example, by wet grinding by means of commercially available bead mills and, if appropriate, addition of surfactants, such as have already been mentioned, for example, above in the case of the other formulation types.

Emulsions, e.g. oil-in-water emulsions (EW), can be prepared, for example, by means of stirrers, colloid mills and/or static mixers using aqueous organic solvents and, if appropriate, surfactants, such as have already been mentioned, for example, above in the case of the other formulation types.

Granules can either be prepared by spraying the active substance onto adsorptive, granulated inert material or by applying active substance concentrates to the surface of carriers such as sand, kaolinites or of granulated inert material by means of binders, e.g. polyvinyl alcohol, sodium polyacrylates or alternatively mineral oils. Suitable active substances can also be granulated in the manner customary for the preparation of fertilizer granules—if desired as a mixture with fertilizers.

As a rule, water-dispersible granules are prepared by the customary processes such as spray-drying, fluidized bed granulation, disk granulation, mixing using high-speed mixers and extrusion without solid inert material.

For the preparation of disk, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, pp. 8–57.

For further details on the formulation of plant protection agents see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations contain 0.1 to 99% by weight, in particular 0.1 to 95% by weight, of active substance of the formula (I). In wettable powders, the active substance concentration is, for example, approximately 10 to 90% by weight, the remainder to 100% by weight consists of customary formulation constituents. In the case of emulsifiable concentrates, the active substance concentration can be approximately 1 to 90, preferably 5 to 80, % by weight. Formulations in the form of dusts contain 1 to 30% by weight of active substance, preferably usually 5 to 20% by weight of active substance, sprayable solutions contain approximately 0.05 to 80, preferably 2 to 50, % by weight of active substance. In the case of water-dispersible granules, the active substance content depends partly on whether the active compound is liquid or solid and which granulation auxiliaries, fillers etc. are used. In the case of water-dispersible granules, the content of active substance is, for example, between 1 and 95% by weight, preferably between 10 and 80% by weight.

In addition, the active substance formulations mentioned optionally contain the binders, wetting agents, dispersants, emulsifiers, penetrants, preservatives, antifreeze agents and solvents, fillers, carriers and colorants, antifoams, evaporation inhibitors and the pH and viscosity regulators which are customary in each case.

Components which can be employed for the active substances according to the invention in mixed formulations or in a tank mix are, for example, known active substances, such as are described, for example, in Weed Research 26, 441–445 (1986) or "The Pesticide Manual", 11th edition, The British Crop Protection Council and the Royal Soc. of Chemistry, 1997 and references cited there. Known herbicides which can be mentioned, which can be combined with the compounds of the formula (I), are, for example, the following active substances (note: the compounds are either designated by the common name according to the International Organization for Standardization (ISO) or using the chemical name, if appropriate together with a customary code number): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrole; AMS, i.e. ammonium sulfamate; anilofos; asulam; atrazine; azimsulfuron (DPX-A8947); aziprotryne; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (e.g. clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (e.g. butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazone; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (e.g. ethyl ester, HN-252); etobenzanid (HW 52); fenoprop; fenoxan, fenoxaprop and fenoxaprop-P and its esters, e.g. fenoxaprop-P-ethyl and fenoxaprop-ethyl; fenoxydim; fenuron; flamprop-methyl; flazasulfuron; fluazifop and fluazifop-P and its esters, e.g. fluazifop-butyl and fluazifop-P-butyl; fluchloralin; flumetsulam; flumeturon; flumiclorac and its esters (e.g. pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (e.g. methyl ester, NC-319); haloxyfop and its esters; haloxyfop-P (=R-haloxyfop) and its esters; hexazinone; imazamethabenz-methyl; imazapyr; imazaquin and salts such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidide; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (e.g. propargyl ester); quinclorac; quinmerac; quinofop and its ester derivatives; quizalofop and quizalofop-P and their ester derivates, e.g. quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)-phenoxy]-2-naphthalenyl]oxy]propanoic acid and its methyl ester; sulfentrazone (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i e. N,N-diethyl-3-[(2-ethyl-6-methylphenyl)-sulfonyl]-1H-1,2,4-triazole-1-carboxamide; thenylchlor (NSK-850); thiazafluron; thiazopyr (Mon-1 3200); thidiazimin (SN-24085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (e.g. methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations present in commercially available form are diluted, if appropriate, in a customary manner, e.g. by means of water in the case of wettable powders, emulsifiable concentrates, dispersions and water-dispersible granules. Preparations in the form of dusts, soil or broadcasting granules and sprayable solutions are customarily not diluted further with other inert substances before use.

The application rate of the compounds of the formula (I) necessary varies with the external conditions such as, inter alia, temperature, humidity and the type of herbicide used. It can vary within wide limits, e.g. between 0.001 and 10.0 kg/ha or more of active substance, but is preferably between 0.005 and 5 kg/ha.

The examples below illustrate the invention.

A. CHEMICAL EXAMPLES

1. Preparation of 2-(2-chloro-3-cyclohexanyloxymethyl-4-methylsulfonylbenzoyl)cyclohexane-1,3-dione

Step 1: 2-Chloro-6-methylthiotoluene 200 g (1.24 mol) of 2,6-dichlorotoluene were dissolved in 600 ml of hexamethylphosphoramide and treated with 130.41 g (1.86 mol) of sodium thiomethoxide. The mixture was then heated at 100° C. for 3 h. It was allowed to cool, 88.2 g (0.5 mol) of iodomethane were added and it was stirred at room temperature for 0.5 h. The mixture was then added to 3.5 l of water and extracted with ethyl acetate. The combined organic phases were washed with water, dried over $MgSO_4$ and completely concentrated on a rotary evaporator.

Yield: 208.85 g (97% of theory), yellow oil $^1$H NMR ($CDCl_3$): δ2.4 (s,3H), 2.42 (s,3H), 7.0–7.18 (m, 3H)

Step 2: 2-Chloro-3-methyl-4-methylthioacetophenone 47.36 g (0.60 mol) of acetyl chloride in 200 ml of 1,2-dichloroethane were added dropwise at 15–20° C. to a suspension of 90.79 g (0.68 mol) of aluminum chloride in 200 ml of 1,2-dichloroethane. A solution of 103.14 g (0.60 mol) of 2-chloro-6-methylthiotoluene in 400 ml of 1,2-dichloroethane was then added dropwise. The reaction mixture was stirred overnight at room temperature and added to a mixture of 1 l of ice and 300 ml of conc. HCl. It was extracted with methylene chloride. The combined organic phases were washed with water, dried over $MgSO_4$ and completely concentrated on a rotary evaporator. The residue was distilled in vacuo.

Yield: 111.24 g (87% of theory), colorless crystals, m.p.: 45.5–46° C.

¹H NMR (CDCl₃): δ2.42 (s,3H), 2.5 (s,3H), 2.6 (s,3H), 7.05 (d,1H), 7.35 (d,1H)

Step 3: 2-Chloro-3-methyl-4-methylsulfonylacetophenone 223.48 g (1.04 mol) of 2-chloro-3-methyl-4-methylthioacetophenone were dissolved in 1.8 l of glacial acetic acid and treated with 27.47 g (0.08 mol) of sodium tungstate. 203.83 g of a 30% strength hydrogen peroxide solution were then allowed to run in dropwise with cooling and the mixture was stirred at room temperature for 1.5 d. It was diluted with 1.5 l of water, and the precipitated solid was filtered off with suction and washed with water and dried.

Yield: 123.35 g (48% of theory), colorless crystals, m.p.: 110–111° C.

¹H NMR (CDCl₃): δ2.62 (s,3H), 2.8 (s,3H), 3.12 (s,3H), 7.38 (d,1H), 8.08 (d,1H)

Step 4: 2-Chloro-3-methyl-4-methylsulfonylbenzoic acid 60 g (0.24 mol) of 2-chloro-3-methyl-4-methylsulfonylacetophenone were dissolved in 510 ml of dioxane and treated with 870 g of 13% strength sodium hypochlorite solution. The mixture was then heated at 80° C. for a further 1 h. After cooling, the lower phase was separated off, diluted with water and acidified with HCl. The precipitated solid was filtered off with suction, washed with water and dried.

Yield: 53.02 g (88% of theory), colorless crystals, m.p.: 230–231° C.

¹H NMR (Me₂SO-d6): δ2.75 (s,3H), 3.3 (s,3H), 7.75 (d,1H), 7.98 (d,1H)

Step 5: Methyl 2-chloro-3-methyl-4-methylsulfonylbenzoate 53.02 g (0.21 mol) of 2-chloro-3-methyl-4-methylsulfonylbenzoic acid were dissolved in 400 ml of methanol and HCl was passed in at reflux temperature for 3 h. The mixture was then allowed to cool and completely concentrated on a rotary evaporator.

Yield: 54.93 g (98% of theory), colorless crystals, m.p.: 107–108° C.

¹H NMR (CDCl₃): δ2.82 (s,3H), 3.15 (s,3H), 3.98 (s,3H), 7.65 (d,1H), 8.04 (d,1H)

Step 6: Methyl 3-bromomethyl-2-chloro-4-methylsulfonylbenzoate 44.14 g (0.17 mol) of methyl 2-chloro-3-methyl-4-methylsulfonylbenzoate were dissolved in 600 ml of carbon tetrachloride and treated with 29.91 g (0.17 mol) of N-bromosuccinimide and 0.41 g of dibenzoyl peroxide. The mixture was then refluxed and illuminated with a 300 W lamp. The reaction mixture was filtered, the filtrate was concentrated and the residue was taken up in diethyl ether. The solution was treated with n-heptane, and the precipitated solid was filtered off with suction and dried.

Yield: 38.82 g (67% of theory), colorless crystals, m.p.: 74–75° C.

¹H NMR (CDCl₃): δ3.35 (s,3H), 4.00 (s,3H), 5.3 (s, br, 2H), 7.8 (d,1H), 8.15 (d,1H)

Step 7: 2-Chloro-3-cyclohexanyloxymethyl-4-methylsulfonylbenzoic acid 1.0 g (2.93 mmol) of methyl 3-bromomethyl-2-chloro-4-methylsulfonylbenzoate was dissolved in 10 ml of cyclohexanol and treated with 0.33 g (2.93 mmol) of potasium tert-butoxide. The mixture was stirred overnight at room temperature and then concentrated on a rotary evaporator. The residue was dissolved in 16 ml of tetrahydrofuran and 8 ml of water and refluxed for 4 h together with 0.55 g of NaOH (13.74 mmol). It was then allowed to cool and was largely concentrated on a rotary evaporator and the aqueous residue was then treated with 2 M HCl. It was then extracted with methylene chloride, and the combined organic phase was dried over MgSO₄ and completely concentrated on a rotary evaporator.

Yield: 0.53 g (52% of theory), colorless oil,

¹H NMR (CDCl₃): δ0.9 (m, 6H), 1.3 (m, 4 H), 3.3 (s,3H), 4.75 (m,1H), 5.3 (s, 2H), 7.9 (d,1H), 8.1 (d,1H)

Step 8: 3-Oxo-1-cyclohexenyl 2-chloro-3-cyclohexanyloxymethyl-4-methylsulfonylbenzoate 0.53 g (1.53 mmol) of 2-chloro-3-cyclohexanyloxymethyl-4-methylsulfonylbenzoic acid was treated with 2 drops of N,N-dimethylformamide and 0.59 g (4.58 mmol) of oxalyl chloride in 23 ml of methylene chloride and the mixture was refluxed for 2.5 h. It was then stripped off on a rotary evaporator, the residue was taken up in 23 ml of methylene chloride and the mixture was treated at 0° C. with 0.19 g (1.68 mmol) of cyclohexanedione and 0.46 g (4.58 mmol) of triethylamine. It was stirred at room temperature for 4 h. It was then concentrated on a rotary evaporator and purified by chromatography (silica gel, ethyl acetate:hexane=1:1).

Yield: 0.1 g (15% of theory), colorless oil

¹H NMR (CDCl₃): δ0.9 (m, 6H), 1.3 (m, 4H), 2.35 (m,2H), 2.5 (m,2H), 2.7 (m,2H), 3.35 (s,3H), 5.4 (s, br, 2H), 6.1 (s,1H), 7.95 (d,2H), 8.2 (d,2H)

Step 9: 2-(2-Chloro-3-cyclohexanyloxymethyl-4-methylsulfonylbenzoyl)cyclohexane-1,3-dione 0.10 g (0.23 mmol) of 3-oxo-1-cyclohexenyl 2-chloro-3-cyclohexanyloxymethyl-4-methylsulfonylbenzoate, 1 drop of acetone cyanohydrin and 0.04 g (0.39 mmol) of triethylamine were dissolved in 5 ml of acetonitrile and the solution was stirred overnight at room temperature. It was then concentrated on a rotary evaporator, and the residue was treated with 5 ml of water and rendered acidic using 5 M HCl. The mixture was extracted with ethyl acetate, and the organic phase was washed with water, dried over MgSO₄ and completely concentrated on a rotary evaporator.

Yield: 0.1 g (100% of theory), colorless oil, $R_f$=0.07 (SiO₂/ethyl acetate)

¹H NMR (CDCl₃): δ0.9 (m, 6H), 1.3 (m, 4H), 2.1 (m,2H), 2.45 (m,2H), 2.85 (m,2H), 3.3 (s,3H), 4.55 (s, 1H), 5.35 (s, br, 2H), 7.3 (d,2H), 8.15 (d, 2H)

2. Preparation of 2-(2-chloro-4-methylsulfonyl-3-phenoxymethylbenzoyl)cyclohexane-1,3-dione

Step 1: 2-Chloro-4-methylsulfonyl-3-phenoxymethylbenzoic acid 1.0 g (2.93 mmol) of methyl 3-bromomethyl-2-chloro-4-methylsulfonylbenzoate and 0.28 g (2.93 mmol) of phenol were dissolved in 20 ml of dimethylformamide and treated with 0.14 g (3.51 mmol) of 60% strength sodium hydride. The mixture was stirred overnight at room temperature and then concentrated in a high vacuum on a rotary evaporator. The residue was dissolved in 16 ml of tetrahydrofuran and 8 ml of water and the solution was refluxed for 4 h together with 0.23 g of NaOH (5.85 mmol). It was then allowed to cool and was largely concentrated on a rotary evaporator, and the aqueous residue was then treated with 2 M HCl. It was then extracted with methylene chloride, and the combined organic phase was dried over MgSO₄ and completely concentrated on a rotary evaporator.

Yield: 0.67 g (67% of theory), coloress oil

¹H NMR (Me₂SO-d6): δ3.3 (s,3H), 5.55 (s, 2H), 6.98–7.05 (m, 3H), 7.35 (m, 2H), 7.95 (d,1H), 8.1 (d,1H)

Step 2: 3-Oxo-1-cyclohexenyl 2-chloro-4-methylsulfonyl-3-phenoxymethylbenzoic acid 0.67 g (1.97 mmol) of 2-chloro-4-methylsulfonyl-3-phenoxymethylbenzoic acid was treated with 2 drops of N,N-dimethylformamide and 0.76 g (5.9 mmol) of oxalyl chloride in 30 ml of methylene chloride and the mixture was refluxed for 2.5 h. It was then stripped off on a rotary evaporator, the residue was taken up in 30 ml of methylene chloride and the mixture was treated at 0° C. with 0.24 g (2.16 mmol) of cyclohexanedione and 0.60 g (5.9 mmol) of triethylamine. It was stirred at room temperature for 4 h. It was then concentrated on a rotary evaporator and purified by chromatography (silica gel, ethyl acetate:hexane=1:1).

Yield: 0.51 g (60% of theory), colorless oil

¹H NMR (CDCl₃): δ2.15 (m, 2H), 2.45 (m, 2H), 2.7 (m, 2H), 3.2 (s,3H), 5.75 (s, 2H), 6.08 (s,1H), 7.0–7.1 (m, 3H), 7.35 (m, 2H), 7.98 (d,1H), 8.25 (d,1H)

Step 3: 2-(2-Chloro-4-methylsulfonyl-3-phenoxymethylbenzoyl)cyclohexane-1,3-dione 0.51 g (1.17 mmol) of 3-oxo-1-cyclohexenyl 2-chloro-4-methylsulfonyl-3-phenoxymethylbenzoic acid, 1 drop of acetone cyanohydrin and 0.21 g (2.04 mmol) of triethylamine were dissolved in 20 ml of acetonitrile and the solution was stirred at room temperature overnight. It was then concentrated on a rotary evaporator, treated with 5 ml of water and rendered acidic using 5 M HCl. It was extracted with ethyl acetate, washed with water, dried over MgSO₄ and completely concentrated on a rotary evaporator. The residue was extracted with ethyl acetate, and the organic phase was washed with water, dried over MgSO₄ and completely concentrated on a rotary evaporator.

Yield: 0.5 g (98% of theory), colorless oil, $R_f$=0.22 (SiO₂/ethyl acetate)

¹H NMR (CDCl₃): δ2.08 (m,2H), 2.45 (m,2H), 2.85 (m,2H), 3.2 (s,3H), 5.7 (s, br, 2H), 7.0 (d,2H), 7.05 (m, 2H), 7.35 (m, 3H), 8.18 (d, 2H).

The examples shown in the following tables were prepared analogously to the abovementioned methods or are obtainable analogously to the abovementioned methods.

The abbreviations used in the tables have the following meanings:

| Ac = | acetyl | Bu = | butyl | Bz = | benzoyl |
|---|---|---|---|---|---|
| Et = | ethyl | Me = | methyl | Pr = | propyl |
| c = | cyclo | d = | doublet | dd = | double doublet |
| s = | singlet | m = | multiplet | t = | triplet |
| i = | iso | m.p. = | melting point | | |

TABLE 1

Compounds of the formula (I) according to the invention in which the substituents and symbols have the following meanings:

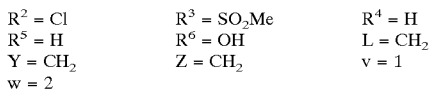

R² = Cl       R³ = SO₂Me     R⁴ = H
R⁵ = H        R⁶ = OH        L = CH₂
Y = CH₂       Z = CH₂        v = 1
w = 2

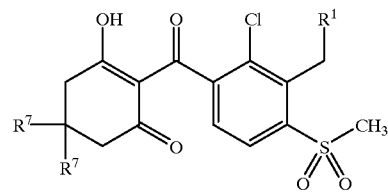

| No. | R¹ | R⁷ | Physical data |
|---|---|---|---|
| 3 | OCH₂CF₃ | H | ¹H NMR (CDCl₃): δ 2.05(m, 2H), 2.45(m, 2H), 2.8(m, 2H), 3.25(s, 3H), 4.05(q, 2H), 5.35(s, 2H), 7.35(d, 1H), 8.15(d, 1H) |
| 4 | O(CH₂)₂O(CH₂)₂OEt | H | ¹H NMR (CDCl₃): δ 1.2(t, 3H), 2.05(m, 2H), 2.45(m, 2H), 2.8(m, 2H), 3.35(s, 3H), 3.45(q, 2H), 3.58(m, 4H), 3.7(m, 2H), 3.85(m, 2H), 5.2(s, 2H), 7.3(d, 1H), 8.1(d, 1H) |
| 5 | [tetrahydropyranylmethoxy structure] | H | ¹H NMR (CDCl₃): δ 1.55(m, 6H), 2.05(m, 2H), 2.45(m, 2H), 2.8(m, 2H), 3.35(s, 3H), 3.6(m, 2H), 3.95(m, 2H), 4.3(m, 1H), 5.15(m, 2H), 7.3(d, 1H), 8.1(d, 1H) |
| 6 | O(CH₂)₂O(CH₂)₂O(CH₂)₅Me | H | ¹H NMR (CDCl₃): δ 2.05(m, 2H), 2.45(m, 2H), 2.82(m, 2H), 3.28(s, 3H), 5.88(s, 2H), 7.12(m, 1H), 7.35(m, 1H), 7.2(d, 1H), 7.65(m, 1H), 7.85(m, 1H), 8.18(d, 1H) |
| 7 | benzyloxyethoxy | H | ¹H NMR (CDCl₃): δ 2.05(m, 2H), 2.3(s, 6H), 2.45(m, 2H), 2.8(m, 2H), 3.2(s, 3H), 5.65(s, 2H), 6.65(s, 2H), 6.7(s, 1H), 7.35(d, 1H), 8.18(d, 1H) |
| 8 | OCH₂CF₂CF₂H | H | ¹H NMR (CDCl₃): δ 2.05(m, 2H), 2.45(m, 2H), 2.85(m, 2H), 3.2(s, 3H), 4.02(t, 2H), 5.3(m, 2H), 5.9(m, 1H), 7.35(d, 1H), 8.15(d, 1H) |
| 9 | O-c-pentyl | H | ¹H NMR (CDCl₃): δ 1.5–1.85(m, 8H), 2.16 (m, 2H), 2.5(m, 2H), 2.82(m, 2H), 3.3(s, 3H), 4.2(m, 1H), 5.05(s, 2H), 7.25(d, 1H), 8.1(d, 1H) |
| 10 | O(CH₂)₂O(CH₂)₂O(CH₂)₂OMe | H | ¹H NMR (CDCl₃): δ 2.05(m, 2H), 2.45(m, 2H), 2.82(m, 2H), 3.4(s, 3H), 3.5–3.85(m, 12H), 5.25 (s, 2H), 7.35(d, 1H), 8.15(d, 1H) |
| 11 | O(CH₂)₂O(CH₂)₂OMe | H | ¹H NMR (CDCl₃): δ 2.05(m, 2H), 2.45(m, 2H), 2.82(m, 2H), 3.35(s, 3H), 3.38–3.8(m, 8H), 5.2 (s, 2H), 7.3(d, 1H), 8.1(d, 1H) |

TABLE 1-continued

Compounds of the formula (I) according to the invention in which the substituents and symbols have the following meanings:

R² = Cl   R³ = SO₂Me   R⁴ = H
R⁵ = H   R⁶ = OH   L = CH₂
Y = CH₂   Z = CH₂   v = 1
w = 2

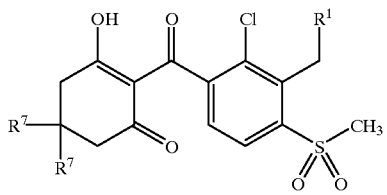

| No. | R¹ | R⁷ | Physical data |
|---|---|---|---|
| 12 | O-c-Bu | Me | ¹H NMR (CDCl₃): δ 1.15(s, 6H), 1.55(m, 1H), 1.75(m, 1H), 2.00(m, 2H), 2.25(m, 2H), 2.3(s, 2H), 2.7(s, 2H), 3.3(s, 3H), 4.12(m, 1H), 5.02(s, 2H), 7.3(d, 1H), 8.15(d, 1H), 16.8(s, 1H) |
| 13 | 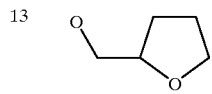 | H | ¹H NMR (CDCl₃): δ 1.6(m, 1H), 1.8–2.0 (m, 3H), 2.1(m, 2H), 2.42(m, 2H), 2.82(m, 2H), 3.35(s, 3H), 3.62(m, 2H), 3.78(m, 2H), 4.05(m, 1H), 5.2(s, 2H), 7.28(d, 1H), 8.12(d, 1H), 16.75(s, 1H) |
| 14 | O-c-Bu | H | ¹H NMR (CDCl₃): δ 1.55(m, 1H), 1.75(m, 1H), 2.0(m, 2H), 2.1(m, 2H), 2.25(m, 2H), 2.45(m, 2H), 2.82(m, 2H), 3.3(s, 3H), 4.12(m, 1H), 5.02(s, 2H), 7.28(d, 1H), 8.1(d, 1H), 16.78(s, 1H) |
| 15 | O—CH₂-c-Pr | H | ¹H NMR (CDCl₃): δ 0.25(m, 2H), 0.6(m, 2H), 0.9(m, 1H), 2.1(m, 2H), 2.42(m, 2H), 2.82(m, 2H), 3.35(s, 3H), 3.45(d, 2H), 5.15(s, 2H), 7.28(d, 1H), 8.1(d, 1H), 16.78(s, 1H) |
| 16 | OCH₂CF₂CF₃ | H | |
| 17 | OCH₂CF₂CF₃ | Me | |
| 18 | OCH₂CF₂CF₂CF₃ | H | |
| 19 | OCH₂CF₂CF₂CF₃ | Me | |
| 20 | OCH₂CH₂Cl | H | |
| 21 | OCH₂CH₂Cl | Me | |
| 22 | OCH₂CH₂Br | H | |
| 23 | OCH₂CH₂Br | Me | |
| 24 | OCH₂CH₂F | H | |
| 25 | OCH₂CH₂F | Me | |
| 26 | OCH₂CHF₂ | H | |
| 27 | OCH₂CHF₂ | Me | |
| 28 | SCH₂CF₃ | H | |
| 29 | SCH₂CF₃ | Me | |

TABLE 1a

Precursors of the compounds in Table 1

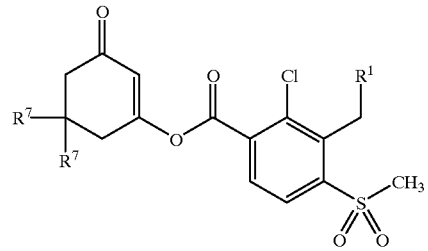

| No. | R¹ | R⁷ | Physical data |
|---|---|---|---|
| 3a | OCH₂CF₃ | H | ¹H NMR (CDCl₃): δ 2.15(m, 2H), 2.5(m, 2H), 2.7(m, 2H), 3.25(s, 3H), 4.1(q, 2H), 5.2(s, 2H), 6.1(m, 1H), 7.95(d, 1H), 8.2(d, 1H) |
| 4a | O(CH₂)₂O(CH₂)₂OEt | H | ¹H NMR (CDCl₃): δ 1.2(t, 3H), 2.15(m, 2H), 2.5(m, 2H), 2.7(m, 2H), 3.38(s, 3H), 3.5(q, 2H), 3.58(m, 4H), 3.7(m, 2H), 3.85(m, 2H), 5.25(s, 2H), 6.1(m, 1H), 7.9(d, 1H), 8.18(d, 1H) |
| 5a | 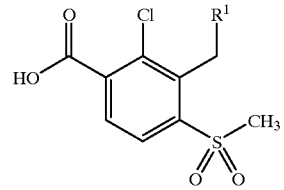 | H | ¹H NMR (CDCl₃): δ 1.55(m, 6H), 2.15(m, 2H), 2.5(m, 2H), 2.7(m, 2H), 3.35(s, 3H), 3.6(m, 2H), 3.95(m, 2H), 4.3(m, 1H), 5.2(s, 2H), 6.08(m, 1H), 7.85(d, 1H), 8.18(d, 1H) |
| 9a | O-c-pentyl | H | ¹H NMR (CDCl₃): δ 1.5–1.85(m, 8H), 2.15(m, 2H), 2.5(m, 2H), 2.7(m, 2H), 3.3(s, 3H), 4.2(m, 1H), 5.1(s, 2H), 6.1(s, 1H), 7.88(d, 1H), 8.18(d, 1H) |

TABLE 1b

Precursors of the compounds in Table 1a

| No. | R¹ | R⁷ | Physical data |
|---|---|---|---|
| 3b | OCH₂CF₃ | H | ¹H NMR (Me₂SO-d6): δ 3.35(s, 3H), 4.3(q, 2H), 5.22(s, 2H), 7.9(d, 1H), 8.05(d, 1H) |
| 4b | O(CH₂)₂O(CH₂)₂OEt | H | ¹H NMR (CDCl₃): δ 1.2(t, 3H), 3.35(s, 3H), 3.6(m, 4H), 3.7(m, 2H), 3.5(q, 2H), 3.85(m, 2H), 5.25(s, 2H), 7.9(d, 1H), 8.15(d, 1H) |

TABLE 1b-continued

Precursors of the compounds in Table 1a

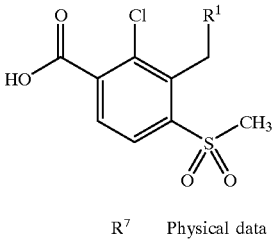

| No. | R¹ | R⁷ | Physical data |
|---|---|---|---|
| 5b | <structure: tetrahydropyranyl-CH₂-O-> | H | $^1$H NMR (CDCl$_3$): δ 1.55(m, 6H), 3.35(s, 3H), 3.65(m, 2H), 4.0(m, 2H), 4.35(m, 1H), 5.12(s, 2H), 7.85(d, 1H), 8.1(d, 1H) |
| 9b | O-c-pentyl | H | $^1$H NMR (CDCl$_3$): δ 1.5–1.85(m, 8H), 3.25(s, 3H), 4.2(m, 1H), 5.1(s, 2H), 7.9(d, 1H), 8.15(d, 1H) |

TABLE 2

Compounds of the formula (I) according to the invention in which the substituents and symbols have the following meanings:

$R^2 = Cl$, $R^3 = SO_2Me$, $R^4 = H$
$R^5 = H$, $R^6 = OR^{12}$, $R^7 = R^{7a}, R^{7b}$
$Y = CH_2$, $Z = CH_2$, $v = 1$
$w = 2$

| No. | R⁷ᵃ | R⁷ᵇ | R¹² | L | R¹ |
|---|---|---|---|---|---|
| 30 | H | H | Bz | CH₂ | O-c-hexyl |
| 31 | H | Me | Bz | CH₂ | O-c-hexyl |
| 32 | Me | Me | Bz | CH₂ | O-c-hexyl |
| 33 | H | H | PhC(O)CH₂ | CH₂ | O-c-hexyl |
| 34 | H | Me | PhC(O)CH₂ | CH₂ | O-c-hexyl |
| 35 | Me | Me | PhC(O)CH₂ | CH₂ | O-c-hexyl |
| 36 | H | H | 4-Me—Bz | CH₂ | O-c-hexyl |
| 37 | H | Me | 4-Me—Bz | CH₂ | O-c-hexyl |
| 38 | Me | Me | 4-Me—Bz | CH₂ | O-c-hexyl |
| 39 | H | H | MeSO₂ | CH₂ | O-c-hexyl |
| 40 | H | Me | MeSO₂ | CH₂ | O-c-hexyl |
| 41 | Me | Me | MeSO₂ | CH₂ | O-c-hexyl |
| 42 | H | H | EtSO₂ | CH₂ | O-c-hexyl |
| 43 | H | Me | EtSO₂ | CH₂ | O-c-hexyl |
| 44 | Me | Me | EtSO₂ | CH₂ | O-c-hexyl |
| 45 | H | H | PrSO₂ | CH₂ | O-c-hexyl |
| 46 | H | Me | PrSO₂ | CH₂ | O-c-hexyl |
| 47 | Me | Me | PrSO₂ | CH₂ | O-c-hexyl |
| 48 | H | H | PhSO₂ | CH₂ | O-c-hexyl |
| 49 | H | Me | PhSO₂ | CH₂ | O-c-hexyl |
| 50 | Me | Me | PhSO₂ | CH₂ | O-c-hexyl |
| 51 | H | H | 4-Me—PhSO₂ | CH₂ | O-c-hexyl |
| 52 | H | Me | 4-Me—PhSO₂ | CH₂ | O-c-hexyl |
| 53 | Me | Me | 4-Me—PhSO₂ | CH₂ | O-c-hexyl |
| 54 | H | H | Bz | CH₂ | O-c-pentyl |
| 55 | H | Me | Bz | CH₂ | O-c-pentyl |
| 56 | Me | Me | Bz | CH₂ | O-c-pentyl |
| 57 | H | H | PhC(O)CH₂ | CH₂ | O-c-pentyl |
| 58 | H | Me | PhC(O)CH₂ | CH₂ | O-c-pentyl |
| 59 | Me | Me | PhC(O)CH₂ | CH₂ | O-c-pentyl |
| 60 | H | H | 4-Me—Bz | CH₂ | O-c-pentyl |
| 61 | H | Me | 4-Me—Bz | CH₂ | O-c-pentyl |
| 62 | Me | Me | 4-Me—Bz | CH₂ | O-c-pentyl |
| 63 | H | H | MeSO₂ | CH₂ | O-c-pentyl |
| 64 | H | Me | MeSO₂ | CH₂ | O-c-pentyl |
| 65 | Me | Me | MeSO₂ | CH₂ | O-c-pentyl |
| 66 | H | H | EtSO₂ | CH₂ | O-c-pentyl |
| 67 | H | Me | EtSO₂ | CH₂ | O-c-pentyl |
| 68 | Me | Me | EtSO₂ | CH₂ | O-c-pentyl |
| 69 | H | H | PrSO₂ | CH₂ | O-c-pentyl |
| 70 | H | Me | PrSO₂ | CH₂ | O-c-pentyl |
| 71 | Me | Me | PrSO₂ | CH₂ | O-c-pentyl |
| 72 | H | H | PhSO₂ | CH₂ | O-c-pentyl |
| 73 | H | Me | PhSO₂ | CH₂ | O-c-pentyl |
| 74 | Me | Me | PhSO₂ | CH₂ | O-c-pentyl |
| 75 | H | H | 4-Me—PhSO₂ | CH₂ | O-c-pentyl |
| 76 | H | Me | 4-Me—PhSO₂ | CH₂ | O-c-pentyl |
| 77 | Me | Me | 4-Me—PhSO₂ | CH₂ | O-c-pentyl |
| 78 | H | H | Bz | CH₂ | O-c-Bu |
| 79 | H | Me | Bz | CH₂ | O-c-Bu |
| 80 | Me | Me | Bz | CH₂ | O-c-Bu |
| 81 | H | H | PhC(O)CH₂ | CH₂ | O-c-Bu |
| 82 | H | Me | PhC(O)CH₂ | CH₂ | O-c-Bu |
| 83 | Me | Me | PhC(O)CH₂ | CH₂ | O-c-Bu |
| 84 | H | H | 4-Me—Bz | CH₂ | O-c-Bu |
| 85 | H | Me | 4-Me—Bz | CH₂ | O-c-Bu |
| 86 | Me | Me | 4-Me—Bz | CH₂ | O-c-Bu |
| 87 | H | H | MeSO₂ | CH₂ | O-c-Bu |
| 88 | H | Me | MeSO₂ | CH₂ | O-c-Bu |
| 89 | Me | Me | MeSO₂ | CH₂ | O-c-Bu |
| 90 | H | H | EtSO₂ | CH₂ | O-c-Bu |
| 91 | H | Me | EtSO₂ | CH₂ | O-c-Bu |
| 92 | Me | Me | EtSO₂ | CH₂ | O-c-Bu |
| 93 | H | H | PrSO₂ | CH₂ | O-c-Bu |
| 94 | H | Me | PrSO₂ | CH₂ | O-c-Bu |
| 95 | Me | Me | PrSO₂ | CH₂ | O-c-Bu |
| 96 | H | H | PhSO₂ | CH₂ | O-c-Bu |
| 97 | H | Me | PhSO₂ | CH₂ | O-c-Bu |
| 98 | Me | Me | PhSO₂ | CH₂ | O-c-Bu |
| 99 | H | H | 4-Me—PhSO₂ | CH₂ | O-c-Bu |
| 100 | H | Me | 4-Me—PhSO₂ | CH₂ | O-c-Bu |
| 101 | Me | Me | 4-Me—PhSO₂ | CH₂ | O-c-Bu |
| 102 | H | H | Bz | CH₂ | O-c-Pr |
| 103 | H | Me | Bz | CH₂ | O-c-Pr |
| 104 | Me | Me | Bz | CH₂ | O-c-Pr |
| 105 | H | H | PhC(O)CH₂ | CH₂ | O-c-Pr |
| 106 | H | Me | PhC(O)CH₂ | CH₂ | O-c-Pr |
| 107 | Me | Me | PhC(O)CH₂ | CH₂ | O-c-Pr |
| 108 | H | H | 4-Me—Bz | CH₂ | O-c-Pr |
| 109 | H | Me | 4-Me—Bz | CH₂ | O-c-Pr |
| 110 | Me | Me | 4-Me—Bz | CH₂ | O-c-Pr |
| 111 | H | H | MeSO₂ | CH₂ | O-c-Pr |
| 112 | H | Me | MeSO₂ | CH₂ | O-c-Pr |
| 113 | Me | Me | MeSO₂ | CH₂ | O-c-Pr |
| 114 | H | H | EtSO₂ | CH₂ | O-c-Pr |
| 115 | H | Me | EtSO₂ | CH₂ | O-c-Pr |
| 116 | Me | Me | EtSO₂ | CH₂ | O-c-Pr |

TABLE 2-continued

Compounds of the formula (I) according to the invention in which the substituents and symbols have the following meanings:

$R^2$ = Cl          $R^3$ = $SO_2Me$        $R^4$ = H
$R^5$ = H          $R^6$ = $OR^{12}$        $R^7$ = $R^{7a}$, $R^{7b}$
Y = $CH_2$         Z = $CH_2$               v = 1
w = 2

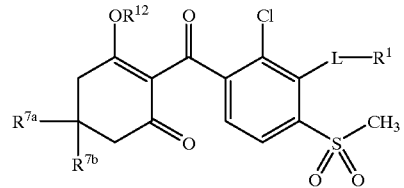

| No. | $R^{7a}$ | $R^{7b}$ | $R^{12}$ | L | $R^1$ |
|---|---|---|---|---|---|
| 117 | H | H | $PrSO_2$ | $CH_2$ | O-c-Pr |
| 118 | H | Me | $PrSO_2$ | $CH_2$ | O-c-Pr |
| 119 | Me | Me | $PrSO_2$ | $CH_2$ | O-c-Pr |
| 120 | H | H | $PhSO_2$ | $CH_2$ | O-c-Pr |
| 121 | H | Me | $PhSO_2$ | $CH_2$ | O-c-Pr |
| 122 | Me | Me | $PhSO_2$ | $CH_2$ | O-c-Pr |
| 123 | H | H | 4-Me—$PhSO_2$ | $CH_2$ | O-c-Pr |
| 124 | H | Me | 4-Me—$PhSO_2$ | $CH_2$ | O-c-Pr |
| 125 | Me | Me | 4-Me—$PhSO_2$ | $CH_2$ | O-c-Pr |
| 126 | H | H | Bz | $CH_2$ | $OCH_2CF_3$ |
| 127 | H | Me | Bz | $CH_2$ | $OCH_2CF_3$ |
| 128 | Me | Me | Bz | $CH_2$ | $OCH_2CF_3$ |
| 129 | H | H | $PhC(O)CH_2$ | $CH_2$ | $OCH_2CF_3$ |
| 130 | H | Me | $PhC(O)CH_2$ | $CH_2$ | $OCH_2CF_3$ |
| 131 | Me | Me | $PhC(O)CH_2$ | $CH_2$ | $OCH_2CF_3$ |
| 132 | H | H | 4-Me—Bz | $CH_2$ | $OCH_2CF_3$ |
| 133 | H | Me | 4-Me—Bz | $CH_2$ | $OCH_2CF_3$ |
| 134 | Me | Me | 4-Me—Bz | $CH_2$ | $OCH_2CF_3$ |
| 135 | H | H | $MeSO_2$ | $CH_2$ | $OCH_2CF_3$ |
| 136 | H | Me | $MeSO_2$ | $CH_2$ | $OCH_2CF_3$ |
| 137 | Me | Me | $MeSO_2$ | $CH_2$ | $OCH_2CF_3$ |
| 138 | H | H | $EtSO_2$ | $CH_2$ | $OCH_2CF_3$ |
| 139 | H | Me | $EtSO_2$ | $CH_2$ | $OCH_2CF_3$ |
| 140 | Me | Me | $EtSO_2$ | $CH_2$ | $OCH_2CF_3$ |
| 141 | H | H | $PrSO_2$ | $CH_2$ | $OCH_2CF_3$ |
| 142 | H | Me | $PrSO_2$ | $CH_2$ | $OCH_2CF_3$ |
| 143 | Me | Me | $PrSO_2$ | $CH_2$ | $OCH_2CF_3$ |
| 144 | H | H | $PhSO_2$ | $CH_2$ | $OCH_2CF_3$ |
| 145 | H | Me | $PhSO_2$ | $CH_2$ | $OCH_2CF_3$ |
| 146 | Me | Me | $PhSO_2$ | $CH_2$ | $OCH_2CF_3$ |
| 147 | H | H | 4-Me—$PhSO_2$ | $CH_2$ | $OCH_2CF_3$ |
| 148 | H | Me | 4-Me—$PhSO_2$ | $CH_2$ | $OCH_2CF_3$ |
| 149 | Me | Me | 4-Me—$PhSO_2$ | $CH_2$ | $OCH_2CF_3$ |
| 150 | H | H | Bz | $CH_2CH_2$ | O-c-hexyl |
| 151 | H | Me | Bz | $CH_2CH_2$ | O-c-hexyl |
| 152 | Me | Me | Bz | $CH_2CH_2$ | O-c-hexyl |
| 153 | H | H | $PhC(O)CH_2$ | $CH_2CH_2$ | O-c-hexyl |
| 154 | H | Me | $PhC(O)CH_2$ | $CH_2CH_2$ | O-c-hexyl |
| 155 | Me | Me | $PhC(O)CH_2$ | $CH_2CH_2$ | O-c-hexyl |
| 156 | H | H | 4-Me—Bz | $CH_2CH_2$ | O-c-hexyl |
| 157 | H | Me | 4-Me—Bz | $CH_2CH_2$ | O-c-hexyl |
| 158 | Me | Me | 4-Me—Bz | $CH_2CH_2$ | O-c-hexyl |
| 159 | H | H | $MeSO_2$ | $CH_2CH_2$ | O-c-hexyl |
| 160 | H | Me | $MeSO_2$ | $CH_2CH_2$ | O-c-hexyl |
| 161 | Me | Me | $MeSO_2$ | $CH_2CH_2$ | O-c-hexyl |
| 162 | H | H | $EtSO_2$ | $CH_2CH_2$ | O-c-hexyl |
| 163 | H | Me | $EtSO_2$ | $CH_2CH_2$ | O-c-hexyl |
| 164 | Me | Me | $EtSO_2$ | $CH_2CH_2$ | O-c-hexyl |
| 165 | H | H | $PrSO_2$ | $CH_2CH_2$ | O-c-hexyl |
| 166 | H | Me | $PrSO_2$ | $CH_2CH_2$ | O-c-hexyl |
| 167 | Me | Me | $PrSO_2$ | $CH_2CH_2$ | O-c-hexyl |
| 168 | H | H | $PhSO_2$ | $CH_2CH_2$ | O-c-hexyl |
| 169 | H | Me | $PhSO_2$ | $CH_2CH_2$ | O-c-hexyl |
| 170 | Me | Me | $PhSO_2$ | $CH_2CH_2$ | O-c-hexyl |
| 171 | H | H | 4-Me—$PhSO_2$ | $CH_2CH_2$ | O-c-hexyl |
| 172 | H | Me | 4-Me—$PhSO_2$ | $CH_2CH_2$ | O-c-hexyl |
| 173 | Me | Me | 4-Me—$PhSO_2$ | $CH_2CH_2$ | O-c-hexyl |
| 174 | H | H | Bz | $CH_2CH_2$ | O-c-pentyl |
| 175 | H | Me | Bz | $CH_2CH_2$ | O-c-pentyl |
| 176 | Me | Me | Bz | $CH_2CH_2$ | O-c-pentyl |
| 177 | H | H | $PhC(O)CH_2$ | $CH_2CH_2$ | O-c-pentyl |
| 178 | H | Me | $PhC(O)CH_2$ | $CH_2CH_2$ | O-c-pentyl |
| 179 | Me | Me | $PhC(O)CH_2$ | $CH_2CH_2$ | O-c-pentyl |
| 180 | H | H | 4-Me—PhC(O) | $CH_2CH_2$ | O-c-pentyl |
| 181 | H | Me | 4-Me—PhC(O) | $CH_2CH_2$ | O-c-pentyl |
| 182 | Me | Me | 4-Me—PhC(O) | $CH_2CH_2$ | O-c-pentyl |
| 183 | H | H | $MeSO_2$ | $CH_2CH_2$ | O-c-pentyl |
| 184 | H | Me | $MeSO_2$ | $CH_2CH_2$ | O-c-pentyl |
| 185 | Me | Me | $MeSO_2$ | $CH_2CH_2$ | O-c-pentyl |
| 186 | H | H | $EtSO_2$ | $CH_2CH_2$ | O-c-pentyl |
| 187 | H | Me | $EtSO_2$ | $CH_2CH_2$ | O-c-pentyl |
| 188 | Me | Me | $EtSO_2$ | $CH_2CH_2$ | O-c-pentyl |
| 189 | H | H | $PrSO_2$ | $CH_2CH_2$ | O-c-pentyl |
| 190 | H | Me | $PrSO_2$ | $CH_2CH_2$ | O-c-pentyl |
| 191 | Me | Me | $PrSO_2$ | $CH_2CH_2$ | O-c-pentyl |
| 192 | H | H | $PhSO_2$ | $CH_2CH_2$ | O-c-pentyl |
| 193 | H | Me | $PhSO_2$ | $CH_2CH_2$ | O-c-pentyl |
| 194 | Me | Me | $PhSO_2$ | $CH_2CH_2$ | O-c-pentyl |
| 195 | H | H | 4-Me—$PhSO_2$ | $CH_2CH_2$ | O-c-pentyl |
| 196 | H | Me | 4-Me—$PhSO_2$ | $CH_2CH_2$ | O-c-pentyl |
| 197 | Me | Me | 4-Me—$PhSO_2$ | $CH_2CH_2$ | O-c-pentyl |
| 198 | H | H | Bz | $CH_2CH_2$ | O-c-Bu |
| 199 | H | Me | Bz | $CH_2CH_2$ | O-c-Bu |
| 200 | Me | Me | Bz | $CH_2CH_2$ | O-c-Bu |
| 201 | H | H | $PhC(O)CH_2$ | $CH_2CH_2$ | O-c-Bu |
| 202 | H | Me | $PhC(O)CH_2$ | $CH_2CH_2$ | O-c-Bu |
| 203 | Me | Me | $PhC(O)CH_2$ | $CH_2CH_2$ | O-c-Bu |
| 204 | H | H | 4-Me—Bz | $CH_2CH_2$ | O-c-Bu |
| 205 | H | Me | 4-Me—Bz | $CH_2CH_2$ | O-c-Bu |
| 206 | Me | Me | 4-Me—Bz | $CH_2CH_2$ | O-c-Bu |
| 207 | H | H | $MeSO_2$ | $CH_2CH_2$ | O-c-Bu |
| 208 | H | Me | $MeSO_2$ | $CH_2CH_2$ | O-c-Bu |
| 209 | Me | Me | $MeSO_2$ | $CH_2CH_2$ | O-c-Bu |
| 210 | H | H | $EtSO_2$ | $CH_2CH_2$ | O-c-Bu |
| 211 | H | Me | $EtSO_2$ | $CH_2CH_2$ | O-c-Bu |
| 212 | Me | Me | $EtSO_2$ | $CH_2CH_2$ | O-c-Bu |
| 213 | H | H | $PrSO_2$ | $CH_2CH_2$ | O-c-Bu |
| 214 | H | Me | $PrSO_2$ | $CH_2CH_2$ | O-c-Bu |
| 215 | Me | Me | $PrSO_2$ | $CH_2CH_2$ | O-c-Bu |
| 216 | H | H | $PhSO_2$ | $CH_2CH_2$ | O-c-Bu |
| 217 | H | Me | $PhSO_2$ | $CH_2CH_2$ | O-c-Bu |
| 218 | Me | Me | $PhSO_2$ | $CH_2CH_2$ | O-c-Bu |
| 219 | H | H | 4-Me—$PhSO_2$ | $CH_2CH_2$ | O-c-Bu |
| 220 | H | Me | 4-Me—$PhSO_2$ | $CH_2CH_2$ | O-c-Bu |
| 221 | Me | Me | 4-Me—$PhSO_2$ | $CH_2CH_2$ | O-c-Bu |
| 222 | H | H | Bz | $CH_2CH_2$ | O-c-Pr |
| 223 | H | Me | Bz | $CH_2CH_2$ | O-c-Pr |
| 224 | Me | Me | Bz | $CH_2CH_2$ | O-c-Pr |
| 225 | H | H | $PhC(O)CH_2$ | $CH_2CH_2$ | O-c-Pr |
| 226 | H | Me | $PhC(O)CH_2$ | $CH_2CH_2$ | O-c-Pr |
| 227 | Me | Me | $PhC(O)CH_2$ | $CH_2CH_2$ | O-c-Pr |
| 228 | H | H | 4-Me—Bz | $CH_2CH_2$ | O-c-Pr |
| 229 | H | Me | 4-Me—Bz | $CH_2CH_2$ | O-c-Pr |
| 230 | Me | Me | 4-Me—Bz | $CH_2CH_2$ | O-c-Pr |
| 231 | H | H | $MeSO_2$ | $CH_2CH_2$ | O-c-Pr |
| 232 | H | Me | $MeSO_2$ | $CH_2CH_2$ | O-c-Pr |

TABLE 2-continued

Compounds of the formula (I) according to the invention in which the substituents and symbols have the following meanings:

$R^2 = Cl$  $R^3 = SO_2Me$  $R^4 = H$
$R^5 = H$  $R^6 = OR^{12}$  $R^7 = R^{7a}, R^{7b}$
$Y = CH_2$  $Z = CH_2$  $v = 1$
$w = 2$

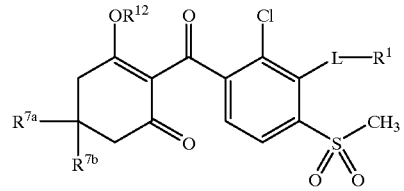

| No. | $R^{7a}$ | $R^{7b}$ | $R^{12}$ | L | $R^1$ |
|---|---|---|---|---|---|
| 233 | Me | Me | MeSO$_2$ | CH$_2$CH$_2$ | O-c-Pr |
| 234 | H | H | EtSO$_2$ | CH$_2$CH$_2$ | O-c-Pr |
| 235 | H | Me | EtSO$_2$ | CH$_2$CH$_2$ | O-c-Pr |
| 236 | Me | Me | EtSO$_2$ | CH$_2$CH$_2$ | O-c-Pr |
| 237 | H | H | PrSO$_2$ | CH$_2$CH$_2$ | O-c-Pr |
| 238 | H | Me | PrSO$_2$ | CH$_2$CH$_2$ | O-c-Pr |
| 239 | Me | Me | PrSO$_2$ | CH$_2$CH$_2$ | O-c-Pr |
| 240 | H | H | PhSO$_2$ | CH$_2$CH$_2$ | O-c-Pr |
| 241 | H | Me | PhSO$_2$ | CH$_2$CH$_2$ | O-c-Pr |
| 242 | Me | Me | PhSO$_2$ | CH$_2$CH$_2$ | O-c-Pr |
| 243 | H | H | 4-Me—PhSO$_2$ | CH$_2$CH$_2$ | O-c-Pr |
| 244 | H | Me | 4-Me—PhSO$_2$ | CH$_2$CH$_2$ | O-c-Pr |
| 245 | Me | Me | 4-Me—PhSO$_2$ | CH$_2$CH$_2$ | O-c-Pr |
| 246 | H | H | Bz | CH$_2$CH$_2$ | OCH$_2$CF$_3$ |
| 247 | H | Me | Bz | CH$_2$CH$_2$ | OCH$_2$CF$_3$ |
| 248 | Me | Me | Bz | CH$_2$CH$_2$ | OCH$_2$CF$_3$ |
| 249 | H | H | PhC(O)CH$_2$ | CH$_2$CH$_2$ | OCH$_2$CF$_3$ |
| 250 | H | Me | PhC(O)CH$_2$ | CH$_2$CH$_2$ | OCH$_2$CF$_3$ |
| 251 | Me | Me | PhC(O)CH$_2$ | CH$_2$CH$_2$ | OCH$_2$CF$_3$ |
| 252 | H | H | 4-Me—Bz | CH$_2$CH$_2$ | OCH$_2$CF$_3$ |
| 253 | H | Me | 4-Me—Bz | CH$_2$CH$_2$ | OCH$_2$CF$_3$ |
| 254 | Me | Me | 4-Me—Bz | CH$_2$CH$_2$ | OCH$_2$CF$_3$ |
| 255 | H | H | MeSO$_2$ | CH$_2$CH$_2$ | OCH$_2$CF$_3$ |
| 256 | H | Me | MeSO$_2$ | CH$_2$CH$_2$ | OCH$_2$CF$_3$ |
| 257 | Me | Me | MeSO$_2$ | CH$_2$CH$_2$ | OCH$_2$CF$_3$ |
| 258 | H | H | EtSO$_2$ | CH$_2$CH$_2$ | OCH$_2$CF$_3$ |
| 259 | H | Me | EtSO$_2$ | CH$_2$CH$_2$ | OCH$_2$CF$_3$ |
| 260 | Me | Me | EtSO$_2$ | CH$_2$CH$_2$ | OCH$_2$CF$_3$ |
| 261 | H | H | PrSO$_2$ | CH$_2$CH$_2$ | OCH$_2$CF$_3$ |
| 262 | H | Me | PrSO$_2$ | CH$_2$CH$_2$ | OCH$_2$CF$_3$ |
| 263 | Me | Me | PrSO$_2$ | CH$_2$CH$_2$ | OCH$_2$CF$_3$ |
| 264 | H | H | PhSO$_2$ | CH$_2$CH$_2$ | OCH$_2$CF$_3$ |
| 265 | H | Me | PhSO$_2$ | CH$_2$CH$_2$ | OCH$_2$CF$_3$ |
| 266 | Me | Me | PhSO$_2$ | CH$_2$CH$_2$ | OCH$_2$CF$_3$ |
| 267 | H | H | 4-Me—PhSO$_2$ | CH$_2$CH$_2$ | OCH$_2$CF$_3$ |
| 268 | H | Me | 4-Me—PhSO$_2$ | CH$_2$CH$_2$ | OCH$_2$CF$_3$ |
| 269 | Me | Me | 4-Me—PhSO$_2$ | CH$_2$CH$_2$ | OCH$_2$CF$_3$ |
| 270 | H | H | Bz | CH$_2$CH$_2$ | O-c-hexyl |
| 271 | H | Me | Bz | CHMe | O-c-hexyl |
| 272 | Me | Me | Bz | CHMe | O-c-hexyl |
| 273 | H | H | PhC(O)CH$_2$ | CHMe | O-c-hexyl |
| 274 | H | Me | PhC(O)CH$_2$ | CHMe | O-c-hexyl |
| 275 | Me | Me | PhC(O)CH$_2$ | CHMe | O-c-hexyl |
| 276 | H | H | 4-Me—Bz | CHMe | O-c-hexyl |
| 277 | H | Me | 4-Me—Bz | CHMe | O-c-hexyl |
| 278 | Me | Me | 4-Me—Bz | CHMe | O-c-hexyl |
| 279 | H | H | MeSO$_2$ | CHMe | O-c-hexyl |
| 280 | H | Me | MeSO$_2$ | CHMe | O-c-hexyl |
| 281 | Me | Me | MeSO$_2$ | CHMe | O-c-hexyl |
| 282 | H | H | EtSO$_2$ | CHMe | O-c-hexyl |
| 283 | H | Me | EtSO$_2$ | CHMe | O-c-hexyl |
| 284 | Me | Me | EtSO$_2$ | CHMe | O-c-hexyl |
| 285 | H | H | PrSO$_2$ | CHMe | O-c-hexyl |
| 286 | H | Me | PrSO$_2$ | CHMe | O-c-hexyl |
| 287 | Me | Me | PrSO$_2$ | CHMe | O-c-hexyl |
| 288 | H | H | PhSO$_2$ | CHMe | O-c-hexyl |
| 289 | H | Me | PhSO$_2$ | CHMe | O-c-hexyl |
| 290 | Me | Me | PhSO$_2$ | CHMe | O-c-hexyl |

TABLE 2-continued

Compounds of the formula (I) according to the invention in which the substituents and symbols have the following meanings:

$R^2 = Cl$  $R^3 = SO_2Me$  $R^4 = H$
$R^5 = H$  $R^6 = OR^{12}$  $R^7 = R^{7a}, R^{7b}$
$Y = CH_2$  $Z = CH_2$  $v = 1$
$w = 2$

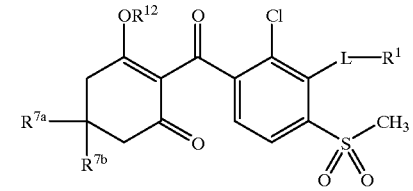

| No. | $R^{7a}$ | $R^{7b}$ | $R^{12}$ | L | $R^1$ |
|---|---|---|---|---|---|
| 291 | H | H | 4-Me—PhSO$_2$ | CHMe | O-c-hexyl |
| 292 | H | Me | 4-Me—PhSO$_2$ | CHMe | O-c-hexyl |
| 293 | Me | Me | 4-Me—PhSO$_2$ | CHMe | O-c-hexyl |
| 294 | H | H | Bz | CHMe | O-c-pentyl |
| 295 | H | Me | Bz | CHMe | O-c-pentyl |
| 296 | Me | Me | Bz | CHMe | O-c-pentyl |
| 297 | H | H | PhC(O)CH$_2$ | CHMe | O-c-pentyl |
| 298 | H | Me | PhC(O)CH$_2$ | CHMe | O-c-pentyl |
| 299 | Me | Me | PhC(O)CH$_2$ | CHMe | O-c-pentyl |
| 300 | H | H | 4-Me—Bz | CHMe | O-c-pentyl |
| 301 | H | Me | 4-Me—Bz | CHMe | O-c-pentyl |
| 302 | Me | Me | 4-Me—Bz | CHMe | O-c-pentyl |
| 303 | H | H | MeSO$_2$ | CHMe | O-c-pentyl |
| 304 | H | Me | MeSO$_2$ | CHMe | O-c-pentyl |
| 305 | Me | Me | MeSO$_2$ | CHMe | O-c-pentyl |
| 306 | H | H | EtSO$_2$ | CHMe | O-c-pentyl |
| 307 | H | Me | EtSO$_2$ | CHMe | O-c-pentyl |
| 308 | Me | Me | EtSO$_2$ | CHMe | O-c-pentyl |
| 309 | H | H | PrSO$_2$ | CHMe | O-c-pentyl |
| 310 | H | Me | PrSO$_2$ | CHMe | O-c-pentyl |
| 311 | Me | Me | PrSO$_2$ | CHMe | O-c-pentyl |
| 312 | H | H | PhSO$_2$ | CHMe | O-c-pentyl |
| 313 | H | Me | PhSO$_2$ | CHMe | O-c-pentyl |
| 314 | Me | Me | PhSO$_2$ | CHMe | O-c-pentyl |
| 315 | H | H | 4-Me—PhSO$_2$ | CHMe | O-c-pentyl |
| 316 | H | Me | 4-Me—PhSO$_2$ | CHMe | O-c-pentyl |
| 317 | Me | Me | 4-Me—PhSO$_2$ | CHMe | O-c-pentyl |
| 318 | H | H | Bz | CHMe | O-c-Bu |
| 319 | H | Me | Bz | CHMe | O-c-Bu |
| 320 | Me | Me | Bz | CHMe | O-c-Bu |
| 321 | H | H | PhC(O)CH$_2$ | CHMe | O-c-Bu |
| 322 | H | Me | PhC(O)CH$_2$ | CHMe | O-c-Bu |
| 323 | Me | Me | PhC(O)CH$_2$ | CHMe | O-c-Bu |
| 324 | H | H | 4-Me—Bz | CHMe | O-c-Bu |
| 325 | H | Me | 4-Me—Bz | CHMe | O-c-Bu |
| 326 | Me | Me | 4-Me—Bz | CHMe | O-c-Bu |
| 327 | H | H | MeSO$_2$ | CHMe | O-c-Bu |
| 328 | H | Me | MeSO$_2$ | CHMe | O-c-Bu |
| 329 | Me | Me | MeSO$_2$ | CHMe | O-c-Bu |
| 330 | H | H | EtSO$_2$ | CHMe | O-c-Bu |
| 331 | H | Me | EtSO$_2$ | CHMe | O-c-Bu |
| 332 | Me | Me | EtSO$_2$ | CHMe | O-c-Bu |
| 333 | H | H | PrSO$_2$ | CHMe | O-c-Bu |
| 334 | H | Me | PrSO$_2$ | CHMe | O-c-Bu |
| 335 | Me | Me | PrSO$_2$ | CHMe | O-c-Bu |
| 336 | H | H | PhSO$_2$ | CHMe | O-c-Bu |
| 337 | H | Me | PhSO$_2$ | CHMe | O-c-Bu |
| 338 | Me | Me | PhSO$_2$ | CHMe | O-c-Bu |
| 339 | H | H | 4-Me—PhSO$_2$ | CHMe | O-c-Bu |
| 340 | H | Me | 4-Me—PhSO$_2$ | CHMe | O-c-Bu |
| 341 | Me | Me | 4-Me—PhSO$_2$ | CHMe | O-c-Bu |
| 342 | H | H | Bz | CHMe | O-c-Pr |
| 343 | H | Me | Bz | CHMe | O-c-Pr |
| 344 | Me | Me | Bz | CHMe | O-c-Pr |
| 345 | H | H | PhC(O)CH$_2$ | CHMe | O-c-Pr |
| 346 | H | Me | PhC(O)CH$_2$ | CHMe | O-c-Pr |
| 347 | Me | Me | PhC(O)CH$_2$ | CHMe | O-c-Pr |
| 348 | H | H | 4-Me—Bz | CHMe | O-c-Pr |

TABLE 2-continued

Compounds of the formula (I) according to the invention in which the substituents and symbols have the following meanings:

$R^2 = Cl$  $R^3 = SO_2Me$  $R^4 = H$
$R^5 = H$  $R^6 = OR^{12}$  $R^7 = R^{7a}, R^{7b}$
$Y = CH_2$  $Z = CH_2$  $v = 1$
$w = 2$

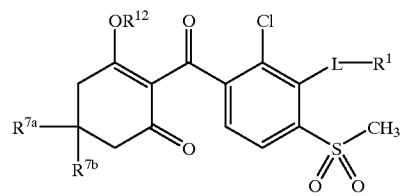

| No. | $R^{7a}$ | $R^{7b}$ | $R^{12}$ | L | $R^1$ |
|---|---|---|---|---|---|
| 349 | H | Me | 4-Me—Bz | CHMe | O-c-Pr |
| 350 | Me | Me | 4-Me—Bz | CHMe | O-c-Pr |
| 351 | H | H | MeSO$_2$ | CHMe | O-c-Pr |
| 352 | H | Me | MeSO$_2$ | CHMe | O-c-Pr |
| 353 | Me | Me | MeSO$_2$ | CHMe | O-c-Pr |
| 354 | H | H | EtSO$_2$ | CHMe | O-c-Pr |
| 355 | H | Me | EtSO$_2$ | CHMe | O-c-Pr |
| 356 | Me | Me | EtSO$_2$ | CHMe | O-c-Pr |
| 357 | H | H | PrSO$_2$ | CHMe | O-c-Pr |
| 358 | H | Me | PrSO$_2$ | CHMe | O-c-Pr |
| 359 | Me | Me | PrSO$_2$ | CHMe | O-c-Pr |
| 360 | H | H | PhSO$_2$ | CHMe | O-c-Pr |
| 361 | H | Me | PhSO$_2$ | CHMe | O-c-Pr |
| 362 | Me | Me | PhSO$_2$ | CHMe | O-c-Pr |
| 363 | H | H | 4-Me—PhSO$_2$ | CHMe | O-c-Pr |
| 364 | H | Me | 4-Me—PhSO$_2$ | CHMe | O-c-Pr |
| 365 | Me | Me | 4-Me—PhSO$_2$ | CHMe | O-c-Pr |
| 366 | H | H | Bz | CHMe | OCH$_2$CF$_3$ |
| 367 | H | Me | Bz | CHMe | OCH$_2$CF$_3$ |
| 368 | Me | Me | Bz | CHMe | OCH$_2$CF$_3$ |

TABLE 2-continued

Compounds of the formula (I) according to the invention in which the substituents and symbols have the following meanings:

$R^2 = Cl$  $R^3 = SO_2Me$  $R^4 = H$
$R^5 = H$  $R^6 = OR^{12}$  $R^7 = R^{7a}, R^{7b}$
$Y = CH_2$  $Z = CH_2$  $v = 1$
$w = 2$

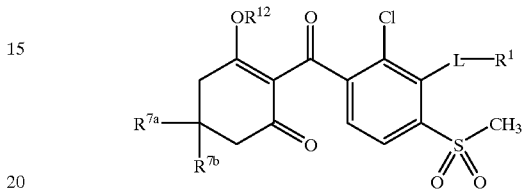

| No. | $R^{7a}$ | $R^{7b}$ | $R^{12}$ | L | $R^1$ |
|---|---|---|---|---|---|
| 369 | H | H | PhC(O)CH$_2$ | CHMe | OCH$_2$CF$_3$ |
| 370 | H | Me | PhC(O)CH$_2$ | CHMe | OCH$_2$CF$_3$ |
| 371 | Me | Me | PhC(O)CH$_2$ | CHMe | OCH$_2$CF$_3$ |
| 372 | H | H | 4-Me—Bz | CHMe | OCH$_2$CF$_3$ |
| 373 | H | Me | 4-Me—Bz | CHMe | OCH$_2$CF$_3$ |
| 374 | Me | Me | 4-Me—Bz | CHMe | OCH$_2$CF$_3$ |
| 375 | H | H | MeSO$_2$ | CHMe | OCH$_2$CF$_3$ |
| 376 | H | Me | MeSO$_2$ | CHMe | OCH$_2$CF$_3$ |
| 377 | Me | Me | MeSO$_2$ | CHMe | OCH$_2$CF$_3$ |
| 378 | H | H | EtSO$_2$ | CHMe | OCH$_2$CF$_3$ |
| 379 | H | Me | EtSO$_2$ | CHMe | OCH$_2$CF$_3$ |
| 380 | Me | Me | EtSO$_2$ | CHMe | OCH$_2$CF$_3$ |
| 381 | H | H | PrSO$_2$ | CHMe | OCH$_2$CF$_3$ |
| 382 | H | Me | PrSO$_2$ | CHMe | OCH$_2$CF$_3$ |
| 383 | Me | Me | PrSO$_2$ | CHMe | OCH$_2$CF$_3$ |
| 384 | H | H | PhSO$_2$ | CHMe | OCH$_2$CF$_3$ |
| 385 | H | Me | PhSO$_2$ | CHMe | OCH$_2$CF$_3$ |
| 386 | Me | Me | PhSO$_2$ | CHMe | OCH$_2$CF$_3$ |
| 387 | H | H | 4-Me—PhSO$_2$ | CHMe | OCH$_2$CF$_3$ |
| 388 | H | Me | 4-Me—PhSO$_2$ | CHMe | OCH$_2$CF$_3$ |
| 389 | Me | Me | 4-Me—PhSO$_2$ | CHMe | OCH$_2$CF$_3$ |

TABLE 3

Compounds of the formula (I) according to the invention in which the substituents and symbols have the following meanings:

$R^2 = Cl$  $R^3 = SO_2Et$  $R^4 = H$
$R^5 = H$  $R^6 = OH$  $Y = CH_2$
$Z = CH_2$  $v = 1$  $w = 0$

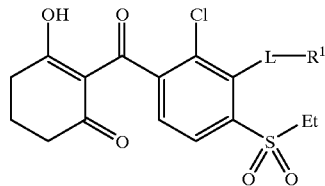

| No. | L | R¹ | Physical data |
|-----|---|-----|---------------|
| 390 | CH₂ | OCH₂CHF₂ | $^1$H NMR (CDCl$_3$): δ 1.25(t, 3H), 2.05(m, 2H), 2.45(m, 2H), 2.85(m, 2H), 3.98(q, 2H), 3.95(m, 2H), 5.25(s, 2H), 5.9(m, 1H), 7.3(d, 1H), 8.15(d, 1H), 16.7(s, 1H) |
| 391 | CH₂ | OCH₂CF₃ | $^1$H NMR (CDCl$_3$): δ 1.3(t, 3H), 2.05(m, 2H), 2.45(m, 2H), 2.85(m, 2H), 3.38(q, 2H), 4.0(q, 2H), 5.35(s, 2H), 7.32(d, 1H), 8.08(d, 1H), 16.75(s, 1H) |
| 392 | CH₂ | OCH₂CH₂Cl | $^1$H NMR (CDCl$_3$): δ 1.3(t, 3H), 2.05(m, 2H), 2.45(m, 2H), 2.85(m, 2H), 3.45(q, 2H), 3.65(t, 2H), 3.78(t, 2H), 5.35(s, 2H), 7.32(d, 2H), 8.1(d, 1H), 16.7(s, 1H) |
| 393 | CH₂ | SCH₂CF₃ | $^1$H NMR (CDCl$_3$): δ 1.3(t, 3H), 2.05(m, 2H), 2.45(m, 2H), 2.82(m, 2H), 3.35(m, 2H), 3.42(q, 2H), 4.62(s, 2H), 7.25(d, 1H), 8.05(d, 1H), 16.75(s, 1H) |
| 394 | CH₂ | OCH₂CH₂Br | |
| 395 | CH₂ | OCH₂CH₂F | |
| 396 | CH₂ | OCH₂CF₂CF₂H | |
| 397 | CH₂ | OCH₂CF₂CF₃ | |
| 398 | CH₂ | OCH₂CF₂CF₂CF₃ | |
| 399 | CH₂CH₂ | OCH₂CH₂Br | |
| 400 | CH₂CH₂ | OCH₂CH₂F | |
| 401 | CH₂CH₂ | OCH₂CF₂CF₂H | |
| 402 | CH₂CH₂ | OCH₂CF₂CF₃ | |
| 403 | CH₂CH₂ | OCH₂CF₂CF₂CF₃ | |
| 404 | CHMe | OCH₂CH₂Br | |
| 405 | CHMe | OCH₂CH₂F | |
| 406 | CHMe | OCH₂CF₂CF₂H | |
| 407 | CHMe | OCH₂CF₂CF₃ | |
| 408 | CHMe | OCH₂CF₂CF₂CF₃ | |
| 409 | CH₂ | O-c-Bu | |
| 410 | CH₂ | O-c-pentyl | |
| 411 | CH₂ | O-c-hexyl | |
| 412 | CH₂ | (tetrahydrofuran-2-ylmethoxy) | |
| 413 | CH₂ | (tetrahydropyran-2-ylmethoxy) | |
| 414 | CH₂ | O(CH₂)₂O(CH₂)₂OMe | |
| 415 | CH₂ | O(CH₂)₂O(CH₂)₂OEt | |
| 416 | CH₂ | O(CH₂)₂O(CH₂)₂O-i-Pr | |
| 417 | CH₂ | O(CH₂)₂O(CH₂)₂OCH₂CH=CH₂ | |
| 418 | CH₂CH₂ | O-c-Bu | |
| 419 | CH₂CH₂ | O-c-pentyl | |
| 420 | CH₂CH₂ | O-c-hexyl | |
| 421 | CH₂CH₂ | (tetrahydrofuran-2-ylmethoxy) | |

| 422 | CH₂CH₂ | 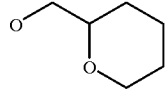 |
|---|---|---|
| 423 | CH₂CH₂ | O(CH₂)₂O(CH₂)₂OMe |
| 424 | CH₂CH₂ | O(CH₂)₂O(CH₂)₂OEt |
| 425 | CH₂CH₂ | O(CH₂)₂O(CH₂)₂O-i-Pr |
| 426 | CH₂CH₂ | O(CH₂)₂O(CH₂)₂OCH₂CH=CH₂ |
| 427 | CHMe | O-c-Bu |
| 428 | CHMe | O-c-pentyl |
| 429 | CHMe | O-c-hexyl |
| 430 | CHMe | 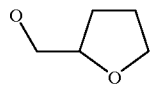 |
| 431 | CHMe | 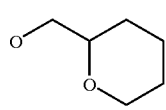 |
| 432 | CHMe | O(CH₂)₂O(CH₂)₂OMe |
| 433 | CHMe | O(CH₂)₂O(CH₂)₂OEt |
| 434 | CHMe | O(CH₂)₂O(CH₂)₂O-i-Pr |
| 435 | CHMe | O(CH₂)₂O(CH₂)₂OCH₂CH=CH₂ |

TABLE 4

Compounds of the formula (I) according to the invention in which the substituents and symbols have the following meanings:

$R^4 = H$   $R^5 = H$   $R^6 = OH$
$L = CH_2$   $Y = CH_2$   $Z = CH_2$
$v = 1$   $w = 0$

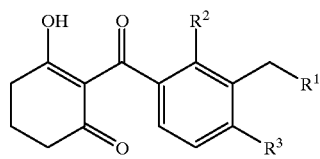

| No. | R¹ | R² | R³ |
|---|---|---|---|
| 436 | OCH₂CF₃ | Me | SO₂Me |
| 437 | OCH₂CF₃ | Me | SO₂Et |
| 438 | OCH₂CF₃ | SO₂Me | Cl |
| 439 | OCH₂CF₃ | SO₂Et | Cl |
| 440 | OCH₂CF₃ | SO₂Me | CF₃ |
| 441 | OCH₂CF₃ | SOMe | CF₃ |
| 442 | OCH₂CF₃ | SMe | CF₃ |
| 443 | OCH₂CF₃ | Cl | Cl |
| 444 | OCH₂CF₃ | Br | Br |
| 445 | OCH₂CF₂CF₂H | Me | SO₂Me |
| 446 | OCH₂CF₂CF₂H | Me | SO₂Et |
| 447 | OCH₂CF₂CF₂H | SO₂Me | Cl |
| 448 | OCH₂CF₂CF₂H | SO₂Et | Cl |
| 449 | OCH₂CF₂CF₂H | SO₂Me | CF₃ |
| 450 | OCH₂CF₂CF₂H | SOMe | CF₃ |
| 451 | OCH₂CF₂CF₂H | SMe | CF₃ |
| 452 | OCH₂CF₂CF₂H | Cl | Cl |
| 453 | OCH₂CF₂CF₂H | Br | Br |
| 454 | OCH₂CF₂CF₃ | Me | SO₂Me |
| 455 | OCH₂CF₂CF₃ | Me | SO₂Et |
| 456 | OCH₂CF₂CF₃ | SO₂Me | Cl |
| 457 | OCH₂CF₂CF₃ | SO₂Et | Cl |
| 458 | OCH₂CF₂CF₃ | SO₂Me | CF₃ |
| 459 | OCH₂CF₂CF₃ | SOMe | CF₃ |
| 460 | OCH₂CF₂CF₃ | SMe | CF₃ |
| 461 | OCH₂CF₂CF₃ | Cl | Cl |
| 462 | OCH₂CF₂CF₃ | Br | Br |
| 463 | OCH₂CH₂Cl | Me | SO₂Me |
| 464 | OCH₂CH₂Cl | Me | SO₂Et |
| 465 | OCH₂CH₂Cl | SO₂Me | Cl |
| 466 | OCH₂CH₂Cl | SO₂Et | Cl |
| 467 | OCH₂CH₂Cl | SO₂Me | CF₃ |
| 468 | OCH₂CH₂Cl | SOMe | CF₃ |
| 469 | OCH₂CH₂Cl | SMe | CF₃ |
| 470 | OCH₂CH₂Cl | Cl | Cl |
| 471 | OCH₂CH₂Cl | Br | Br |
| 472 | (tetrahydrofuran-2-ylmethoxy) | Me | SO₂Me |
| 473 | (tetrahydrofuran-2-ylmethoxy) | Me | SO₂Et |
| 474 | (tetrahydrofuran-2-ylmethoxy) | SO₂Me | Cl |

TABLE 4-continued

Compounds of the formula (I) according to the invention in which the substituents and symbols have the following meanings:

$R^4 = H$     $R^5 = H$     $R^6 = OH$
$L = CH_2$     $Y = CH_2$     $Z = CH_2$
$v = 1$     $w = 0$

| No. | $R^1$ | $R^2$ | $R^3$ |
|---|---|---|---|
| 475 | (tetrahydrofuran-2-ylmethoxy) | SO₂Et | Cl |
| 476 | (tetrahydrofuran-2-ylmethoxy) | SO₂Me | CF₃ |
| 477 | (tetrahydrofuran-2-ylmethoxy) | SOMe | CF₃ |
| 478 | (tetrahydrofuran-2-ylmethoxy) | SMe | CF₃ |
| 479 | (tetrahydrofuran-2-ylmethoxy) | Cl | Cl |
| 480 | (tetrahydrofuran-2-ylmethoxy) | Br | Br |
| 481 | O(CH₂)₂O(CH₂)₂OMe | Me | SO₂Me |
| 482 | O(CH₂)₂O(CH₂)₂OMe | Me | SO₂Et |
| 483 | O(CH₂)₂O(CH₂)₂OMe | SO₂Me | Cl |
| 484 | O(CH₂)₂O(CH₂)₂OMe | SO₂Et | Cl |
| 485 | O(CH₂)₂O(CH₂)₂OMe | SO₂Me | CF₃ |
| 486 | O(CH₂)₂O(CH₂)₂OMe | SOMe | CF₃ |
| 487 | O(CH₂)₂O(CH₂)₂OMe | SMe | CF₃ |
| 488 | O(CH₂)₂O(CH₂)₂OMe | Cl | Cl |
| 489 | O(CH₂)₂O(CH₂)₂OMe | Br | Br |
| 490 | O(CH₂)₂O(CH₂)₂OEt | Me | SO₂Me |
| 491 | O(CH₂)₂O(CH₂)₂OEt | Me | SO₂Et |
| 492 | O(CH₂)₂O(CH₂)₂OEt | SO₂Me | Cl |
| 493 | O(CH₂)₂O(CH₂)₂OEt | SO₂Et | Cl |
| 494 | O(CH₂)₂O(CH₂)₂OEt | SO₂Me | CF₃ |
| 495 | O(CH₂)₂O(CH₂)₂OEt | SOMe | CF₃ |
| 496 | O(CH₂)₂O(CH₂)₂OEt | SMe | CF₃ |
| 497 | O(CH₂)₂O(CH₂)₂OEt | Cl | Cl |
| 498 | O(CH₂)₂O(CH₂)₂OEt | Br | Br |
| 499 | OCH₂CH₂F | Me | SO₂Me |
| 500 | OCH₂CH₂F | Me | SO₂Et |
| 501 | OCH₂CH₂F | SO₂Me | Cl |
| 502 | OCH₂CH₂F | SO₂Et | Cl |
| 503 | OCH₂CH₂F | SO₂Me | CF₃ |
| 504 | OCH₂CH₂F | SOMe | CF₃ |
| 505 | OCH₂CH₂F | SMe | CF₃ |
| 506 | OCH₂CH₂F | Cl | Cl |
| 507 | OCH₂CH₂F | Br | Br |
| 508 | OCH₂CH₂Br | Me | SO₂Me |
| 509 | OCH₂CH₂Br | Me | SO₂Et |
| 510 | OCH₂CH₂Br | SO₂Me | Cl |
| 511 | OCH₂CH₂Br | SO₂Et | Cl |
| 512 | OCH₂CH₂Br | SO₂Me | CF₃ |
| 513 | OCH₂CH₂Br | SOMe | CF₃ |
| 514 | OCH₂CH₂Br | SMe | CF₃ |
| 515 | OCH₂CH₂Br | Cl | Cl |
| 516 | OCH₂CH₂Br | Br | Br |

TABLE 5

Compounds of the formula (I) according to the invention in which the substituents and symbols have the following meanings:

$R^2 = Cl$     $R^3 = SO_2Et$     $R^4 = H$
$R^5 = H$     $R^6 = OH$     $Y = CH_2$
$Z = CH_2$     $v = 1$     $w = 0$ (Note: structure shows $R^3 = SO_2Me$ and $R^2 = Cl$ on the aryl ring)

| No. | $R^1$ | $R^{7a}, R^{7b}$ | Physical data |
|---|---|---|---|
| 517 | O-c-pentyl | Me, Me | ¹H NMR (CDCl₃): δ 1.5–1.9(m, 8H), 2.1 (s, 6H), 2.42(t, 2H), 2.65(t, 2H), 3.3 (s, 3H), 4.15 (m, 1H), 5.05 (s, 2H), 7.28 (d, 1H), (d, 1H), 8.15(d, 1H) |
| 518 | OCH₂CF₃ | Me, Me | |
| 519 | OCH₂CF₂H | Me, Me | |
| 520 | OCH₂CH₂F | Me, Me | |
| 521 | OCH₂CH₂Cl | Me, Me | |
| 522 | OCH₂CH₂Br | Me, Me | |
| 523 | OCH₂CF₃ | Me, Me | |
| 524 | (tetrahydrofuran-3-ylmethoxy) | Me, Me | |
| 525 | O(CH₂)₂O(CH₂)₂O(CH₂)₂OMe | Me, Me | |
| 526 | O(CH₂)₂O(CH₂)₂O(CH₂)₂OEt | Me, Me | |
| 527 | O(CH₂)₂O(CH₂)₂OMe | Me, Me | |
| 528 | O(CH₂)₂O(CH₂)₂OEt | Me, Me | |
| 529 | c-Bu | Me, Me | |
| 530 | c-hexyl | Me, Me | |

TABLE 5-continued

Compounds of the formula (I) according to the invention in which the substituents and symbols have the following meanings:

$R^2$ = Cl   $R^3$ = $SO_2Et$   $R^4$ = H
$R^5$ = H    $R^6$ = OH         Y = $CH_2$
Z = $CH_2$   v = 1              w = 0

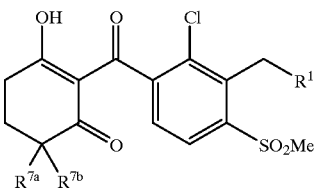

| No. | $R^1$ | $R^{7a}$, $R^{7b}$ | Physical data |
|---|---|---|---|
| 531 | O-c-pentyl | Et, Et | |
| 532 | $OCH_2CF_2I$ | Et, Et | |
| 533 | $OCH_2CF_2H$ | Et, Et | |
| 534 | $OCH_2CH_2F$ | Et, Et | |
| 535 | $OCH_2CH_2Cl$ | Et, Et | |
| 536 | $OCH_2CH_2Br$ | Et, Et | |
| 537 | $OCH_2CF_3$ | Et, Et | |
| 538 | (tetrahydrofuranyl-O-) | Et, Et | |
| 539 | $O(CH_2)_2O(CH_2)_2O(CH_2)_2OMe$ | Et, Et | |
| 540 | $O(CH_2)_2O(CH_2)_2O(CH_2)_2OEt$ | Et, Et | |
| 541 | $O(CH_2)_2O(CH_2)_2OMe$ | Et, Et | |
| 542 | $O(CH_2)_2O(CH_2)_2OEt$ | Et, Et | |
| 543 | c-Bu | Et, Et | |
| 544 | c-hexyl | Et, Et | |

B. FORMULATION EXAMPLES

1. Dusting Agents

A dusting agent is obtained by mixing 10 parts by weight of a compound of the formula (I) and 90 parts by weight of talc as inert substance and comminuting in a hammer mill.

2. Dispersible Powder

A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleylmethyltaurate as wetting agent and dispersant and grinding in a pinned-disk mill.

3. Dispersion Concentrate

A dispersion concentrate which is easily dispersible in water is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255 to over 277° C.) and grinding in a friction ball mill to a fineness of under 5 microns.

4. Emulsifiable Concentrate

An emulsifiable concentrate is obtained from 15 parts by weight of a compound of the formula (I), 75 parts by weight of cyclohexanone as solvent and 10 parts by weight of ethoxylated nonylphenol as emulsifier.

5. Water-dispersible Granules

Water-dispersible granules are obtained by mixing
75 parts by weight of a compound of the formula (I),
10 parts by weight of calcium lignosulfonate,
5 parts by weight of sodium laurylsulfate,
3 parts by weight of polyvinyl alcohol and
7 parts by weight of kaolin,
grinding in a pinned-disk mill and granulating the powder in a fluidized bed by spraying on water as a granulating fluid.

Water-dispersible granules are also obtained by homogenizing and precomminuting
25 parts by weight of a compound of the formula (I),
5 parts by weight of sodium 2,2'-dinaphthylmethane-6,6'-disulfonate,
2 parts by weight of sodium oleoylmethyltaurate,
1 parts by weight of polyvinyl alcohol,
17 parts by weight of calcium carbonate and
50 parts by weight of water
in a colloid mill, then grinding in a bead mill and atomizing and drying the suspension thus obtained in a spray tower by means of a single-substance nozzle.

C. BIOLOGICAL EXAMPLES

1. Weed Action Preemergence

Seeds of mono- and dicotyledonous weed plants are put into sandy loam soil in cardboard pots and covered with soil. The compounds according to the invention in the form of wettable powders or emulsion concentrates are then applied to the surface of the covering soil as an aqueous suspension or emulsion with a water application rate of 600 to 800 l/ha after conversion in a dose of 1 kg of active substance or less per hectare after conversion. After the treatment, the pots are placed in a greenhouse and kept under good growth conditions for the weeds. The visual assessment of the plants or emergence damage is carried out after the emergence of the test plants after a test period of 3 to 4 weeks in comparison with untreated controls. In this case, for example, the compounds of Example Nos. 5, 33 and 19 show an at least 80% action against Stellaria media, Lolium multiflorum and Amaranthus retroflexus. The compounds of Example Nos. 2 and 8 show an at least 90% action against Amaranthus retroflexus, Stellaria media and Setaria viridis. The compounds of Example Nos. 2 and 18 show a 100% action against Amaranthus retroflexus and Sinapis arvensis.

2. Weed Action Postemergence

Seeds of mono- and dicotyledonous weeds are put into sandy loam soil in cardboard pots, covered with soil and grown in the greenhouse under good growth conditions. Two to three weeks after sowing, the test plants are treated in the three-leaf stage. The compounds according to the invention formulated as wettable powders or as emulsion concentrates are sprayed onto the green parts of the plants in a dose of 1 kg of active substance or less per hectare after conversion with a water application rate of 600 to 800 l/ha after conversion. After a standing time of the test plants in the greenhouse under optimal growth conditions of 3 to 4 weeks, the action of the preparations is assessed in comparison with untreated controls. Postemergence, the compositions according to the invention also show a good herbicidal activity against a broad spectrum of economically important grass weeds and broad-leaved weeds. For example, the compounds of Example Nos. 20, 32, 33, 34 and 18 show an at least 80% action against Sinapis arvensis and Amaranthus retroflexus. The compounds of Example Nos. 2, 20, 33 and 34 show an at least 80% action against Stellaria media and Amaranthus retroflexus. The compounds of Example Nos. 2 and 18 show an at least 90% action against Sinapis arvensis and Stellaria media.

3. Action on Harmful Plants in Rice

Typical harmful plants in rice crops are grown in a greenhouse under paddy rice conditions (depth of the water:

2–3 cm). After the treatment with the formulated compounds according to the invention in a dose of 1 kg of active substance or less per hectare after conversion, the test plants are placed in the greenhouse under optimal growth conditions and kept in this way during the entire test period. About three weeks after application, evaluation is carried out by means of visual assessment of the plant damage in comparison with untreated controls. The compounds according to the invention have very good herbicidal action against harmful plants. In this case, for example, the compounds of Example Nos. 2, 8, 32 and 33 show an at least 80% action against Cyperus iria and Echinocloa crus-galli.

4. Crop Plant Tolerability

In further tests in the greenhouse, seeds of a relatively large number of crop plants and weeds are placed in sandy loam soil and covered with soil. Some of the pots are immediately treated as described in section 1, and the others are placed in the greenhouse until the plants have developed two to three true leaves and then sprayed with the substances of the formula (I) according to the invention in different doses as described in section 2. Four to five weeks after the application and standing time in the greenhouse, it is found by means of visual assessment that the compounds according to the invention as a rule leave dicotyledonous crops such as, for example, soybeans and sugar beet undamaged or almost undamaged pre- and postemergence even at high doses of active substance. Some substances moreover also spare graminaceous crops, such as, for example, barley, wheat and rice. In some cases, the compounds of the formula (1) show a high selectivity and are therefore suitable for the control of undesired vegetation in agricultural crops.

What is claimed is:

1. A benzoyl derivative of the formula (I),

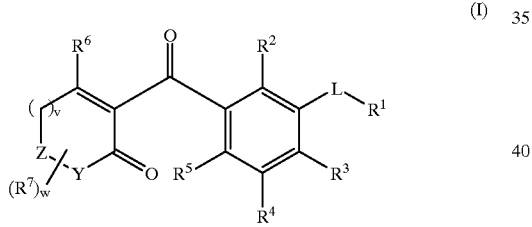

wherein:

$R^1$ is cycloalkyl, cycloalkenyl, aryl, cycloalkoxy, cycloalkylalkoxy, cycloalkylalkenyloxy, cycloalkylalkynyloxy, cycloalkenyloxy, cycloalkenylalkoxy, cycloalkenylalkenyloxy, cycloalkenylalkynyloxy, aryloxy, arylalkoxy, arylalkenyloxy, arylalkynyloxy, cycloalkylthio, cycloalkylalkylthio, cycloalkylalkenylthio, cycloalkylalkynylthio, cycloalkenylthio, cycloalkenylalkylthio, cycloalkenylalkenylthio, cycloalkenylalkynylthio, arylthio, arylalkylthio, arylalkenylthio, arylalkynylthio, optionally substituted mono- or diarylamino, optionally substituted mono- or diheteroarylamino, optionally substituted N-alkyl-N-arylamino, optionally substituted N-alkyl-N-heteroarylamino, cycloalkylamino, cycloalkenylamino, heterocyclylalkylamino, heterocyclylalkenylamino, cycloalkylsulfonyl, cycloalkylalkylsulfonyl, cycloalkylalkenylsulfonyl, cycloalkylalkynylsulfonyl, cycloalkenylsulfonyl, cycloalkenylalkylsulfonyl, cycloalkenylalkenylsulfonyl, cycloalkenylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, cycloalkylsulfinyl, cycloalkylalkylsulfinyl, cycloalkylalkenylsulfinyl, cycloalkylalkynylsulfinyl, cycloalkenylsulfinyl, cycloalkenylalkylsulfinyl, cycloalkenylalkenylsulfinyl, cycloalkenylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, heterocyclylalkylsulfinyl, heterocyclylalkenylsulfinyl, heterocyclylalkynylsulfinyl, aminosulfonyl, optionally substituted mono- or dialkylaminosulfonyl, optionally substituted mono- or diarylaminosulfonyl, optionally substituted mono- or diheteroarylaminosulfonyl, optionally substituted N-alkyl-N-arylaminosulfonyl, optionally substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, cycloalkenylsulfonyloxy, cycloalkenylalkylsulfonyloxy, cycloalkenylalkenylsulfonyloxy, cycloalkenylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfonylamino, cycloalkylalkenylsulfonylamino, cycloalkylalkynylsulfonylamino, cycloalkenylsulfonylamnino, cycloalkenylalkylsulfonylamino, cycloalkenylalkenylsulfonylamino, cycloalkenylalkynylsulfonylamino, arylsulfonylamino, arylalkylsulfonylamino, arylalkenylsulfonylamino, arylalkynylsulfonylamino, heteroarylsulfonylamino, heteroarylalkylsulfonylamino, heteroarylalkenylsulfonylamino, heteroarylalkynylsulfonylamino, alkylsulfonyl-N-alkylamino, alkenylsulfonyl-N-alkylamino, alkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, cycloalkenylsulfonyl-N-alkylarnino, cycloalkenylalkylsulfonyl-N-alkylarnino, cycloalkenylalkenylsulfonyl-N-alkylarnino, cycloalkenylalkynylsulfonyl-N-alkylamino, arylsulfonyl-N-alkylamino, heteroarylsulfonyl-N-alkylamino, arylalkylsulfonylamino, heteroarylalkylsulfonyl-N-alkylamino, arylalkenylsulfonyl-N-alkylamino, heteroarylalkenylsulfonyl-N-alkylamino, arylalkynylsulfonyl-N-alkylamino,
heteroarylalkynylsulfonyl-N-alkylamino,
heterocyclylsulfonyl-N-alkylamino,
heterocyclylalkylsulfonyl-N-alkylamino,
heterocyclylalkenylsulfonyl-N-alkylarnino,
heterocyclylalkynylsulfonyl-N-alkylarnino,
alkylcarbonyl, alkenylcarbonyl, alkynylcarbonyl,
cycloalkylcarbonyl, cycloalkylalkylcarbonyl,
cycloalkylalkenylcarbonyl, cycloalkylalkynylcarbonyl,
cycloalkenylcarbonyl, cycloalkenylalkylcarbonyl,
cycloalkenylalkenylcarbonyl,
cycloalkenylalkynylcarbonyl, arylcarbonyl,
arylalkylcarbonyl, arylalkenylcarbonyl,
arylalkynylcarbonyl, heteroarylcarbonyl,
heteroarylalkylcarbonyl, heteroarylalkenylcarbonyl,
heteroarylalkynylcarbonyl, heterocyclylcarbonyl,
carboxyl, alkoxycarbonyl, alkenyloxycarbonyl,
alkynyloxycarbonyl, cycloalkoxycarbonyl,
cycloalkylalkoxycarbonyl,
cycloalkylalkenyloxycarbonyl,
cycloalkylalkynyloxycarbonyl,
cycloalkenyloxycarbonyl,
cycloalkenylalkoxycarbonyl,
cycloalkenylalkenyloxycarbonyl,
cycloalkenylalkynyloxycarbonyl, aryloxycarbonyl,
arylalkoxycarbonyl, arylalkenyloxycarbonyl,
arylalkynyloxycarbonyl, heteroaryloxycarbonyl,
heteroarylalkoxycarbonyl,
heteroarylalkenyloxycarbonyl,
heteroarylalkynyloxycarbonyl,
heterocyclyloxycarbonyl, heterocyclylalkoxycarbonyl,
heterocyclylalkenyloxycarbonyl,
heterocyclylalkynyloxycarbonyl, aminocarbonyl,
optionally substituted mono- or dialkylaminocarbonyl,
optionally substituted mono- or diarylaminocarbonyl,
optionally substituted mono- or
diheteroarylaminocarbonyl, optionally substituted
N-alkyl-N-arylaminocarbonyl, optionally substituted
N-alkyl-N-heteroarylaminocarbonyl, optionally substituted mono- or diheteroarylaminocarbonyloxy, optionally substituted N-alkyl-N-arylaminocarbonyloxy,
optionally substituted N-alkyl-N-heteroarylaminocarbonyloxy, aminocarbonylamino,
optionally substituted mono- or
dialkylaminocarbonylamino, optionally substituted
mono- or diarylaminocarbonylamino, optionally substituted mono- or diheteroarylaminocarbonylamino,
optionally substituted N-alkyl-N-arylaminocarbonylamino, optionally substituted
N-alkyl-N-heteroarylaminocarbonylamino,
cycloalkylcarbonyloxy, cycloalkylalkylcarbonyloxy,
cycloalkylalkenylcarbonyloxy,
cycloalkylalkynylcarbonyloxy,
cycloalkenylcarbonyloxy,
cycloalkenylalkylcarbonyloxy,
cycloalkenylalkenylcarbonyloxy,
cycloalkenylalkynylcarbonyloxy, arylcarbonyloxy,
arylalkylcarbonyloxy, arylalkenylcarbonyloxy,
arylalkynylcarbonyloxy, heteroarylcarbonyloxy,
heteroarylalkylcarbonyloxy,
heteroarylalkenylcarbonyloxy,
heteroarylalkynylcarbonyloxy,
heterocyclylcarbonyloxy,
heterocyclylalkylcarbonyloxy,
heterocyclylalkenylcarbonyloxy,
heterocyclylalkynylcarbonyloxy, optionally substituted
mono- or dialkylcarbonylamino, optionally substituted
mono- or diarylcarbonylamino, optionally substituted
mono- or diheteroarylcarbonylamino, optionally substituted alkylcarbonyl-N-arylamino, optionally substituted arylcarbonyl-N-alkylamino, optionally substituted alkylcarbonyl-N-heteroarylamino, optionally substituted heteroarylcarbonyl-N-alkylamino,
alkoxycarbonylamino, alkenyloxycarbonylamino,
alkynyloxycarbonylamino,
cycloalkoxycarbonylamino,
cycloalkylalkoxycarbonylamino,
cycloalkylalkenyloxycarbonylamino,
cycloalkylalkynyloxycarbonylamino,
cycloalkenyloxycarbonylamino,
cycloalkenylalkoxycarbonylamino,
cycloalkenylalkenyloxycarbonylamino,
cycloalkenylalkynyloxycarbonylamino,
aryloxycarbonylamino, arylalkoxycarbonylamino,
arylalkenyloxycarbonylamino,
arylalkynyloxycarbonylamino,
heteroaryloxycarbonylamino,
heteroarylalkoxycarbonylamino,
heteroarylalkenyloxycarbonylamino,
heteroarylalkynyloxycarbonylamino,
heterocyclyloxycarbonylamino,
heterocyclylalkoxycarbonylamino,
heterocydylalkenyloxycarbonylamino,
heterocyclylalkynyloxycarbonylamino,
alkoxycarbonyloxy, alkenyloxycarbonyloxy,
alkynyloxycarbonyloxy, cycloalkoxycarbonyloxy,
cycloalkylalkoxycarbonyloxy,
cycloalkylalkenyloxycarbonyloxy,
cycloalkylalkynyloxycarbonyloxy,
cycloalkenyloxycarbonyloxy,
cycloalkenylalkoxycarbonyloxy,
cycloalkenylalkenyloxycarbonyloxy,
cycloalkenylalkynyloxycarbonyloxy,
aryloxycarbonyloxy, arylalkoxycarbonyloxy,
arylalkenyloxycarbonyloxy,
arylalkynyloxycarbonyloxy,
heteroaryloxycarbonyloxy,
heteroarylalkoxycarbonyloxy,
heteroarylalkenyloxycarbonyloxy,
heteroarylalkynyloxycarbonyloxy,
heterocyclyloxycarbonyloxy,
heterocyclylalkoxycarbonyloxy,
heterocyclylalkenyloxycarbonyloxy,
heterocyclylalkynyloxycarbonyloxy,
alkoxycarbonylamino, alkenyloxycarbonylamino,
alkynyloxycarbonyl-N-alkylamino,
cycloalkoxycarbonyl-N-alkylamino;
cycloalkylalkoxycarbonyl-N-alkylamino,
cycloalkylalkenyloxycarbonyl-N-alkylamnino,
cycloalkylalkynyloxycarbonyl-N-alkylamino,
cycloalkenyloxycarbonyl-N-alkylamino,
cycloalkenylalkoxycarbonyl-N-alkylamino,
cycloalkenylalkenyloxycarbonyl-N-alkylamino,
cycloalkenylalkynyloxycarbonyl-N-alkylamino,
aryloxycarbonyl-N-alkylamino, arylalkoxycarbonyl-N-alkylamino, arylalkenyloxycarbonyl-N-alkyl amino,
arylalkynyloxycarbonyl-N-alkylamino,
heteroarylalkoxycarbonyl-N-alkylamino,
heteroarylalkenyloxycarbonyl-N-alkylamino,
N-alkylheteroarylalkynyloxycarbonyl-N-alkylamino,
N-alkylheterocyclylalkoxycarbonyl-N-alkylamino,
heterocyclylalkenyloxycarbonyl-N-alkylamino,
heterocyclylalkynyloxycarbonyl-N-alkylamino,
formyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkylcarbonylamino, haloalkenylcarbonylamino, haloalkynylcarbonylamino, haloalkoxycarbonylamino, haloalkenyloxycarbonylamino, haloalkynyloxycarbonylamino, haloalkylcarbonyloxy, haloalkenylcarbonyloxy, haloalkynylcarbonyloxy, haloalkoxycarbonyloxy, haloalkenyloxycarbonyloxy, haloalkynyloxycarbonyloxy, haloalkylaminocarbonyloxy, haloalkenylaminocarbonylamino, haloalkynylaminocarbonylamino, cyano, —P(=O)R$^8$R$^9$, —P(=O)OR$^{10}$R$^8$, —P(=O)OR$^{10}$OR$^{11}$, 2-tetrahydrofuranylmethoxy, 3-tetrahydrofuranylmethoxy, 2-tetrahydrothienylmethoxy, 3-tetrahydrothienylmethoxy, 2-tetrahydropyranylnethoxy, it being possible for the radicals cycloalkyl, cycloalkenyl, aryl, tetrahydrofuranyl, tetrahydrothienyl, tetrahydropyranylmethoxy, heteroaryl and heterocyclyl to be optionally mono- or polysubstituted, identically or differently, by R$^2$, or one of the groups —O—(CH$_2$)$_m$—O—(CH$_2$)$_n$—R$^{2a}$, —O—CH$_2$—S—(O)P—R$^{13}$, —CONHNH—(CH$_2$)$_n$-alkyl and -CONHNH-(CH2)$_n$-aryl;

R$^{2a}$ is cycloalkyl, cycloalkenyl, cycloalkylalkyl, cycloalkylalkenyl, cycloalkylalkynyl, cycloalkenylalkyl, cycloalkenylalkyl, aryl, arylalkyl, arylalkenyl, arylalkynyl, heteroaryl, heteroarylalkyl, heteroarylalkenyl, heteroarylalkynyl, heterocyclyl, heterocyclylalkyl, heterocyclylalkenyl, heterocyclylalkynyl, hydroxyl, alkoxy, alkenyloxy, alkynyloxy, cycloalkoxy, cycloalkylalkoxy, cycloalkylalkenyloxy, cycloalkylalkynyloxy, cycloalkenyloxy, cycloalkenylalkoxy, cycloalkenylalkenyloxy, cycloalkenylalkynyloxy, aryloxy, arylalkoxy, arylalkenyloxy, arylalkynyloxy, heteroaryloxy, heteroarylalkoxy, heteroarylalkenyloxy, heteroarylalkynyloxy, heterocyclyloxy, heterocyclylalkoxy, heterocyclylalkenyloxy, heterocyclylalkynyloxy, thio, alkylthio, alkenylthio, alkynylthio, cycloalkylthio, cycloalkylalkylthio, cycloalkylalkenylthio, cycloalkylalkynylthio, cycloalkenylthio, cycloalkenylalkylthio, cycloalkenylalkenylthio, cycloalkenylalkynylthio, arylthio, arylalkylthio, arylalkenylthio, arylalkynylthio, heteroarylthio, heteroarylalkylthio, heteroarylalkenylthio, heteroarylalkynylthio, heterocyclylthio, heterocyclylalkylthio, heterocyclylalkenylthio, heterocyclylalkynylthio, amino, optionally substituted mono- or dialkylamino, optionally substituted mono- or diarylamino, optionally substituted mono- or diheteroarylamino, optionally substituted N-alkyl-N-arylamino, optionally substituted N-alkyl-N-heteroarylamino, alkenylamino, alkynylamino, cycloalkylamino, cycloalkenylamino, heterocyclylalkylamino, heterocyclylalkenylamino, alkylsulfonyl, alkenylsulfonyl, alkynylsulfonyl, cycloalkylsulfonyl, cycloalkylalkylsulfonyl, cycloalkylalkenylsulfonyl, cycloalkylalkynylsulfonyl, cycloalkenylsulfonyl, cycloalkenylalkylsulfonyl, cycloalkenylalkenylsulfonyl, cycloalkenylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, alkylsulfinyl, alkenylsulfinyl, alkynylsulfinyl, cycloalkylsulfinyl, cycloalkylalkylsulfinyl, cycloalkylalkenylsulfinyl, cycloalkylalkynylsulfinyl, cycloalkenylsulfinyl, cycloalkenylalkylsulfinyl, cycloalkenylalkenylsulfinyl, cycloalkenylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, heterocyclylalkylsulfinyl, heterocyclylalkenylsulfinyl, heterocyclylalkynylsulfinyl, aminosulfonyl, optionally substituted mono- or dialkylaminosulfonyl, optionally substituted mono- or diarylaminosulfonyl, optionally substituted mono- or diheteroarylaminosulfonyl, optionally substituted N-alkyl-N-arylaminosulfonyl, optionally substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, cycloalkenylsulfonyloxy, cycloalkenylalkylsulfonyloxy, cycloalkenylalkenylsulfonyloxy, cycloalkenylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfonylamino, cycloalkylalkenylsulfonylamino, cycloalkylalkynylsulfonylamnino, cycloalkenylalkylsulfonylamino, cycloalkenylalkenylsulfonylamino, cycloalkenylalkynylsulfonylamino, arylsulfonylamino, arylalkylsulfonylamino, arylalkenylsulfonylamino, arylalkynylsulfonylamino, heteroarylsulfonylamino, heteroarylalkylsulfonylamino, heteroarylalkenylsulfonylamino, heteroarylalkynylsulfonylamino, dialkylsulfonyl-N-alkylamino, alkenylsulfonyl-N-alkylamino, alkynyisulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, cycloalkenylsulfonyl-N-alkylamnino, cycloalkenylalkylsulfonyl-N-alkylamino, cycloalkenylalkenyisulfonyl-N-alkylamino, cycloalkenylalkynyisulfonyl-N-alkylamino, arylsulfonyl-N-alkylamino, heteroarylsulfonyl-N-alkylamino, arylalkylsulfonyl-N-alkylamino, heteroarylalkylsulfonyl-N-alkylamino, arylalkenylsulfonyl-N-alkylamino, heteroarylalkenylsulfonyl-N-alkylamino, arylalkynylsulfonyl-N-alkylamino, heteroarylalkynylsulfonyl-N-alkylamino, heterocyclylsulfonyl-N-alkylamino, heterocyclylalkylsulfonyl-N-alkylamino, heterocyclylalkenylsulfonyl-N-alkylamino, heterocyclylalkynylsulfonyl-N-alkylamino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, cycloalkenylcarbonyl, cycloalkenylalkylcarbonyl, cycloalkenylalkenylcarbonyl, cycloalkenylalkynylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, heterocyclylcarbonyl, heterocyclylalkyl, heterocyclylalkenyl, heterocyclylalkynyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, cycloalkenyloxycarbonyl, cycloalkenylalkoxycarbonyl, cycloalkenylalkenyloxycarbonyl, cycloalkenylalkynyloxycarbonyl, aryloxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, alkylcarbonyloxy, alkenylcarbonyloxy, alkynylcarbonyloxy, cycloalkylcarbonyloxy, cycloalkylalkenylcarbonyloxy, cycloalkylalkynylcarbonyloxy, cycloalkenylcarbonyloxy, cycloalkenylalkylcarbonyloxy, cycloalkenylalkenylcarbonyloxy, cycloalkenylalkynylcarbonyloxy, arylcarbonyloxy, arylalkylcarbonyloxy, arylalkenylcarbonyloxy, arylalkynylcarbonyloxy, heteroarylcarbonyloxy, heteroarylalkylcarbonyloxy, heteroarylalkenylcarbonyloxy, heteroarylalkynylcarbonyloxy, heterocyclylcarbonyloxy, heterocyclylalkylcarbonyloxy, heterocyclylalkenylcarbonyloxy, heterocyclylalkynylcarbonyloxy, aminocarbonyl, optionally substituted mono- or dialkylaminocarbonyl, optionally substituted mono- or diarylaminocarbonyl, optionally substituted mono- or diheteroarylaminocarbonyl, optionally substituted N-alkyl-N-arylaminocarbonyl, optionally substituted N-alkyl-N-heteroarylaminocarbonyl, optionally substituted mono- or diheteroarylaminocarbonyloxy, optionally substituted N-alkyl-N-arylaminocarbonyloxy, optionally substituted N-alkyl-N-heteroarylarninocarbonyloxy, aminocarbonylamino, optionally substituted mono- or dialkylaminocarbonylamino, optionally substituted mono- or diarylaminocarbonylamino, optionally substituted mono- or diheteroarylaminocarbonylamino, optionally substituted N-alkyl-N-arylaminocarbonylamino, optionally substituted N-alkyl-N-heteroarylaminocarbonylamino, optionally substituted mono- or dialkylcarbonylamino, optionally substituted mono- or diarylcarbonylamino, optionally substituted mono- or diheteroarylcarbonylamino, optionally substituted alkylcarbonyl-N-arylamino, optionally substituted arylcarbonyl-N-alkylamino, optionally substituted alkylcarbonyl-N-heteroarylamino, optionally substituted heteroarylcarbonyl-Nalkylamino, alkoxycarbonyloxy, alkenyloxycarbonyloxy, alkynyloxycarbonyloxy, cycloalkoxycarbonyloxy, cycloalkylalkoxycarbonyloxy, cycloalkylalkenyloxycarbonyloxy, cycloalkylalkynyloxycarbonyloxy, cycloalkenyloxycarbonyloxy, cycloalkenylalkoxycarbonyloxy, cycloalkenylalkenyloxycarbonyloxy, cycloalkenylalkynyloxycarbonyloxy, aryloxycarbonyloxy, arylalkoxycarbonyloxy, arylalkenyloxycarbonyloxy, arylalkynyloxycarbonyloxy, heteroaryloxycarbonyloxy, heteroarylalkoxycarbonyloxy, heteroarylalkenyloxycarbonyloxy, heteroarylalkynyloxycarbonyloxy, heterocyclyloxycarbonyloxy, heterocyclylalkoxycarbonyloxy, heterocyclylalkenyloxycarbonyloxy, heterocyclylalkynyloxycarbonyloxy, alkoxycarbonylamino, alkenyloxycarbonylamino, alkynyloxycarbonylamino, cycloalkoxycarbonylamino, cycloalkylalkoxycarbonylamino, cycloalkylalkenyloxycarbonylamino, cycloalkylalkynyloxycarbonylamino, cycloalkenyloxycarbonylamino, cycloalkenylalkoxycarbonylamino, cycloalkenylalkenyloxycarbonylamino, cycloalkenylalkynyloxycarbonylamino, aryloxycarbonylamnino, arylalkoxycarbonylamino, arylalkenyloxycarbonylamino, arylalkynyloxycarbonylamino, heteroaryloxycarbonylamino, heteroarylalkoxycarbonylamino, heteroarylalkenyloxycarbonylamino, heteroarylalkynyloxycarbonylamino, heterocyclyloxycarbonylamino, heterocyclylalkoxycarbonylarnino, heterocyclylalkenyloxycarbonylamino, heterocyclylalkynyloxycarbonylamino, alkoxycarbonylamino, alkenyloxycarbonylamino, alkynyloxycarbonylamino, cycloalkoxycarbonylamino, cycloalkylalkoxycarbonylamino, N-alkylcycloalkylalkenyloxycarbonylamino, cycloalkylalkynyloxycarbonylamino, cycloalkenyloxycarbonylamino, cycloalkenylalkoxycarbonylamino, cycloalkenylalkenyloxycarbonylamino, cycloalkenylalkynyloxycarbonylamino, aryloxycarbonylamino, arylalkoxycarbonylamino, arylalkynyloxycarbonylamino, arylalkynyloxycarbonylamino, heteroarylalkoxycarbonylamino, heteroarylalkenyloxycarbonylamino, heteroarylalkynyloxycarbonylamino, heterocyclylalkoxycarbonylamino, heterocyclylalkenyloxycarbonylamino, heterocyclylalkynyloxycarbonylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkenyloxycarbonylamino, haloalkynyloxycarbonylamino, haloalkylaminocarbonylamino, haloalkenylaminocarbonylamino, haloalkynylaminocarbonylamino, cyano, nitro or one of the groups —P(=O)$R^8R^9$, —P(=O)$OR^{10}R^8$, —P(=O)$OR^{10}OR^{11}$, —CH=N—NH—$(CH_2)_n$-alkyl, —CH=N—NH—$(CH_2)_n$-aryl, —CH=N—O—$(CH_2)_n$ -alkyl, —CH=N—O—$(CH_2)_n$-aryl, —O—$(CH_2)_m$—O—$(CH_2)_n$-alkyl, —CONHNH$(CH_2)_n$-alkyl and —CONHNH—$(CH_2)_n$-aryl;

$R^2$, $R^3$, $R^4$ and $R^5$ independently of one another are $R^{2a}$, hydrogen, alkyl, alkenyl or alkynyl;

$R^6$ is $OR^{12}$, alkylthio, haloalkylthio, alkenylthio, haloalkenylthio, alkynylthio, haloalkynylthio, alkylsulfinyl, haloalkylsulfinyl, alkenylsulfinyl, haloalkenylsulfinyl, alkynylsulfinyl, haloalkynylsulfinyl, alkylsulfonyl, haloalkylsulfonyl, alkenylsulfonyl, haloalkenylsulfonyl, alkynylsulfonyl, haloalkynylsulfonyl, cyano, cyanato, thiocyanato or halogen;

$R^7$ is hydrogen, tetrahydropyran-3-yl, tetrahydropyran-4-yl, tetrahydrothiopyran-3-yl, alkyl, cycloalkyl, alkoxy, alkoxyalkyl, alkylcarbonyl, alkoxycarbonyl, alkylthio, phenyl, where the eight last-mentioned groups are optionally substituted by one or more, identical or different radicals from the group consisting of halogen, alkylthio and alkyloxy, or two radicals $R^7$ bonded to a common carbon atom form a chain from the group consisting of $OCH_2CH_2O$, $OCH_2CH_2CH_2O$, $SCH_2CH_2S$ and $SCH_2CH_2CH_2S$, this optionally being substituted by one to four methyl groups, or two radicals $R^7$ bonded to directly adjacent carbon atoms form a bond or, with the carbon atoms carrying them, form a 3- to 6-membered ring optionally substituted by one or more, identical or different radicals from the group consisting of halogen, alkyl, alkylthio and alkoxy;

$R^8$ and $R^9$ independently of one another are alkyl, alkenyl, alkynyl, haloalkyl, haloalkenyl, haloalkynyl, optionally substituted aryl or optionally substituted arylalkyl;

$R^{10}$ and $R^{11}$ independently of one another are hydrogen or $R^8$, or $R^{10}$ and $R^{11}$, together form a $C_2$–$C_5$-alkylene chain;

$R^{12}$ is hydrogen, alkyl, haloalkyl, alkoxyalkyl, formyl, alkylcarbonyl, alkoxycarbonyl, alkylaminocarbonyl, dialkylaminocarbonyl, alkylsulfonyl, haloalkylsulfonyl, benzoyl or phenylsulfonyl, the two last-mentioned groups optionally being substituted by one or more, identical or different radicals from the group consisting of alkyl, haloalkyl, alkoxy, haloalkoxy, halogen, cyano and nitro;

$R^{13}$ is alkyl, alkenyl, alkynyl, haloalkyl, haloalkenyl, haloalkynyl, or phenyl optionally substituted by one or more, identical or different radicals from the group consisting of halogen, alkyl, haloalkyl and nitro;

L is a $C_1$–$C_6$-alkylene chain which is optionally substituted by one or more, identical or different radicals $R^2$;

Y is a divalent unit from the group consisting of $CHR^7$ and $C(R^7)_2$;

Z is a divalent unit from the group consisting of $CHR^7$ and $C(R^7)_2$;

v is 1;

w is 0,1, 2, 3 or 4;

m is 1,2or 3;

n is 0, 1, 2 or 3; and p is 0, 1 or 2, with the proviso that —L—$R^1$ should not be optionally substituted $CH_2$—O-phenyl when $R^2$ and $R^3$ are each chlorine and $R^4$ and $R^5$ are each hydrogen.

2. The benzoylcyclohexanedione as claimed in claim 1, in which $R^1$ is cycloalkyl, cycloalkenyl, aryl, cycloalkoxy, cycloalkylalkoxy, cycloalkylalkenyloxy, cycloalkylalkynyloxy, cycloalkenyloxy, cycloalkenylalkoxy, cycloalkenylalkenyloxy, cycloalkenylalkynyloxy, aryloxy, arylalkoxy, arylalkenyloxy, arylalkynyloxy, cycloalkylthio, cycloalkylalkylthio, cycloalkylalkenylthio, cycloalkylalkynylthio, cycloalkenylthio, cycloalkenylalkylthio, cycloalkenylalkenylthio, cycloalkenylalkynylthio, arylthio, arylalkylthio, arylalkenylthio, arylalkynylthio, cycloalkylsulfonyl, cycloalkylalkylsulfonyl, cycloalkylalkenylsulfonyl, cycloalkylalkynylsulfonyl, cycloalkenylsulfonyl, cycloalkenylalkylsulfonyl, cycloalkenylalkenylsulfonyl, cycloalkenylalkynylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, heterocyclylsulfonyl, heterocyclylalkylsulfonyl, heterocyclylalkenylsulfonyl, heterocyclylalkynylsulfonyl, cycloalkylsulfinyl, cycloalkylalkylsulfinyl, cycloalkylalkenylsulfinyl, cycloalkylalkynylsulfinyl, cycloalkenylsulfinyl, cycloalkenylalkylsulfinyl, cycloalkenylalkenylsulfinyl, cycloalkenylalkynylsulfinyl, arylsulfinyl, arylalkylsulfinyl, arylalkenylsulfinyl, arylalkynylsulfinyl, heteroarylsulfinyl, heteroarylalkylsulfinyl, heteroarylalkenylsulfinyl, heteroarylalkynylsulfinyl, heterocyclylsulfinyl, heterocyclylalkylsulfinyl, heterocyclylalkenylsulfinyl, heterocyclylalkynylsulfinyl, aminosulfonyl, optionally substituted mono- or dialkylaminosulfonyl, optionally substituted mono- or diarylaminosulfonyl, optionally substituted mono- or diheteroarylaminosulfonyl, optionally substituted N-alkyl-N-arylaminosulfonyl, optionally substituted N-alkyl-N-heteroarylaminosulfonyl, alkylsulfonyloxy, alkenylsulfonyloxy, alkynylsulfonyloxy, cycloalkylsulfonyloxy, cycloalkylalkylsulfonyloxy, cycloalkylalkenylsulfonyloxy, cycloalkylalkynylsulfonyloxy, cycloalkenylsulfonyloxy, cycloalkenylalkylsulfonyloxy, cycloalkenylalkenylsulfonyloxy, cycloalkenylalkynylsulfonyloxy, arylsulfonyloxy, arylalkylsulfonyloxy, arylalkenylsulfonyloxy, arylalkynylsulfonyloxy, heteroarylsulfonyloxy, heteroarylalkylsulfonyloxy, heteroarylalkenylsulfonyloxy, heteroarylalkynylsulfonyloxy, heterocyclylsulfonyloxy, heterocyclylalkylsulfonyloxy, heterocyclylalkenylsulfonyloxy, heterocyclylalkynylsulfonyloxy, alkylsulfonylamino, alkenylsulfonylamino, alkynylsulfonylamino, cycloalkylsulfonylamino, cycloalkylalkylsulfonylamino, cycloalkylalkenylsulfonylamino, cycloalkylalkynylsulfonylamino, cycloalkenylsulfonylamino, cycloalkenylalkylsulfonylamino, cycloalkenylalkenylsulfonylamino, cycloalkenylalkynylsulfonylamino, arylsulfonylamino, arylalkylsulfonylamino, arylalkenylsulfonylamino, arylalkynylsulfonylamino, heteroarylsulfonylamino, heteroarylalkylsulfonylamino, heteroarylalkenylsulfonylamino, heteroarylalkynylsulfonylamino, alkylsulfonyl-N-alkylamino, alkenylsulfonyl-N-alkylamino, alkynylsulfonyl-N-alkylamino, cycloalkylsulfonyl-N-alkylamino, cycloalkylalkylsulfonyl-N-alkylamino, cycloalkylalkenylsulfonyl-N-alkylamino, cycloalkylalkynylsulfonyl-N-alkylamino, cycloalkenylsulfonyl-N-alkylamino, cycloalkenylalkylsulfonyl-N-alkylamino, cycloalkenylalkenylsulfonyl-N-alkylamino, cycloalkenylalkynylsulfonyl-N-alkylamino, arylsulfonyl-N-alkylamino, heteroarylsulfonyl-N-alkylamino, arylalkylsulfonylamino, heteroarylalkylsulfonyl-N-alkylamino, arylalkenylsulfonyl-N-alkylamino, heteroarylalkenylsulfonyl-N-alkylamino, arylalkynylsulfonyl-N-alkylamino, heteroarylalkynylsulfonyl-N-alkylamino, heterocyclylsulfonyl-N-alkylamino, heterocyclylalkylsulfonyl-N-alkylamino, heterocyclylalkenylsulfonyl-N-alkylamino, heterocyclylalkynylsulfonyl-N-alkylamnino, alkylcarbonyl, alkenylcarbonyl, alkynylcarbonyl, cycloalkylcarbonyl, cycloalkylalkylcarbonyl, cycloalkylalkenylcarbonyl, cycloalkylalkynylcarbonyl, cycloalkenylcarbonyl, cycloalkenylalkylcarbonyl, cycloalkenylalkenylcarbonyl, cycloalkenylalkynylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, heterocyclylcarbonyl, carboxyl, alkoxycarbonyl, alkenyloxycarbonyl, alkynyloxycarbonyl, cycloalkoxycarbonyl, cycloalkylalkoxycarbonyl, cycloalkylalkenyloxycarbonyl, cycloalkylalkynyloxycarbonyl, cycloalkenyloxycarbonyl, cycloalkenylalkoxycarbonyl, cycloalkenylalkenyloxycarbonyl, cycloalkenylalkynyloxycarbonyl, aryloxycarbonyl, arylalkoxycarbonyl, arylalkenyloxycarbonyl, arylalkynyloxycarbonyl, heteroaryloxycarbonyl, heteroarylalkoxycarbonyl, heteroarylalkenyloxycarbonyl, heteroarylalkynyloxycarbonyl, heterocyclyloxycarbonyl, heterocyclylalkoxycarbonyl, heterocyclylalkenyloxycarbonyl, heterocyclylalkynyloxycarbonyl, aminocarbonyl, optionally substituted mono- or dialkylaminocarbonyl, optionally substituted mono- or diarylaminocarbonyl, optionally substituted mono- or diheteroarylaminocarbonyl, optionally substituted N-alkyl-N-arylarninocarbonyl, optionally substituted N-alkyl-N-heteroarylaminocarbonyl, optionally substituted mono- or dialkylcarbonylamino, optionally substituted mono- or diarylcarbonylamino, optionally substituted mono- or diheteroarylcarbonylamino, optionally substituted alkylcarbonyl-N-arylamino, optionally substituted arylcarbonyl-N-alkylamino, optionally substituted alkylcarbonyl-N-heteroarylamino, optionally substituted heteroarylcarbonyl-N-alkyl amino, formyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkylcarbonylamino, haloalkenylcarbonylamino, haloalkynylcarbonylamino, haloalkoxycarbonylamino, haloalkenyloxycarbonylamino, haloalkynyloxycarbonylamino, haloalkylcarbonyloxy, haloalkenylcarbonyloxy, haloalkynylcarbonyloxy, haloalkoxycarbonyloxy, haloalkenyloxycarbonyloxy, haloalkynyloxycarbonyloxy, haloalkylaminocarbonylamino, haloalkenylaminocarbonylamino, haloalkynylaminocarbonylamino, cyano, nitro, —P(=O)R$^8$R$^9$, —P(=O)OR$^{10}$R$^8$, —P(=O)OR$^{10}$OR$^{11}$, 2-tetrahydrofuranylmethoxy, 3-tetrahydrofuranylmethoxy, 2-tetrahydrothienylmethoxy, 3-tetrahydrothienylmethoxy, 2-tetrahydropyranylmethoxy, it being possible for the radicals cycloalkyl, cycloalkenyl, aryl, tetrahydrofuranyl, tetrahydrothienyl, tetrahydropyranyl, heteroaryl and heterocyclyl to be optionally mono- or polysubstituted, identically or differently, by R$^2$, or one of the groups —O—(CH$_2$)$_m$—O—(CH$_2$)$_n$—R$^{2a}$, —O—CH$_2$—S—(O)$_p$—R$^{13}$, —CONHNH—(CH$_2$)$_n$-alkyl and —CONHNH—(CH$_2$)$_n$-aryl, and R$^{2a}$ is (C$_1$–C$_6$)-alkoxy, (C$_2$–C$_6$)-alkenyloxy, (C$_3$–C$_6$)-alkynyloxy, halo-(C$_1$–C$_6$)-alkoxy, halo-(C$_2$–C$_6$)-alkenyloxy, halo-(C$_3$–C$_6$)-alkynyloxy or phenyl which is optionally mono-or polysubstituted by halogen, cyano, nitro, (C$_1$–C$_6$)-alkyl, (C$_1$–C$_6$)-alkoxy, halo-(C$_1$–C$_6$)-alkyl or halo-(C$_1$–C$_6$)-alkoxy.

3. The benzoylcyclohexanedione as claimed in claim 1, in which R$^2$, R$^3$, R$^4$ and R$^5$ independently of one another are hydrogen, alkyl, alkenyl, alkynyl, cycloalkyl, cycloalkenyl, cycloalkylalkyl, aryl, arylalkyl, heteroaryl, heteroarylalkyl, heterocyclyl, heterocyclylalkyl, hydroxyl, alkoxy, cycloalkoxy, aryloxy, heteroaryloxy, heterocyclyloxy, alkylthio, arylthio, heteroarylthio, heterocyclylthio, heterocyclylalkylthio, amino, mono- or dialkylamino, mono- or diarylamino, N-alkyl-N-arylamino, cycloalkylamino, alkylsulfonyl, arylsulfonyl, alkylsulfinyl, aminosulfonyl, mono- or dialkylaminosulfonyl, mono- or diarylaminosulfonyl, N-alkyl-N-arylaminosulfonyl, N-alkyl-N-heteroarylaminosulfonyl, alkylsulfonylamino, cycloalkylsulfonylamino, arylsulfonylamino, heteroarylsulfonylamino, cycloalkylsulfonyl-N-alkylamino, arylsulfonyl-N-alkylamino, heteroarylsulfonyl-N-alkylamino, heterocyclylsulfonyl-N-alkylamino, alkylcarbonyl, cycloalkylcarbonyl, arylcarbonyl, arylalkylcarbonyl, heteroarylcarbonyl, heterocyclylcarbonyl, carboxyl, alkoxycarbonyl, aryloxycarbonyl, arylalkoxycarbonyl, alkylcarbonyloxy, arylcarbonyloxy, arylalkylcarbonyloxy, aminocarbonyl, mono- or dialkylaminocarbonyl, N-alkyl-N-arylaminocarbonyl, N-alkyl-N-heteroarylaminocarbonyl, N-alkyl-N-arylaminocarbonyloxy, aminocarbonylamino, mono- or dialkylaminocarbonylamino, mono- or diarylaminocarbonylamino, mono- or diheteroarylaminocarbonylamino, N-alkyl-N-arylaminocarbonylamino, mono- or dialkylcarbonylamino, mono- or diarylcarbonylamino, alkylcarbonyl-N-arylamino, arylcarbonyl-N-alkylamino, alkoxycarbonyloxy, cycloalkoxycarbonyloxy, aryloxycarbonyloxy, arylalkoxycarbonyloxy, alkoxycarbonylamino, cycloalkoxycarbonylamino, aryloxycarbonylamino, alkoxycarbonyl-N-alkylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkenylcarbonyl, haloalkynylcarbonyl, haloalkoxycarbonyl, haloalkenyloxycarbonyl, haloalkynyloxycarbonyl, haloalkylaminocarbonyl, haloalkenylaminocarbonyl, haloalkynylaminocarbonyl, haloalkoxycarbonylamino, haloalkylaminocarbonylamino, cyano, nitro, arylalkoxyalkoxy or alkoxyalkoxyalkoxy;

$R^6$ is $OR^{12}$, alkylthio, alkylsulfonyl, cyano, cyanato, thiocyanato or halogen;

$R^7$ is hydrogen, alkyl, cycloalkyl, alkoxy, alkoxyalkyl, alkylcarbonyl, alkoxycarbonyl, alkylthio or phenyl, or two radicals $R^7$ bonded to a common carbon atom form a chain from the group consisting of $OCH_2CH_2O$ and $OCH_2CH_2CH_2O$, this optionally being substituted by one to four methyl groups, or two radicals $R^7$ bonded to directly adjacent carbon atoms form a bond or, with the carbon atoms carrying them, form a 3- to 6-membered ring optionally substituted by one or more, identical or different radicals from the group consisting of halogen, alkyl, alkylthio and alkoxy;

$R^8$ and $R^9$ independently of one another are alkyl, alkenyl, alkynyl, haloalkyl, optionally substituted aryl or optionally substituted arylalkyl;

$R^{12}$ is hydrogen, haloalkyl, alkoxyalkyl, formyl, alkylcarbonyl, alkoxycarbonyl, alkylsulfonyl, haloalkylsulfonyl, benzoyl or phenylsulfonyl, the two last-mentioned groups optionally being substituted by one or more, identical or different radicals from the group consisting of alkyl, haloalkyl, alkoxy, haloalkoxy, halogen, cyano and nitro;

L is a $(C_1-C_6)$-alkylene chain which is optionally substituted by one to four identical or different radicals $R^2$;

Y is a divalent unit from the group consisting of $CHR^7$ or $C(R^7)_2$;

Z is a divalent unit from the group consisting of $CHR^7$ and $C(R^7)_2$ and w is 0, 1, 2 or 3.

4. The benzoylcyclohexanedione as claimed in claim 1 in which $R^1$ is halo-$(C_1-C_6)$-alkoxy, halo-$(C_2-C_6)$-alkenyloxy, halo-$(C_3-C_6)$-alkynyloxy, halo-$(C_1-C_6)$-alkylthio, halo-$(C_2-C_6)$-alkenylthio, halo-$(C_3-C_6)$-alkynylthio, halo-$(C_1-C_6)$-alkylamino, halo-$(C_2-C_6)$-alkenylamino, halo-$(C_3-C_6)$-alkynylamino, halo-$(C_1-C_6)$-alkylsulfonyl, halo-$(C_2-C_6)$-alkenylsulfonyl, halo-$(C_3-C_6)$-alkynylsulfonyl, halo-$(C_1-C_6)$-alkylsulfonyl, halo-$(C_2-C_6)$-alkenylsulfinyl, halo-$(C_3-C_6)$-alkynylsulfinyl, halo-$(C_1-C_6)$-alkylcarbonyl, halo-$(C_2-C_6)$-alkenylcarbonyl, halo-$(C_3-C_6)$-alkynylcarbonyl, halo-$(C_1-C_6)$-alkoxycarbonyl, halo-$(C_2-C_6)$-alkenyloxycarbonyl, halo-$(C_3-C_6)$-alkynyloxycarbony, halo-$(C_1-C_6)$-alkylaminocarbony, halo-$(C_2-C_6)$-alkenylaminocarbony, halo-$(C_3-C_6)$-alkynylaminocarbonyl, halo-$(C_1-C_6)$-alkylcarbonylamino, halo-$(C_2-C_6)$-alkenylcarbonylamino, halo-$(C_3-C_6)$ alkynylcarbonylamino, halo-$(C_1-C_6)$-alkoxycarbonylamino, halo-$(C_2-C_6)$-alkenyloxycarbonylamino, halo-$(C_3-C_6)$-alkynyloxycarbonylamino, halo-$(C_1-C_6)$-alkylcarbonyloxy, halo-$(C_2-C_6)$-alkenylcarbonyloxy, halo-$(C_3-C_6)$-alkynylcarbonyloxy, halo-$(C_1-C_6)$-alkoxycarbonyloxy, halo-$(C_1-C_6)$-alkenyloxycarbonyloxy, halo-$(C_3-C_6)$-alkynyloxycarbonyloxy, halo-$(C_1-C_6)$-alkylaminocarbonylamino, halo-$(C_2-C_6)$-alkenylaminocarbonylamino, halo-$(C_3-C_6)$-alkynylaminocarbonylamino, —O—$(CH_2)_m$—O—$(CH_2)_n$—$R^{2a}$, —P(=O)$R^8R^9$, —P(=O)$OR^{10}R^8$, —P(=O)$OR^{10}OR^{11}$, 2-tetrahydrofuranylmethoxy, 3-tetrahydrofuranylmethoxy, 2-tetrahydrothienylmethoxy, 3-tetrahydrothienylmethoxy, 2-tetrahydropyranylmethoxy, $(C_3-C_6)$-cyclo-$(C_1-C_6)$-alkyl, $(C_3-C_6)$-cyclo-$(C_2-C_6)$-alkenyl, $(C_3-C_6)$-cyclo-$(C_1-C_6)$-alkoxy, $C_3-C_6$-cyclo-$(C_1-C_6)$-alkyl-$(C_3-C_6)$-alkoxy, $C_3-C_6$-cyclo-$(C_1-C_6)$-alkyl-$(C_2-C_6)$-alkenyloxy, $C_3-C_6$-cyclo-$(C_1-C_6)$-alkyl-$(C_2-C_6)$-alkynyloxy, $(C_3-C_6)$-cycloalkenyloxy, $(C_3-C_6)$-cycloalkenyl-$(C_1-C_6)$-alkoxy, $C_2-C_6$-cycloalkenyl-$(C_2-C_6)$-alkenyloxy, $C_3-C_6$-cycloalkenyl-$(C_2-C_6)$-alkynyloxy, the last-mentioned 15 radicals optionally being substituted by one or more, identical or different radicals from the group consisting of hydrogen, $C_1-C_6$-alkyl, halo-$(C_1-C_6)$-alkyl, $C_1-C_6$-alkoxy, halo-$(C_1-C_6)$-alkoxy, $C_1-C_6$-alkylthio, halo-$(C_1-C_6)$-alkylthio, $C_1-C_6$-alkylsulfinyl, halo-$(C_1-C_6)$-alkylsulfonyl, $C_1-C_6$-alkylsulfonyl, halo-$(C_1-C_6)$-alkylsulfonyl, $C_1-C_6$-alkylcarbonylamino, $C_1-C_6$-alkylsulfonylamino, halogen, nitro and cyano.

5. The benzoylcyclohexanedione as claimed in claim 1 in which $R^2$, $R^3$ and $R^4$ independently of one another are hydrogen, alkyl, alkenyl, alkynyl, cycloalkyl, cycloalkenyl, cycloalkylalkyl, hydroxyl, alkoxy, cycloalkoxy, alkylthio, amino, mono- or dialkylamino, cycloalkylamino, alkylsulfonyl, alkylsulfinyl, aminosulfonyl, mono- or dialkylaminosulfonyl, alkylsulfonylamino, cycloalkylsulfonylamino, alkylcarbonyl, cycloalkylcarbonyl, alkoxycarbonyl, alkylcarbonyloxy, aminocarbonyl, mono- or dialkylaminocarbonyl, alkoxycarbonyloxy, cycloalkoxycarbonyloxy, alkoxycarbonylamino, formyl, halogen, haloalkyl, haloalkenyl, haloalkynyl, haloalkoxy, haloalkenyloxy, haloalkynyloxy, haloalkylthio, haloalkenylthio, haloalkynylthio, haloalkylamino, haloalkenylamino, haloalkynylamino, haloalkylsulfonyl, haloalkenylsulfonyl, haloalkynylsulfonyl, haloalkylsulfinyl, haloalkenylsulfinyl, haloalkynylsulfinyl, haloalkylcarbonyl, haloalkoxycarbonyl, haloalkenyloxycarbonyl, haloalkynyloxycarbonyl, haloalkylaminocarbonyl, cyano, nitro, $R^5$ is hydrogen $R^6$ is $OR^{12}$ or $C_1$–$C_6$-alkylthio;

$R^7$ is hydrogen, $C_1$–$C_6$-alkyl, $C_3$–$C_6$-cycloalkyl, $C_1$–$C_6$-alkoxy, $C_1$–$C_6$-alkylthio or phenyl;

$R^8$ and $R^9$ independently of one another are $C_1$–$C_6$-alkyl, $C_2$–$C_6$-alkenyl, $C_2$–$C_6$-alkynyl, halo-$C_1$–$C_6$-alkyl, aryl or benzyl;

$R^{12}$ is hydrogen, halo-$C_1$–$C_6$-alkyl, $C_1$–$C_6$-alkylcarbonyl, $C_1$–$C_6$-alkoxycarbonyl, $C_1$–$C_6$-alkylsulfonyl, benzoyl or phenylsulfonyl, the two last-mentioned groups optionally being substituted by one or more, identical or different radicals from the group consisting of $C_1$–$C_6$-alkyl, halo-$C_1$–$C_6$-alkyl, $C_1$–$C_6$-alkoxy, halo-$C_1$–$C_6$-alkoxy, halogen, cyano and nitro;

L is a $C_1$–$C_3$-alkylene chain which is optionally substituted by one to four identical or different radicals $R^2$ and Y is a divalent unit from the group consisting of $CHR^7$ and $C(R^7)_2$, and Z is a divalent unit from the group consisting of $CHR^7$ and $C(R^7)_2$.

6. A benzoylcyclohexanedione as claimed in claim 1, in which $R^1$ is halo-($C_1$–$C_6$)-alkoxy, halo-($C_2$–$C_6$)-alkenyloxy, halo-($C_3$–$C_6$)-alkynyloxy, halo-($C_1$–$C_6$)-alkylthio, halo-($C_2$–$C_6$)-alkenylthio, halo-($C_3$–$C_6$)-alkynylthio, halo-($C_1$–$C_6$)-alkylamino, halo-($C_2$–$C_6$)-alkenylamino, halo-($C_3$–$C_6$)-alkynylamino, halo-($C_1$–$C_6$)-alkylsulfonyl, halo-($C_2$–$C_6$)-alkenylsulfonyl, halo-($C_3$–$C_6$)-alkynylsulfonyl, halo-($C_1$–$C_6$)-alkylsulfinyl, halo-($C_2$–$C_6$)-alkenylsulfinyl, halo-($C_3$–$C_6$)-alkynylsulfinyl, halo-($C_1$–$C_6$)-alkylcarbonyl, halo-($C_2$–$C_6$)-alkenylcarbonyl, halo-($C_3$–$C_6$)-alkynylcarbonyl, halo-($C_1$–$C_6$)-alkoxycarbonyl, halo-($C_2$–$C_6$)-alkenyloxycarbonyl, halo-($C_3$–$C_6$)-alkynyloxycarbonyl, halo-($C_1$–$C_6$)-alkylaminocarbonyl, halo-($C_2$–$C_6$)-alkenylaminocarbonyl, halo-($C_3$–$C_6$)-alkynylaminocarbonyl, halo-($C_1$–$C_6$)-alkylcarbonylamino, halo-($C_2$–$C_6$)-alkenylcarbonylamino, halo-($C_3$–$C_6$)-alkynylcarbonylamino, halo-($C_1$–$C_6$)-alkoxycarbonylamino, halo-($C_2$–$C_6$)-alkenyloxycarbonylamino, halo-($C_3$–$C_6$)-alkynyloxycarbonylamino, halo-($C_1$–$C_6$)-alkylcarbonyloxy, halo-($C_2$–$C_6$)-alkenylcarbonyloxy, halo-($C_3$–$C_6$)-alkynylcarbonyloxy, halo-($C_1$–$C_6$)-alkoxycarbonyloxy, halo-($C_2$–$C_6$)-alkenyloxycarbonyloxy, halo-($C_3$–$C_6$)-alkynyloxycarbonyloxy, halo-($C_1$–$C_6$)-alkylaminocarbonylamino, halo-($C_2$–$C_6$)-alkenylaminocarbonylamino, halo-($C_3$–$C_6$)-alkynylaminocarbonylamino, —O—$(CH_2)_m$—O—$(CH_2)_n$—$R^{2a}$;

$R^2$ and $R^3$ independently of one another are hydrogen, $C_1$–$C_6$-alkyl, halo-($C_1$–$C_6$)-alkyl, $C_1$–$C_6$-alkoxy, halo-($C_1$–$C_6$)-alkoxy, $C_1$–$C_6$-alkylthio, halo-($C_1$–$C_6$)-alkylthio, $C_1$–$C_6$-alkylsulfinyl, halo-($C_1$–$C_6$)-alkylsulfinyl, $C_1$–$C_6$-alkylsulfonyl, halo-($C_1$–$C_6$)-alkylsulfonyl, halogen, nitro and cyano;

$R^4$ is hydrogen;

$R^6$ is $OR^{12}$;

$R^7$ is hydrogen or $C_1$–$C_6$-alkyl;

$R^{12}$ is hydrogen, $C_1$–$C_6$-alkylsulfonyl, benzoyl, phenylsulfonyl, the two last-mentioned groups optionally being substituted by one or more, identical or different radicals from the group consisting of $C_1$–$C_6$-alkyl, halo-($C_1$–$C_6$)-alkyl, $C_1$–$C_6$-alkoxy, halo-($C_1$–$C_6$)-alkoxy, halogen, cyano and nitro;

L is $CH_2$ optionally substituted by one or two identical or different $C_1$–$C_6$-alkyl or $C_1$–$C_6$-alkoxy radicals;

Y and Z independently of one another are $CHR^7$ or $C(R^7)_2$;

v is 1 and w is 0, 1 or 2.

7. A herbicidal composition, comprising a herbicidally active amount of at least one compound of the formula (I) as claimed in claim 1.

8. A herbicidal composition as claimed in claim 7 as a mixture with formulation auxiliaries.

9. A process for controlling undesired plants, which comprises applying an active amount of at least one compound of the formula (I) as claimed in claim 1 or of a herbicidal composition as claimed in claim 7 or 8 to the plants or to the site of the undesired plant growth.

10. A method for controlling undesired plants, which comprises applying an active amount of at least one compound of formula (I) as claimed in claim 1 to said plants or to an area where they reside.

11. The method as claimed in claim 10, wherein the compounds of the formula (I) are employed for controlling undesired plants in crops of useful plants.

12. The method as claimed in claim 11, wherein the useful plants are transgenic useful plants.

* * * * *